(12) United States Patent
Austin et al.

(10) Patent No.: US 8,153,633 B2
(45) Date of Patent: Apr. 10, 2012

(54) PHTHALAZINE COMPOUNDS, COMPOSITIONS AND METHODS OF USE

(75) Inventors: Richard J. Austin, San Francisco, CA (US); Jacob Kaizerman, Redwood City, CA (US); Brian Lucas, San Francisco, CA (US); Dustin L. McMinn, Pacifica, CA (US); Jay Powers, Pacifica, CA (US)

(73) Assignee: Amgen Inc., Thousand Oaks, CA (US)

( * ) Notice: Subject to any disclaimer, the term of this patent is extended or adjusted under 35 U.S.C. 154(b) by 834 days.

(21) Appl. No.: 12/214,901

(22) Filed: Jun. 23, 2008

(65) Prior Publication Data

US 2009/0048259 A1    Feb. 19, 2009

Related U.S. Application Data

(60) Provisional application No. 60/937,196, filed on Jun. 25, 2007.

(51) Int. Cl.
*A61K 31/50* (2006.01)
*A61K 31/501* (2006.01)
*C07D 237/30* (2006.01)

(52) U.S. Cl. .................. 514/252.02; 544/237
(58) Field of Classification Search .................. 544/237; 514/252.02
See application file for complete search history.

(56) References Cited

FOREIGN PATENT DOCUMENTS
WO    WO 2005/033288 A    4/2005

OTHER PUBLICATIONS

Pinedo et al, "Translational Research . . . ", The Oncologist 2000; 5(suppl1); 1-2. [www.The Oncologist.com].*
McMahon, G., VEGF Receptor Signaling in Tumor Angiogenisis. The Oncologist 2000;5(suppl 1):3-10. [www.The Oncologist.com].*
Eguchi et al., Chem. Pharm. Bull. 39(8), pp. 2009-2015, (1991).*
Eguchi, Yukuo et al., "Studies on antiatherosclerotic agents. Synthesis and inhibitory activities on platelet aggregation of 4-aryl derivatives of 7-ethoxycarbonyl-6,8-dimethyl-1(2H)-phthalazinone", Chemical & Pharmaceutical Bulletin 39(8), 2009-2015 (1991).

* cited by examiner

*Primary Examiner* — Paul V. Ward
(74) *Attorney, Agent, or Firm* — Joseph W. Bulock

(57) ABSTRACT

The present invention relates generally to compounds represented in Formula I, pharmaceutical compositions comprising them and methods of treating of diseases or disorders such as cancer.

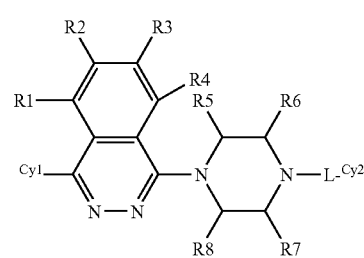

27 Claims, 2 Drawing Sheets

PHTHALAZINE COMPOUNDS, COMPOSITIONS AND METHODS OF USE

CROSS-REFERENCE TO RELATED PATENT APPLICATIONS

This application claims the benefit of priority of U.S. Provisional Patent Application No. 60/937,196, filed on Jun. 25, 2007.

FIELD OF THE INVENTION

This invention relates generally to the field of medicine and, more specifically, to novel compounds and pharmaceutical compositions comprising them, uses and methods for treating cancer.

BACKGROUND OF THE INVENTION

Members of the Hedgehog (Hh) family of signaling molecules mediate many important short and long range patterning processes during invertebrate and vertebrate development. Pattern formation is the activity by which embryonic cells form ordered spatial arrangements of differentiated issues. Hedgehog proteins were first discovered in *Drosophila*. Although some crucial differences exist, the signalling mechanisms are generally well conserved between *Drosophila* and higher organisms. In the fly, a single Hh gene regulates segmental and imaginal disc patterning. In contrast, in vertebrates, an Hh gene family is involved in the control of left-right asymmetry, polarity in the CNS, somites and limb, organogenesis, chondrogenesis and spermatogenesis. Three Hh homologues have been identified in humans: Sonic hedgehog (SHH), Indian hedgehog (IHH) and Desert hedgehog (DHH). The Hh signalling cascade is initiated by Hh binding to the Patched 1 proteins (PTCH1 in humans) on the target cell. In the absence of the Hh ligand, PTCH1 represses the activity of Smoothened (SMO in humans, Smo in mouse and smo in *Drosophila*), a G-protein-coupled receptor (GPCR)-like protein, presumably, by preventing its localization to the cell surface. Mammalian Hh signaling requires the presence of non-motile cilia to which SMO and other downstream pathway components need to transit in order to achieve activation of GLI transcription factors, the cubis interruptus (Ci) orthologues. The activator and repressor forms of Ci in mammals are represented by three separate zinc-finger proteins, with GLI1 and GLI2 functioning mostly as activators and GLI3 as a repressor. For review, see Rubin L. L. et al. (2006) *Nature Reviews*, vol 5, 1026-1033. The mechanism by which this signaling cascade regulates proliferation involves the activation of cyclins and cyclin-dependent kinases. The control of differentiation might be occurring via the production of other secreted proteins, including neurotrophic and angiogenic factors.

Medicinal chemistry efforts to identify inhibitors of Hh pathway began when Richard Keeler and co-workers isolated teratogens from *Veratrum californicum* in 1964. Subsequent research established that the previously known alkaloid jervine and the newly discovered alkaloid cyclopamine were able to induce cyclopia. Almost four decades later, the heptahelical bundle of Smo was identified as the site of binding of cyclopamine using its photoaffinity and fluorescent derivatives. Chen, J. et al. (2002) *Genes & Develop.* 16: 2743-2748; Chen, J. et al. (2002) *Proc. Natl. Acad. Sci. USA* 99: 14071-14076; Frank-Kamenetsky, M. et al. (2002) *J. Biol.* 1, article 10. Several assays are used to screen for antagonists to Smo in vitro. One of the assays for high throughput screening examines the overall activity of the Hh pathway in a cellular context by determining the degree of activity of the downstream effector protein GLI. Chen et al., supra. Cell lines of this type often incorporate a GLI dependent luciferase reporter for the assay readout. The luciferase signal may be boosted by other engineer modifications, such as the addition of biologically active Shh, for example, by attaching an octyl moiety to its N terminus, or the utilization of cell lines that lack PTCH1 function. Alternatively, direct binding to Smo can be measured through the displacement of a fluorescent cyclopamine derivative. In addition, tumor xenograft models based on SCLC, biliary, prostate, pancreatic and medulloblastoma lines can also be used.

In the recent years it was established that aberrant activation of the Hh signaling pathway can lead to cancer. Gorlin syndrome (GS), or nevoid basal cell carcinoma syndrome, is an autosomal dominant genetic disease that is characterized by development abnormalities and tumor predisposition. Virtually all individuals with Gorlin syndrome develop basal cell carcinomas (BCC), usually at multiple sites, and are predisposed to other kinds of cancer as well, especially medulloblastoma, a tumor of cerebellar granule neuron progenitor cells, rhabdomyosarcoma, a muscle tumor, as well as ovarian fibromas and sarcomas. Borzillo, G. et al. (2005) *Curr. Topics in Med. Chem.* 5: 147-157.

BCC is the most common human cancer, accounting for about 70% of human skin cancers, and representing at least one third of all cancer diagnosed in the US each year. More than 99% of BCC cases arise sporadically in the population, with only 0.5% of cases arising in individuals with GS. BCC rarely metastasizes, but can be locally aggressive and recurrent. Inactivating mutations in PTCH1 occur most commonly in these tumors. A subset of BCC is driven via mutations in SMO, and these mutations activate the pathway by generating proteins with decreased sensitivity to PTCH1 suppression.

Medulloblastoma (MB) is a brain tumor that forms in the cerebellum of children and young adults, and may be the end result of defect in cerebellar organogenesis. MB, in addition to BCC, has a well recognized involvement of the Hh pathway. The outcome of this cancer is almost invariably poor. Surgery with subsequent radiation or chemotherapy increases survival to greater than 50%, but there is severe treatment-associated morbidity, including mental retardation. Hh-pathway antagonists have been tested in cell culture and mouse models of medulloblastoma. A new class of SMO-binding Hh antagonists has been demonstrated to be very potent. Berman C. M. et al. (2002) *Science* 297: 1559-1561.

Hh pathway has been implicated in many other types of cancer, including pancreatic cancer, other tumors of the gastrointestinal (GI) tract and prostate cancer. Abnormal expression of SHH, PTCH1 and SMO has been shown early in the formation of human pancreatic tumors. Thayer, S. P. et al. (2003) *Nature* 425: 313-317. Several pancreatic cancer cell lines were found to be PTCH1 and SMO-positive and growth inhibited in vitro by cyclopamine, suggesting an active autocrine loop through which tumor cells both make and respond to Hh ligand. Furthermore, systemic treatment with cyclopamine slowed the growth of tumors formed when these cell lines are implanted into immunocompromised mice. Similar observations were made for pancreatic and other GI tumors. Berman, D. M. et al. (2003) *Nature* 425: 846-851. Similar data was provided for prostate cancer as well, including SHH overexpression in tumor biopsies, especially in higher Gleason grade tumors, and in vitro and in vivo inhibitory effects of cyclopamine on growth of prostate cancer cell lines. The Hh pathway was further implicated in prostate tumor metastasis, as the capacity of AT6.3 cells to metastasize to the lung was completely abrogated by cyclopamine, and AT2.1, a rarely metastasizing clone, could be induced to metastasize by overexpression of GLI1, in a cyclopamine-insensitive manner.

It has been demonstrated recently that Hh may be involved in the development of a significant subset of small cell lung carcinoma (SCLC). Watkins, D. N. et al. (2003) *Nature* 422: 313-317. In this study, Shh pathway components were found to be reactivated in a mouse model of acute airway damage caused by naphthalene. About 50-70% of SCLC lines and primary tumors expressed transcripts (SHH, PTCH1, GLI1) indicative of activated Shh signaling. Cyclopamine blocked the growth of only those cells with persistent Hh signaling, and this effect was abrogated by overexpression of GLI1. None of the effects of cyclopamine could be reproduced with tomatidine, a compound that is structurally similar but inactive against SMO.

These results demonstrate that Hh pathway is an important pharmacological target for a variety of cancers. Compounds and compositions of the current invention present an important treatment option for all tumors driven by inappropriate Hh signaling.

SUMMARY OF THE INVENTION

The present invention relates to compounds of Formula I

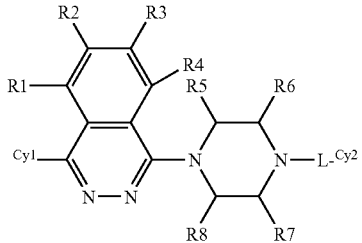

or a pharmaceutically acceptable salt thereof, wherein all substituents are as defined in Detailed Description.

The invention provides pharmaceutical compositions comprising compounds of Formula I, solvates, prodrugs and or pharmaceutically acceptable salts thereof and a pharmaceutically acceptable carrier.

In one aspect, the invention provides methods of treating cancer, comprising administering a therapeutically effective amount of a compound of Formula I or a pharmaceutically acceptable salt thereof to a subject in need thereof. In one aspect, cancer can be pancreatic cancer. In another aspect, cancer can be basal cell carcinoma, medulloblastoma, Gorlin syndrome, prostate or lung cancer. The invention further provides methods for treating cancer further comprising administering a compound selected from the group consisting of antibiotics, alkylating agents, antimetabolite agents, hormonal agents, immunological agents and interferon-type agents.

In one aspect, the invention provides methods of treating angiogenesis in a subject, comprising administering a therapeutically effective amount of a compound of Formula I or a pharmaceutically acceptable salt thereof to a subject in need thereof. In another aspect, the invention provides methods of reducing blood flow in a tumor in a subject, comprising administering a therapeutically effective amount of a compound of Formula I or a pharmaceutically acceptable salt thereof to a subject in need thereof.

In one aspect, the subject can be human.

DETAILED DESCRIPTION OF THE INVENTION

I. Definitions

Figure 1:
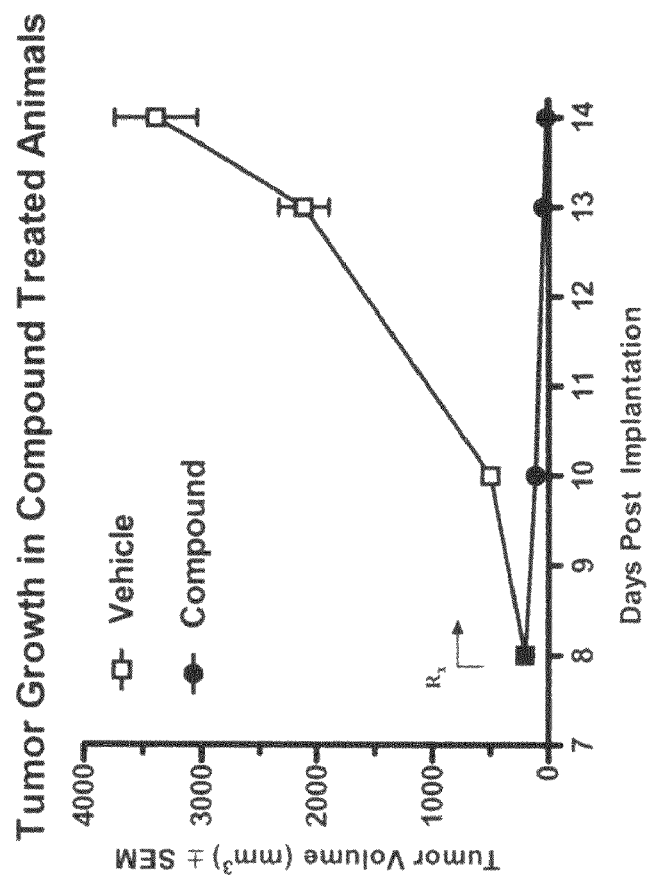
FIG. 1 demonstrates that growth of a primary pancreatic tumor is reduced in a compound treated mice compare to a vehicle treated mice.

"Treating" or "treatment" of a disease includes: (1) preventing the disease, i.e., causing the clinical symptoms of the disease not to develop in a subject that may be or has been exposed to the disease or conditions that may cause the disease, or predisposed to the disease but does not yet experience or display symptoms of the disease, (2) inhibiting the disease, i.e., arresting or reducing the development of the disease or any of its clinical symptoms, or (3) relieving the disease, i.e., causing regression of the disease or any of its clinical symptoms.

The phrase "therapeutically effective amount" is the amount of the compound of the invention that will achieve the goal of prevention of the disorder or improvement in disorder severity and the frequency of incidence. The improvement in disorder severity includes the reversal of the disease, as well as slowing down the progression of the disease.

As used herein, "cancer" and "cancerous" refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon cancer, medulloblastoma, and head and neck cancer. While the term "cancer" as used herein is not limited to any one specific form of the disease, it is believed that the methods of the invention will be particularly effective for cancers which are found to be accompanied by aberrant signaling in Hh pathway.

Unless otherwise specified, the following definitions apply to terms found in the specification and claims:

The term "H" denotes a single hydrogen atom. This radical may be attached, for example, to an oxygen atom to form a hydroxyl radical.

The term "alkyl" by itself or as part of another substituent, means, unless otherwise stated, a straight or branched chain, or cyclic, saturated hydrocarbon having the indicated number of carbon atoms (i.e., $C_1$-$C_8$ means one to eight carbons). For example, $C_1$-$C_8$ alkyl is meant to include, but is not limited to methyl, ethyl, propyl, isopropyl, butyl, sec-butyl, tert-butyl, pentyl, isopentyl, neopentyl, hexyl, isohexyl, cyclohexyl, cyclohexylmethyl, cyclopropylmethyl and neohexyl.

The term "alkenyl" as used herein refers to a straight or branched chain unsaturated hydrocarbon having the indicated number of carbon atoms (i.e., $C_2$-$C_8$ means two to eight carbons) and at least one double bond. Examples of a $C_2$-$C_8$ alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene.

The term "alkylene" refers to a divalent alkyl group (e.g., an alkyl group attached to two other moieties, typically as a linking group). Examples of a ($C_1$-$C_8$) alkylene include —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, as well as branched versions thereof. The term "alkenylene" refers to a divalent alkenyl group (e.g., an alkenyl group attached to two other moieties, typically as a linking group). Examples of a $C_2$-$C_8$ alkenylene group include —CH=CH—, —$CH_2$CH=CH—, —$CH_2$CH=CH$CH_2$—, as well as branched versions thereof.

Typically, an alkyl, alkenyl, alkylene, or alkenylene group will have from 1 to 24 carbon atoms, with those groups having 10 or fewer carbon atoms being preferred in the present invention. A "lower alkyl" "lower alkenyl" or "lower alkylene" is a shorter chain alkyl or alkylene group, generally having eight or fewer carbon atoms.

The term "heteroatom" is meant to include oxygen (O), nitrogen (N), sulfur (S) and silicon (Si).

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl."

The term "cycloalkyl" by itself or in combination with other terms, represents, unless otherwise stated, cyclic version of "alkyl". Thus, the term "cycloalkyl" is meant to be included in the terms "alkyl". Examples of cycloalkyl include cyclopentyl, cyclohexyl, 1-cyclohexenyl, 3-cyclohexenyl, cycloheptyl, cyclobutylene, cyclohexylene and the like.

The terms "heterocycloalkyl" and "heterocycloalkylene" as used herein, refer to cyclic versions of heteroalkyl and heteroalkylene as described above. Examples of heterocycloalkyl include pyrrolidinyl, tetrahydrofuranyl, dioxolanyl, imidazolinyl, pyrazolidinyl, piperidinyl, morpholinyl, dithanyl, thiomorpholinyl, piperainyl, and trithanyl. Examples of heterocycloalkenyl include pyrrolinyl. imidazolinyl, and 2H-pyranyl.

The term "aryl" as used herein refers to a 6- to 14-membered monocyclic, bicyclic or tricyclic aromatic hydrocarbon ring system. Examples of an aryl group include phenyl and naphthyl.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl and oxazolyl. A heteroaryl group can be unsubstituted or optionally substituted with one or more substituents as described herein below.

The terms "arylalkyl" and "heteroarylalkyl" are meant to include those radicals in which an aryl or heteroaryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like). "Heteroarylalkyl" is meant to include those radicals in which a heteroaryl group is attached to an alkyl group.

The term "heterocycle", "heterocyclic residue" or "heterocyclyl" as used herein refer to 3- to 14-membered ring systems which are either saturated, unsaturated, or aromatic, and which contain from 1 to 4 heteroatoms independently selected from nitrogen, oxygen and sulfur, and wherein the nitrogen and sulfur heteroatoms may be optionally oxidized, and the nitrogen heteroatom may be optionally quaternized, including monocyclic, bicyclic, and tricyclic ring systems. The bicyclic and tricyclic ring systems may encompass a heterocycle or heteroaryl fused to a benzene ring. The heterocycle may be attached via any heteroatom or carbon atom. Heterocycles include heteroaryls, heterocycloalkyls, and heterocycloalkenyls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl. A heterocycle group can be unsubstituted or optionally substituted with one or more substituents as described herein below.

The term "alkoxy" as used herein refers to an —O-alkyl group. For example, an alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl. The term "alkoxyalkyl" refers to an alkoxy group appended to an alkyl radical. The term "aryloxy" as used herein refers to an —O-aryl group. The term "alkoxyaryl" refers to an alkoxy group attached to an aryl radical.

The term "amino" refers to a chemical functionality —NR'R", wherein R' and R' are independently hydrogen, alkyl or aryl.

The term "aminoalkyl," as used herein, refers to an alkyl group (typically one to eight carbon atoms) wherein one or more of the $C_1$-$C_8$ alkyl group's hydrogen atoms are replaced with an amine. Examples of aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2CH_2N(CH_3)_2$, t-butylaminomethyl, isopropylaminomethyl and the like. The term "alkylamino" refers to an amino group wherein one or more hydrogen atoms is replaced with an alkyl group. Similarly, the term "dialkylamino" refers to an amino group having two attached alkyl groups that can be the same or different.

The term "halo" or "halogen" as used herein refers to —F, —Cl, —Br or —I.

The term "haloalkyl," as used herein, refers to a $C_1$-$C_6$ alkyl group wherein one or more of the $C_1$-$C_6$ alkyl group's hydrogen atoms is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

The term "sulfonyl", whether used alone or linked to other terms such as alkylsulfonyl, denotes respectively divalent radicals —$SO_2$—.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—.

The term "aminocarbonyl" denotes an amide group of the formula —C(=O)$NH_2$.

The term "protected" with respect to hydroxyl groups, amine groups, carboxyl groups and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., ($3^{rd}$ Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

The compounds of the invention can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of the compounds of the invention, including tautomeric forms of the compound.

Certain compounds of the invention may have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, and mixtures thereof, including a racemic mixture. Optical isomers of the smoothened receptor modulators can be obtained by known techniques such as asymmetric synthesis, chiral chromatography, simulated moving bed technology or via chemical separation of stereoisomers through the employment of optically active resolving agents.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

A "pharmaceutically acceptable" denotes any salt or ester of a compound of this invention, or any other compound which upon administration to a patient is capable of providing (directly or indirectly) a compound of this invention, or a metabolite or residue thereof.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al. (1977) J. Pharm. Sci. 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester, but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, e.g., cancer therapeutic agents, research reagents, e.g., assay reagents, and diagnostic agents, e.g., in vivo imaging agents. All isotopic variations of the compounds of the invention, whether radioactive or not, are intended to be encompassed within the scope of the invention.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

II. Compounds that Modulate Smoothened Receptor and Pharmaceutical Compositions Comprising them Administration and Dosage The present invention relates to compounds useful in treating cancer and angiogenesis as defined by Formula I

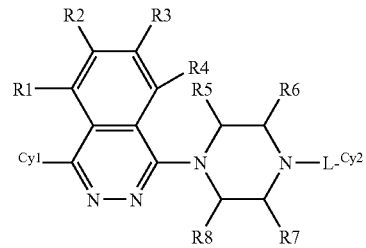

or a pharmaceutically acceptable salt thereof, wherein:

$Cy^1$ is a partially or fully saturated or unsaturated 3-8 membered monocyclic, or 6-12 membered bicyclic ring system, the ring system formed of carbon atoms optionally including 1-3 heteroatoms if monocyclic, or 1-6 heteroatoms if bicyclic, and wherein each ring of the ring system is optionally substituted independently with 1-5 substituents, wherein the substituents are selected from the group consisting of $C_{1-8}$alkyl, $C_{1-8}$alkenyl, $C_{1-8}$alkynyl, $C_{1-6}$haloalkyl, halogen, cyano, hydroxy, oxo, —$OR^c$, —$NR^aR^b$, $NR^aC(=O)R^b$, —$C(=O)OR^c$, —$R^cOC(=O)NR^aR^b$, —$R^cOH$, —$C(=O)NR^aR^b$, —$OC(=O)R^c$, —$NR^aC(=O)R^c$, —$NR^aS(=O)_mR^c$, —$S(=O)_mNR^aR^b$, and $S(=O)_mR^c$;

$R^1$, $R^2$, $R^3$, and $R^4$ are each independently selected from H, $C_{1-6}$alkyl, $C_{1-8}$alkenyl, $C_{1-6}$haloalkyl, halogen, cyano, nitro, —$OR^c$, —$NR^aR^b$, $NR^aC(=O)R^b$, —$C(=O)OR^c$, —$C(=O)NR^aR^b$, —$OC(=O)R^c$, —$NR^aC(=O)R^c$, —$NR^aS(=O)_mR^c$, —$S(=O)_mNR^aR^b$, and $S(=O)_mR^c$;

$R^5$, $R^6$, $R^7$, and $R^8$ are each independently selected from H, $C_{1-6}$alkyl, $C_{1-6}$haloalkyl, oxo, —$C(=O)OR^a$, —$R^cOH$, —$OR^c$, —$NR^aR^b$, $NR^aC(=O)R^b$, —$C(=O)OR^c$, —$C(=O)NR^aR^b$, —$OC(=O)R^c$, —$NR^aC(=O)R^c$, —$NR^aS(=O)_mR^c$, —$S(=O)_mNR^aR^b$, and $S(=O)_mR^c$, provided that at least one of $R^5$, $R^6$, $R^7$, and $R^8$ is not H;

$R^a$, $R^b$, and $R^c$ are each independently selected from H, $C_{1-8}$alkyl, $C_{1-8}$alkenyl, $C_{1-8}$alkynyl, $C_{1-6}$haloalkyl, heterocyclyl, aryl, and heteroaryl;

m is 1 or 2;

L is —$C(=O)$—, —$S(=O)_m$— or —$CH_2$—;

$Cy^2$ is a partially or fully saturated or unsaturated 3-8 membered monocyclic ring system, the ring system formed of carbon atoms optionally including 1-3 heteroatoms, and wherein the ring system is optionally substituted independently with 1-5 substituents, wherein the substituents are selected from the group consisting of $C_{1-8}$alkyl, $C_{1-8}$alkenyl, $C_{1-8}$alkynyl, $C_{1-6}$haloalkyl, halogen, cyano, hydroxy, oxo, —$C(=O)OR^c$, —$R^cOH$, —$OR^c$, —$NR^aR^b$, $NR^aC(=O)R^b$, —$C(=O)NR^aR^b$, —$OC(=O)R^c$, —$NR^aC(=O)R^c$, —$NR^aS(=O)_mR^c$, —$S(=O)_mNR^aR^b$, and $S(=O)_mR^c$.

In one aspect, $Cy^1$ can be aryl optionally substituted independently with 1-5 substituents. In another aspect, $Cy^1$ can be cycloalkyl optionally substituted independently with 1-5 substituents. In a further aspect, $Cy^1$ can be heteroaryl optionally substituted independently with 1-5 substituents. In another aspect, $Cy^1$ can be phenyl optionally substituted independently with 1-5 substituents. Further, for example, $Cy^1$ can be naphtyl, furanyl, benzopuranyl, thienyl, imidazolyl, triazolyl, quinoxalinyl, benzodioxolyl, benzodioxinyl, indolinyl, indolyl, indazolyl, benzoimidazolyl, benzoisoxazolyl, benzoxazolyl, benzothiazolyl, thiazolyl, oxazolyl, morpholinyl, pyridyl, pyrimidinyl, pyrrolidinyl, pyrazonyl, pyranyl, dihidropyranyl, tetrahydropyranyl, pyrazolyl, pyrrolyl, pipearazinyl, piperadinyl, pyridazinyl, phthalazinyl, azetidinyl, quinolinyl, quinazolinyl, dihydroquinolinyl, isoquinolinyl or cinnolinyl, any of which can be optionally substituted independently with 1-5 substituents. The substituents can be selected independently from the group consisting of $C_{1-8}$alkyl, $C_{1-8}$alkenyl, $C_{1-6}$haloalkyl, cyano, hydroxy and halogen.

In one aspect, $R^1$, $R^2$, $R^3$, and $R^4$ can be each independently selected from H, $C_{1-6}$alkyl, $C_{1-8}$alkenyl, $C_{1-6}$haloalkyl, and halogen. For example, $R^1$, $R^2$, $R^3$, and $R^4$ can be each independently selected from H and $C_{1-6}$alkyl. In one aspect, $R^1$, $R^2$, $R^3$, and $R^4$ may be each H. In another aspect, $R^5$, $R^6$, $R^7$, and $R^8$ can be each independently selected from H, $C_{1-6}$alkyl and $C_{1-6}$haloalkyl, provided that at least one of $R^5$, $R^6$, $R^7$, and $R^8$ is not H. For example, $R^5$, $R^6$, $R^7$ can be each H, and $R^8$ is $C_{1-6}$alkyl. For example, $R^8$ can be methyl. In another embodiment, $R^5$ and $R^7$ can be each H, and $R^6$ and $R^8$ are each independently $C_{1-6}$alkyl. In one example, $R^6$ and $R^8$ may be each methyl. In a further aspect, $R^5$, $R^6$, and $R^8$ can be each H, and $R^6$ is $C_{1-6}$alkyl. In another example, $R^5$, $R^6$, and $R^8$ can be each H, and $R^7$ can be $C_{1-6}$alkyl. In a further example, $R^6$, $R^7$, and $R^8$ can be each H, and $R^5$ can be $C_{1-6}$alkyl. In another example, $R^5$ and $R^7$ can be each independently $C_{1-6}$alkyl, and $R^6$ and $R^8$ can be each H.

The invention provides compounds of Formula I and pharmaceutically acceptable salts thereof, wherein L can be —C(=O)—. In another aspect, L can be —S(=O)$_2$—. In a further aspect, L can be —CH$_2$—.

The invention further provides compounds of Formula I and pharmaceutically acceptable salts thereof, wherein $Cy^2$ can be cycloalkyl or heterocycloalkyl, any of which can be optionally substituted independently with 1-5 substituents. In one aspect, cycloalkyl can be cyclopropyl, cyclobutyl, cyclopentyl, cyclohexyl, or cycloheptyl, any of which can be optionally substituted independently with 1-5 substituents. In one aspect, $Cy^2$ can be aryl or heteroaryl, any of which can be optionally substituted independently with 1-5 substituents. For example, aryl can be phenyl optionally substituted independently with 1-5 substituents. The substituents can be selected from the group consisting of $C_{1-8}$alkyl, $C_{1-6}$haloalkyl, halogen, cyano, hydroxyl and oxo.

The invention further provides compounds of Formula I selected from:
(2-methyl-4-(4-phenyl-phthalazin-1-yl)piperazin-1-yl)-(thiophen-2-yl)-methanone,
(2-methyl-4-(4-phenylphthalazin-1-yl)piperazin-1-yl)(phenyl)methanone,
phenyl(5-(4-phenylphthalazin-1-yl)-2,5-diaza-bicyclo[2.2.1]-heptan-2-yl)-methanone,
(3-methyl-4-(4-phenylphthalazin-1-yl)piperazin-1-yl)(phenyl)methanone,
(2-methyl-4-(4-phenylphthalazin-1-yl)piperazin-1-yl)(phenyl)-methanone,
(4-(4-(4-chlorophenyl)phthalazin-1-yl)-2-methylpiperazin-1-yl)(phenyl)methanone,
(2-methyl-4-(4-p-tolylphthalazin-1-yl)piperazin-1-yl)(phenyl)methanone,
4-(4-(3,4-dichlorophenyl)-phthalazin-1-yl)-2-methylpiperazin-1-yl)(phenyl)-methanone,
(3-methyl-4-(4-phenylphthalazin-1-yl)piperazin-1-yl)(phenyl)-methanone,
2,6-dimethyl-4-(4-phenylphthalazin-1-yl)piperazin-1-yl)(phenyl)-methanone,
(2-methyl-4-(4-phenylphthalazin-1-yl)piperazin-1-yl)(pyridin-3-yl)methanone,
(2-methyl-4-(4-phenylphthalazin-1-yl)piperazin-1-yl)(pyridin-4-yl)methanone,
(2-methyl-4-(4-phenylphthalazin-1-yl)piperazin-1-yl)(thiazol-2-yl)methanone,
cyclopentyl(3-methyl-4-(4-phenylphthalazin-1-yl)piperazin-1-yl)methanone,
cyclopropyl(3-methyl-4-(4-phenylphthalazin-1-yl)piperazin-1-yl)methanone,
cyclohexyl(3-methyl-4-(4-phenylphthalazin-1-yl)piperazin-1-yl)methanone,
2-methyl-4-(4-(pyridin-2-yl)phthalazin-1-yl)piperazin-1-yl)(phenyl)methanone,
3-methyl-4-(4-(pyridin-2-yl)phthalazin-1-yl)piperazin-1-yl)(phenyl)methanone,
(3-methyl-4-(4-p-tolylphthalazin-1-yl)piperazin-1-yl)(phenyl)-methanone,
(4-(4-(4-chlorophenyl)-phthalazin-1-yl)-3-methylpiperazin-1-yl)(phenyl)-methanone,
(4-(4-(4-tert-butylphenyl)-phthalazin-1-yl)-3-methyl-piperazin-1-yl)(phenyl)-methanone,
(3-methyl-4-(4-(4-(trifluoromethyl)-phenyl)-phthalazin-1-yl)piperazin-1-yl)(phenyl)-methanone,
(4-(4-(4-isopropylphenyl)-phthalazin-1-yl)-3-methylpiperazin-1-yl)(phenyl)-methanone,
4-(4-(benzofuran-2-yl)phthalazin-1-yl)-3-methylpiperazin-1-yl)(phenyl)-methanone,
4-(4-(benzofuran-2-yl)phthalazin-1-yl)-3-methylpiperazin-1-yl)(phenyl)-methanone,
(2,5-dimethyl-4-(4-phenylphthalazin-1-yl)piperazin-1-yl)(phenyl)methanone,
(2,5-dimethyl-4-(4-phenylphthalazin-1-yl)piperazin-1-yl)(phenyl)methanone,
2,5-dimethyl-4-(4-(4-(trifluoromethyl)-phenyl)-phthalazin-1-yl)piperazin-1-yl)(phenyl)methanone,
(2-methyl-4-(4-(4-(trifluoromethyl)phenyl)phthalazin-1-yl)piperazin-1-yl)(phenyl)methanone,
(2-methyl-4-(4-(4-vinylphenyl)phthalazin-1-yl)piperazin-1-yl)(phenyl)methanone,
4-(4-(2-fluoro-4-methylphenyl)phthalazin-1-yl)-2-methylpiperazin-1-yl)(phenyl)methanone,
4-(4-(3-fluoro-4-methylphenyl)phthalazin-1-yl)-2-methylpiperazin-1-yl)(phenyl)methanone,
4-(4-(2-fluorophenyl)phthalazin-1-yl)-2-methylpiperazin-1-yl)(phenyl)methanone,
4-(4-(2-fluoro-4-methylphenyl)phthalazin-1-yl)-3-methylpiperazin-1-yl)(phenyl)methanone,
4-(4-(3-fluoro-4-methylphenyl)phthalazin-1-yl)-3-methylpiperazin-1-yl)(phenyl)methanone,
4-(4-(4-chloro-2-fluorophenyl)phthalazin-1-yl)-3-methylpiperazin-1-yl)(phenyl)methanone,
4-(4-(4-chloro-2-fluorophenyl)phthalazin-1-yl)-2-methylpiperazin-1-yl)(phenyl)methanone,
4-(4-(2-fluorophenyl)phthalazin-1-yl)-3-methylpiperazin-1-yl)(phenyl)methanone,
1-benzyl-4-(4-(4-(trifluoromethyl)phenyl)phthalazin-1-yl)piperazin-2-one,
(4-(4-(4-fluorophenyl)phthalazin-1-yl)-3-methylpiperazin-1-yl)(phenyl)methanone,
methyl 4-(4-(4-benzoyl-2-methylpiperazin-1-yl)phthalazin-1-yl)benzoate,
(4-(4-(4-(dimethylamino)phenyl)phthalazin-1-yl)-3-methylpiperazin-1-yl)(phenyl)methanone,
methyl 1-benzoyl-4-(4-phenylphthalazin-1-yl)piperazine-2-carboxylate,
2,5-dimethyl-4-(4-phenylphthalazin-1-yl)piperazin-1-yl)(phenyl)methanone,
4-(4-(4-benzoyl-2-methylpiperazin-1-yl)phthalazin-1-yl)benzonitrile,
(4-(4-(4-(hydroxymethyl)phenyl)phthalazin-1-yl)-3-methylpiperazin-1-yl)(phenyl)methanone, (3-methyl-4-(4-(4-morpholinophenyl)phthalazin-1-yl)piper-
azin-1-yl)(phenyl)methanone,
(4-(4-(4-hydroxyphenyl)phthalazin-1-yl)-3-methylpiper-
azin-1-yl)(phenyl)methanone,
cyclohexyl(4-(4-(4-fluorophenyl)phthalazin-1-yl)-3-meth-
ylpiperazin-1-yl)methanone,
(3-methyl-4-(7-nitro-4-phenylphthalazin-1-yl)piperazin-1-
yl)(phenyl)methanone,
(3-methyl-4-(6-nitro-4-phenylphthalazin-1-yl)piperazin-1-
yl)(phenyl)methanone,
cyclohexyl(4-(4-(4-(hydroxymethyl)phenyl)phthalazin-1-
yl)-3-methylpiperazin-1-yl)methanone,
(4-(7-fluoro-4-phenylphthalazin-1-yl)-3-methylpiperazin-1-
yl)(phenyl)methanone,
(4-(6-fluoro-4-phenylphthalazin-1-yl)-3-methylpiperazin-1-
yl)(phenyl)methanone,
(4-(6-fluoro-4-phenylphthalazin-1-yl)-2-methylpiperazin-1-
yl)(phenyl)methanone,
(4-(4-cyclopropylphthalazin-1-yl)-2-methylpiperazin-1-yl)
(phenyl)methanone,
(2-methyl-4-(4-(pyridin-4-yl)phthalazin-1-yl)piperazin-1-
yl)(phenyl)methanone,
(3-methyl-4-(4-(pyridin-4-yl)phthalazin-1-yl)piperazin-1-
yl)(phenyl)methanone,
(4-(4-(4-(hydroxymethyl)phenyl)phthalazin-1-yl)-2,5-dim-
ethylpiperazin-1-yl)(phenyl)methanone,
(4-(4-(4-(hydroxymethyl)phenyl)phthalazin-1-yl)-2,5-dim-
ethylpiperazin-1-yl)(phenyl)methanone,
(4-(4-(4-chloro-2-fluorophenyl)phthalazin-1-yl)-2,5-dim-
ethylpiperazin-1-yl)(phenyl)methanone,
(4-(4-(4-chloro-2-fluorophenyl)phthalazin-1-yl)-2,5-dim-
ethylpiperazin-1-yl)(phenyl)methanone,
(2,2-dimethyl-4-(4-phenylphthalazin-1-yl)piperazin-1-yl)
(phenyl)methanone,
4-(4-(4-(4,4-difluorocyclohexanecarbonyl)-2-methylpiper-
azin-1-yl)phthalazin-1-yl)benzonitrile,
(3-methyl-4-(4-morpholinophthalazin-1-yl)piperazin-1-yl)
(phenyl)methanone,
1-(3-methyl-4-(phenylsulfonyl)piperazin-1-yl)-4-phe-
nylphthalazine,
1-(2-methyl-4-(phenylsulfonyl)piperazin-1-yl)-4-phe-
nylphthalazine,
4-(2-methyl-1-(4-phenylphthalazin-1-yl)piperazine-4-car-
bonyl)cyclohexanone,
3-(2-methyl-1-(4-phenylphthalazin-1-yl)piperazine-4-car-
bonyl)cyclohexanone,
4-(4-(4-benzoyl-2-methylpiperazin-1-yl)phthalazin-1-yl)
benzamide,
4-(4-(4-(cyclohexanecarbonyl)-2-methylpiperazin-1-yl)ph-
thalazin-1-yl)benzonitrile,
2-methyl-4-(4-(pyridin-3-yl)phthalazin-1-yl)piperazin-1-yl)
(phenyl)methanone,
3-methyl-4-(4-(pyridin-3-yl)phthalazin-1-yl)piperazin-1-yl)
(phenyl)methanone,
4-(4-(4-benzoyl-2,5-dimethylpiperazin-1-yl)phthalazin-1-
yl)benzonitrile,
4-(4-(4-benzoyl-2,5-dimethylpiperazin-1-yl)phthalazin-1-
yl)benzonitrile,
4-(4-(1H-imidazol-1-yl)phthalazin-1-yl)-2-methylpiper-
azin-1-yl)(phenyl)methanone, 4-(4-(1H-pyrazol-1-yl)phthalazin-1-yl)-3-methylpiperazin-
1-yl)(phenyl)methanone,
4-(4-(1H-indol-1-yl)phthalazin-1-yl)-3-methylpiperazin-1-
yl)(phenyl)methanone,
4-(4-(1H-pyrrol-1-yl)phthalazin-1-yl)-3-methylpiperazin-1-
yl)(phenyl)methanone,
(4-(4-(4-benzoyl-2-methylpiperazin-1-yl)phthalazin-1-yl)
phenyl)methyl carbamate,
(4-(4-(4-(cyclohexanecarbonyl)-2-methylpiperazin-1-yl)ph-
thalazin-1-yl)phenyl)methyl carbamate,
3-methyl-4-(4-(4-(2-(tetrahydro-2H-pyran-2-yloxy)ethyl)
phenyl)phthalazin-1-yl)piperazin-1-yl)(phenyl)metha-
none, and
4-(4-(4-(2-hydroxyethyl)phenyl)phthalazin-1-yl)-3-meth-
ylpiperazin-1-yl)(phenyl)methanone,
or a stereoisomer or a pharmaceutically acceptable salt
thereof.

A. Preparation of Compounds

The present invention comprises processes for the preparation of a compound of Formula I.

Methods A-K below provide exemplary synthetic schemes for the preparation of the compounds of the present invention. One of skill in the art will understand that additional methods are also useful. In other words, the compounds of the invention can be made using organic synthesis using starting materials, reagents and reactions well known in the art.

Certain compounds of the invention may be conveniently prepared by a general process outlined in Method A.

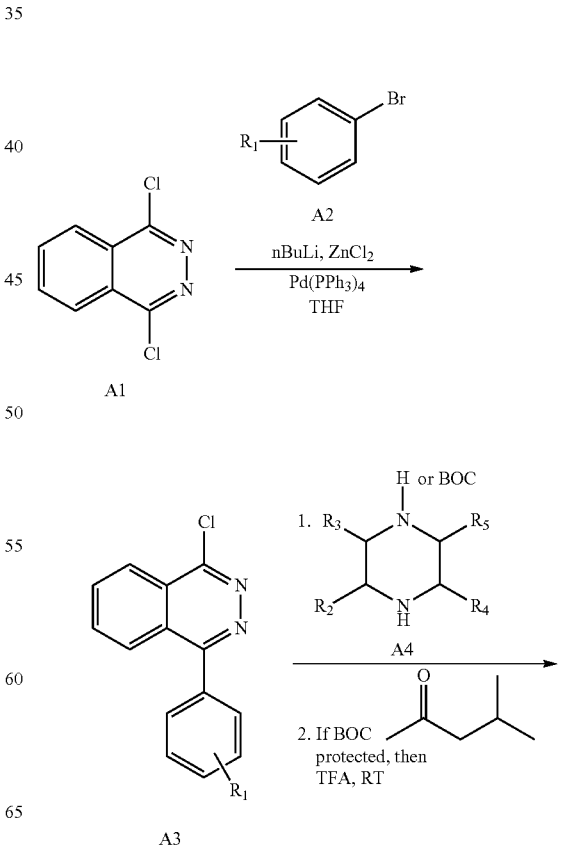

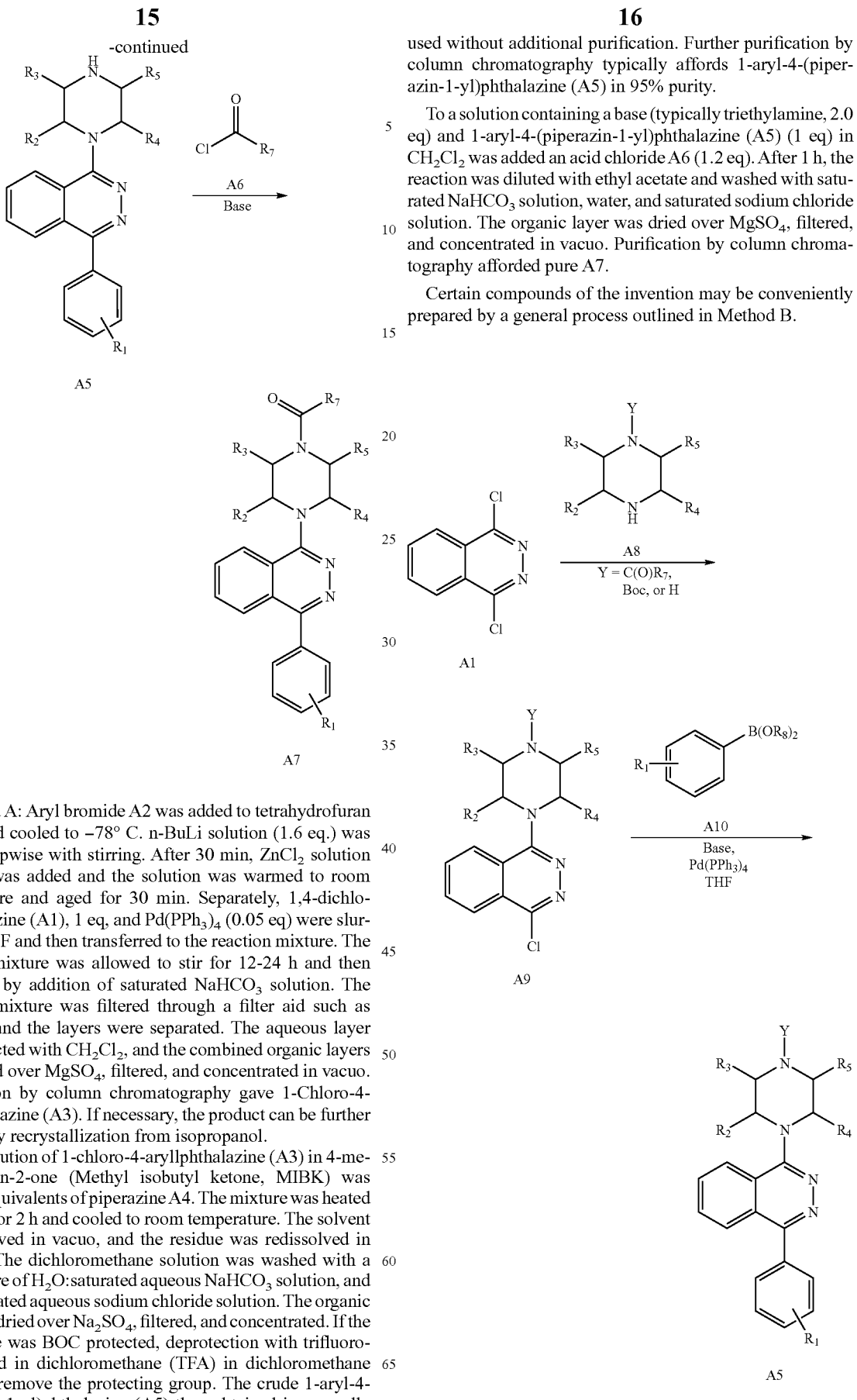

Method A: Aryl bromide A2 was added to tetrahydrofuran (THF) and cooled to −78° C. n-BuLi solution (1.6 eq.) was added dropwise with stirring. After 30 min, ZnCl$_2$ solution (1.6 eq) was added and the solution was warmed to room temperature and aged for 30 min. Separately, 1,4-dichlorophthalazine (A1), 1 eq, and Pd(PPh$_3$)$_4$ (0.05 eq) were slurried in THF and then transferred to the reaction mixture. The reaction mixture was allowed to stir for 12-24 h and then quenched by addition of saturated NaHCO$_3$ solution. The biphasic mixture was filtered through a filter aid such as Celite®, and the layers were separated. The aqueous layer was extracted with CH$_2$Cl$_2$, and the combined organic layers were dried over MgSO$_4$, filtered, and concentrated in vacuo. Purification by column chromatography gave 1-Chloro-4-arylphthalazine (A3). If necessary, the product can be further purified by recrystallization from isopropanol.

To a solution of 1-chloro-4-aryllphthalazine (A3) in 4-methyl-pentan-2-one (Methyl isobutyl ketone, MIBK) was added 6 equivalents of piperazine A4. The mixture was heated to reflux for 2 h and cooled to room temperature. The solvent was removed in vacuo, and the residue was redissolved in CH$_2$Cl$_2$. The dichloromethane solution was washed with a 1:1 mixture of H$_2$O:saturated aqueous NaHCO$_3$ solution, and then saturated aqueous sodium chloride solution. The organic layer was dried over Na$_2$SO$_4$, filtered, and concentrated. If the piperazine was BOC protected, deprotection with trifluoroacetic acid in dichloromethane (TFA) in dichloromethane serves to remove the protecting group. The crude 1-aryl-4-(piperazin-1-yl)phthalazine (A5) thus obtained is generally used without additional purification. Further purification by column chromatography typically affords 1-aryl-4-(piperazin-1-yl)phthalazine (A5) in 95% purity.

To a solution containing a base (typically triethylamine, 2.0 eq) and 1-aryl-4-(piperazin-1-yl)phthalazine (A5) (1 eq) in CH$_2$Cl$_2$ was added an acid chloride A6 (1.2 eq). After 1 h, the reaction was diluted with ethyl acetate and washed with saturated NaHCO$_3$ solution, water, and saturated sodium chloride solution. The organic layer was dried over MgSO$_4$, filtered, and concentrated in vacuo. Purification by column chromatography afforded pure A7.

Certain compounds of the invention may be conveniently prepared by a general process outlined in Method B.

-continued

When Y = C(O)R$_7$, then A5 = A7,
When Y = Boc, then TFA/CH$_2$Cl$_2$
gives Y = H.
When Y = H,

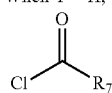

| Base ↓

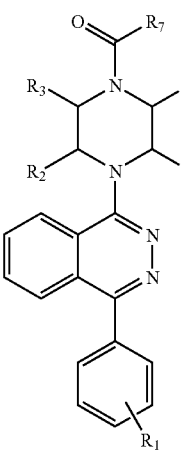

A7

Some compounds of the invention may be prepared by a general process outlined in Method C.

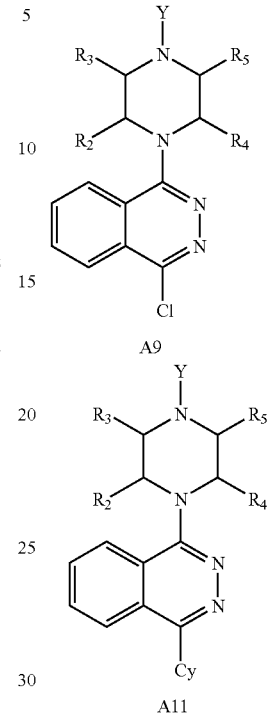

A9

$\xrightarrow[\text{Toluene}]{\underset{\text{Pd(PPh}_3)_4}{\text{Cy-SnBu}_3}}$

When Y = C(O)R$_7$, then A11 = A12,
When Y = BOC, then TFA/CH$_2$Cl$_2$
gives Y = H.
When Y = H,

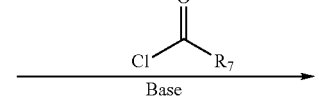

A11

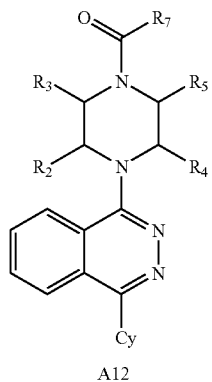

A12

Method B: Dichlorophthalazine A1 (1 eq) was added to a reaction vessel containing 2-4 equivalents of piperazine A8 (where Y=H, Boc, or C(O)R$_7$). The reaction may be run neat, or in the presence of a suitable solvent such as DMF, NMP, MEK, or MIBK. The reaction was stirred at a temperature of between 20 to 150° C. until significant completion by TLC or LC/MS was determined. The crude reaction mixture was dissolved in dichloromethane and washed with saturated NaHCO$_3$ solution and saturated NaCl solution. The organic layer was dried over MgSO$_4$, filtered, and concentrated. Purification by column chromatography afforded A9.

To a round bottomed flask containing A9 was added 0.05 equivalents of Pd(PPh$_3$)$_4$, 1.5 equivalents of a boronic acid (R$_8$=H) or boronic acid ester (R$_8$=alkyl) A10, and 2 equivalents of a base such as Na$_2$CO$_3$ or K$_3$PO$_4$. The vessel was purged with an inert atmosphere. The reaction was diluted with 10 parts toluene and 1 part water to afford a reaction concentration of ~0.1 M. The reaction was heated to 100° C. until reaction completion as determined by TLC or LC/MS. The cooled reaction mixture was diluted with ethyl acetate and washed with saturated NaHCO$_3$ solution and saturated NaCl solution. The organic layer was dried over MgSO$_4$, filtered, and concentrated. Purification by column chromatography afforded A5. When Y=C(O)R$_7$, A5=final product A7. When compound A5 has Y=Boc, deprotection to Y=H is accomplished by treatment with TFA in dichloromethane, followed by quenching into saturated NaHCO$_3$ solution and extraction with dichloromethane. The organic layer was dried over MgSO$_4$, filtered, and concentrated to afford A5, Y=H. Compound A5 was transformed to A7 as described in method A.

Method C: compound A9 was added to a reaction vessel along with Cy—SnBu$_3$ (1.5 eq.) and Pd(PPh$_3$)$_4$ (0.05 eq.). The reaction vessel was purged with nitrogen, and toluene was added. The reaction was heated to 100° C. for a period of 12-24 hours, or until judged to be complete by TLC or LC/MS analysis. The reaction was cooled to room temperature and stirred with saturated aqueous KF for 1 h, diluted with water (10 mL) and extracted with 10% MeOH in CH$_2$Cl$_2$ (3×30 mL). The combined organics were dried with Na$_2$SO$_4$ and concentrated in vacuo. Purification by column chromatography afforded A11. When Y=C(O)R$_7$, A11=final product A12. When compound A11 has Y=Boc, deprotection to Y=H is accomplished by treatment with TFA in dichloromethane, followed by quenching into saturated NaHCO$_3$ solution and extraction with dichloromethane. The organic layer was dried over MgSO$_4$, filtered, and concentrated to afford A11, Y=H.

Compound A11 (Y=H) was dissolved in dichloromethane. Addition of a suitable base (typically triethylamine, 2 equivalents) was followed by addition of an acid chloride ($R_7C(O)Cl$). The reaction was stirred until judged to be complete by TLC or LC/MS analysis. The reaction was diluted with ethyl acetate, and washed with saturated $NaHCO_3$ solution and saturated NaCl solution. The organic layer was dried over $MgSO_4$, filtered, and concentrated. Purification by column chromatography (typically 70:30 ethyl acetate:hexanes) afforded A12.

Certain compounds of the invention may be conveniently prepared by a general process outlined in Method D.

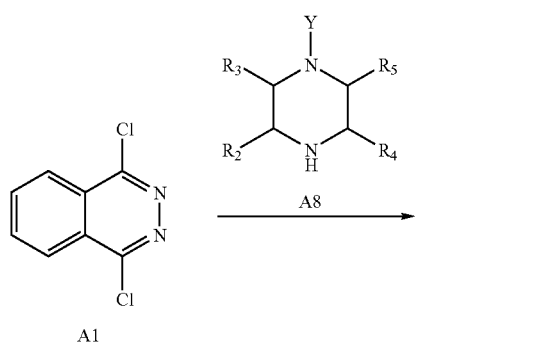

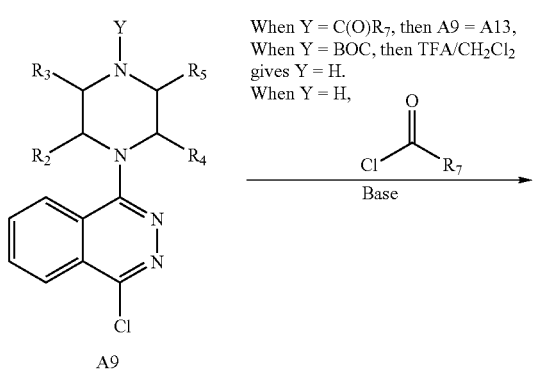

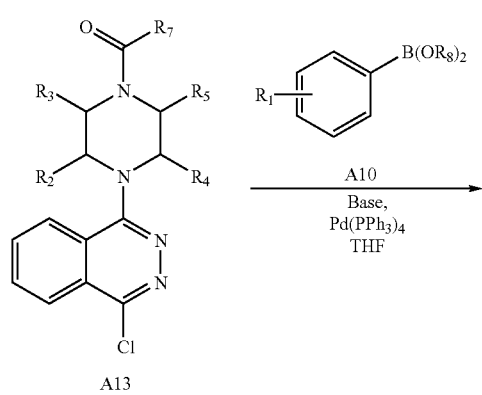

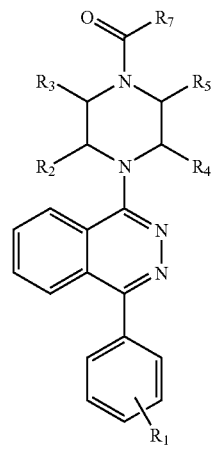

Method D: the piperazinyl phthalazine A9 was obtained as described in Method B above. If the group Y of A9 was an amide $C(O)R_7$, no acylation reaction was necessary to generate A13. If compound A9 has Y=Boc, deprotection to Y=H is accomplished by treatment with trifluoroacetic acid in dichloromethane, followed by quenching into saturated $NaHCO_3$ solution and extraction with dichloromethane. The organic layer was dried over $MgSO_4$, filtered, and concentrated to afford A9, Y=H.

Amine A9 (Y=H) was dissolved in dichloromethane. Addition of a suitable base (typically triethylamine, 2 equivalents) was followed by addition of an acid chloride ($R_7C(O)Cl$, 1-2 equivalents). The reaction was stirred until judged to be complete by TLC or LC/MS analysis. The reaction was diluted with ethyl acetate, and washed with saturated $NaHCO_3$ solution and saturated NaCl solution. The organic layer was dried over $MgSO_4$, filtered, and concentrated. Purification by column chromatography afforded A13.

To a round bottomed flask containing A13 was added 0.05 equivalents of $Pd(PPh_3)_4$, 1.5 equivalents of a boronic acid ($R_8$=H) or boronic acid ester ($R_8$=alkyl) A10, and 2 equivalents of a base such as $Na_2CO_3$ or $K_3PO_4$. The vessel was purged with an inert atmosphere. The reaction was diluted with 10 parts toluene and 1 part water to afford a reaction concentration of ~0.1 M. The reaction was heated to 100° C. until reaction completion as determined by TLC or LC/MS. The cooled reaction mixture was diluted with ethyl acetate and washed with saturated $NaHCO_3$ solution and saturated NaCl solution. The organic layer was dried over $MgSO_4$, filtered, and concentrated. Purification by column chromatography afforded A7.

Certain compounds of the invention may be prepared by a general process outlined in Method E.

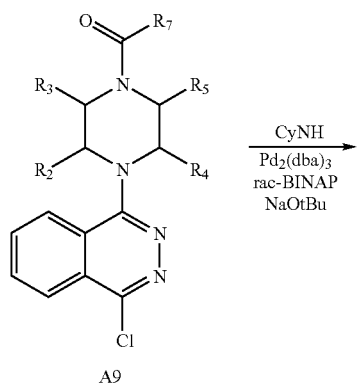

A9

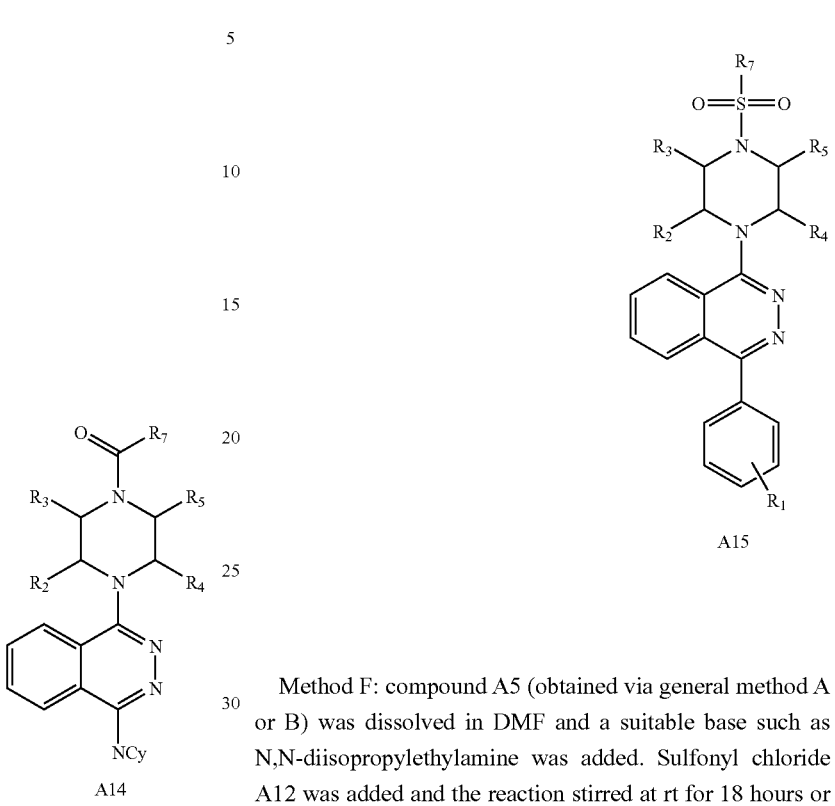

Method E: to a reaction vial was added A9, sodium t-butoxide (1.4 eq), rac-BINAP (0.04 eq), Pd$_2$(dba)$_3$ (0.02 eq) and a cyclic secondary amine (CyNH, 4 eq). The reaction vessel was purged with argon and heated to 80° C. for 16 h, after which time the reaction was taken up in dichloromethane, and directly loaded onto silica gel. Purification by column chromatography afforded the desired product A14.

Some compounds of the invention may be conveniently prepared by a general process outlined in Method F.

Method F: compound A5 (obtained via general method A or B) was dissolved in DMF and a suitable base such as N,N-diisopropylethylamine was added. Sulfonyl chloride A12 was added and the reaction stirred at rt for 18 hours or until judged to be complete by TLC or LC/MS analysis. The reaction was taken up in ethyl acetate washed with aqueous K$_2$CO$_3$ (10%), water, and then saturated sodium chloride. The organics were dried (MgSO$_4$) and evaporated. Chromatography over silica gel afforded sulfonamide A15.

Some compounds of the invention may also be prepared by a general process outlined in Method G.

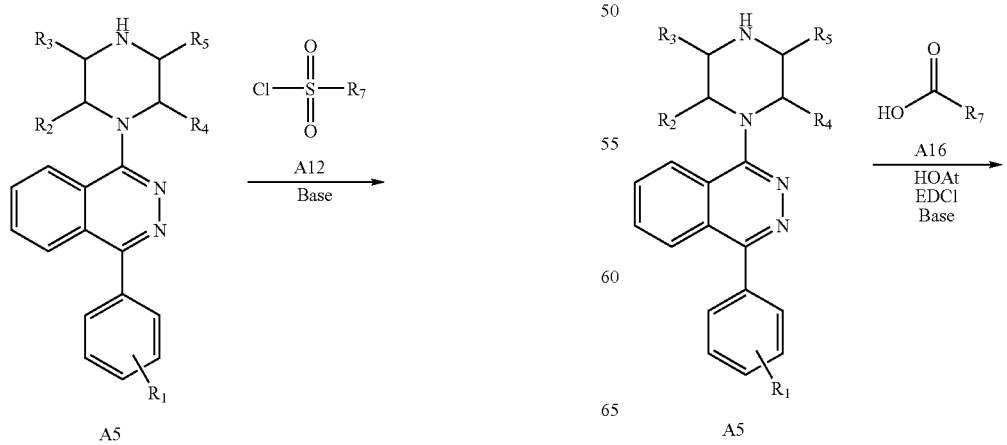

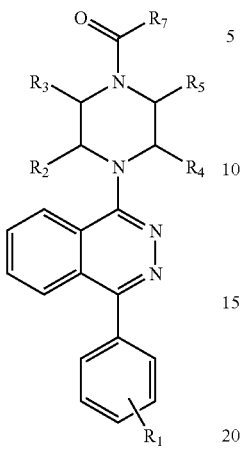

A7

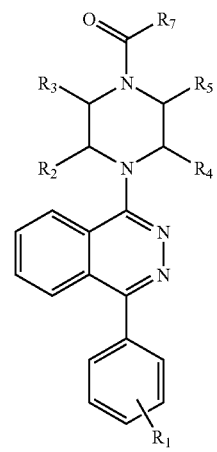

A7

Method G: compound A5 (obtained via general method A or B), carboxylic acid A16, 3H-[1,2,3]triazolo[4,5-b]pyridin-3-ol (HOAT), N1-((ethylimino)methylene)-N3,N3-dimethylpropane-1,3-diamine hydrochloride (EDCI), and sodium bicarbonate were dissolved in DMF were stirred at rt for 22 hours or until judged to be complete by TLC or LC/MS. The reaction was taken up in ethyl acetate, washed with aqueous $K_2CO_3$ (10%), water, and then saturated sodium chloride. The organics were dried ($MgSO_4$) and evaporated. Chromatography over silica gel gave A7.

Other compounds of the invention may also be prepared by a general process outlined in Method H:

Method H: a Schlenk tube was charged with A9, a boronic acid or boronic acid ester, tris(dibenzylideneacetone)dipalladium (0) (0.01 eq), dicyclohexyl(2,6-dimethoxyphenyl)phosphine (0.02 eq), and potassium phosphate tribasic (2 eq.). The vessel was evacuated and backfilled with argon, then previously degassed n-butanol was added. The reaction was heated at 100° C. for 20 hours or until TLC or LC/MS indicated that the reaction was complete. After cooling, the reaction was added to aqueous $K_2CO_3$ (10%) and extracted three times with dichloromethane. The combined organics were dried ($MgSO_4$) and evaporated. Chromatography over silica gel with a gradient of hexanes/0-100% ethyl acetate gave product A7.

Some compounds of the invention can be prepared by a process outlined in Method I:

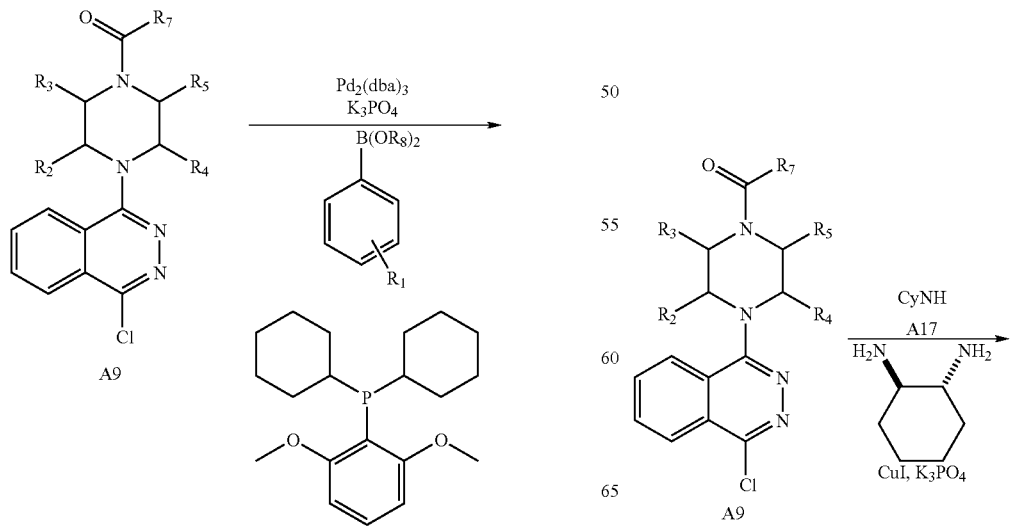

-continued

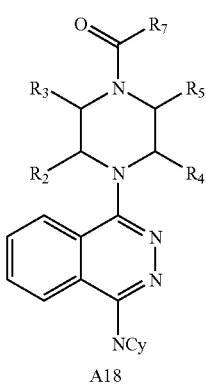

A18

Method I: a reaction vessel was charged with A9, a cyclic amine CyNH (A17) (1.2 eq), copper (I) iodide (0.05 eq), potassium phosphate (2.1 eq), trans-cyclohexanediamine (0.1 eq), and dioxane. The vessel was evacuated and backfilled with argon, then heated at 110° C. for 22 hours. After cooling, the reaction was then taken up in ethyl acetate washed with aqueous $K_2CO_3$ (10%), water, and saturated sodium chloride. The organics were dried ($MgSO_4$) and evaporated. Chromatography over silica gel gave A18.

Some compounds of the invention can be prepared by a process outlined in Method J:

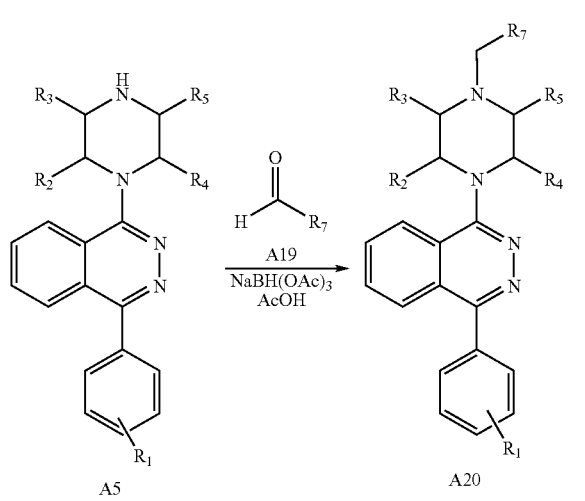

Method J: compound A5 (143 mg, 0.492 mmol), an aldehyde A19 (1.25 eq), sodium triacetoxyborohydride (1.5 eq), and acetic acid (1.2 eq), were dissolved in acetonitrile and stirred at rt for 17 h or until the reaction was judged to be complete by TLC or LC/MS. The reaction was taken up in ethyl acetate, washed with aqueous $K_2CO_3$ (10%), water, and then saturated sodium chloride. The organics were dried ($MgSO_4$) and evaporated. Chromatography over silica gel gave A20.

Certain compounds of the invention can be prepared by a process outlined in Method K:

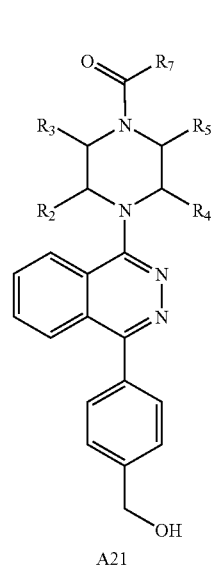

A21

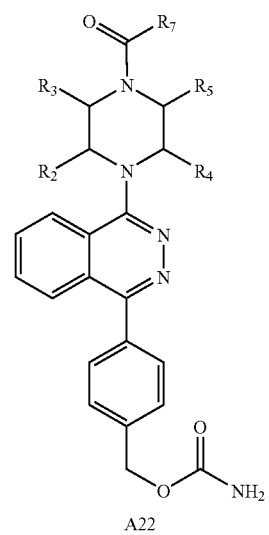

A22

Method K: primary alcohol containing compound A21 was dissolved in chloroform. 2,2,2-trichloroacetyl isocyanate (1.2 eq) was added and the reaction stirred at rt for 80 minutes. The reaction was adsorbed onto alumina (Brockmann II) and after 2 hours was eluted with 10% methanol in dichloromethane. The resulting solution was evaporated. Chromatography over silica gel with a gradient of hexanes/0-45% ethyl acetate gave primary carbamate A22.

B. Pharmaceutical Compositions and Administration

Compounds useful in the present invention can be used in the form of pharmaceutically acceptable salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, mandelate, methansulfonate, nicotinate, 2-naphthalenesulfonate, oxalate, palmoate, pectinate, persulfate, 2-phenylpropionate, picrate, pivalate, propionate, salicylate, succinate, sulfate, tartrate, thiocyanate, tosylate, mesylate, and undecanoate. When compounds of the invention include an acidic function such as a carboxy group, then suitable pharmaceutically acceptable salts for the carboxy group are well known to those skilled in the art and include, for example, alkaline, alkaline earth, ammonium, quaternary ammonium cations and the like. For additional examples of "pharmacologically acceptable salts," see infra and Berge et al. *J. Pharm. Sci.* 66: 1, 1977. In certain embodiments of the invention salts of hydrochloride and salts of methanesulfonic acid can be used.

For administration, the compounds useful in this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds useful in this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

The therapeutically effective amount of the smoothed receptor modulator in the compositions useful in the invention can range from about 0.1 mg to about 180 mg, for example from about 5 mg to about 180 mg, or from about 1 mg to about 100 mg of the smoothened antagonist per subject. In some aspects, the therapeutically effective amount of the compound in the composition can be chosen from about 0.1 mg, about 1 mg, 5 mg, about 15 mg, about 20 mg, about 30 mg, about 50 mg, about 60 mg, about 75 mg, about 90 mg, about 120 mg, about 150 mg, about 180 mg.

While it may be possible to administer a compound of the invention to a subject alone, the compound administered will normally be present as an active ingredient in a pharmaceutical composition. Thus, a pharmaceutical composition of the invention may comprise a therapeutically effective amount of at least one smoothed receptor modulator compound, or an effective dosage amount of at least one smoothed receptor modulator compound.

As used herein, an "effective dosage amount" is an amount that provides a therapeutically effective amount of the smoothened antagonist when provided as a single dose, in multiple doses, or as a partial dose. Thus, an effective dosage amount of the smoothened antagonist of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the smoothed receptor modulator compound is administered by administering a portion of the composition.

Alternatively, a pharmaceutical composition in which two or more unit dosages, such as in tablets, capsules and the like, are required to administer an effective amount of the smoothed receptor modulator may be administered in less than an effective amount for one or more periods of time (e.g., a once-a-day administration, and a twice-a-day administration), for example to ascertain the effective dose for an individual subject, to desensitize an individual subject to potential side effects, to permit effective dosing readjustment or depletion of one or more other therapeutics administered to an individual subject, and/or the like.

The effective dosage amount of the pharmaceutical composition useful in the invention can range from about 1 mg to about 360 mg from a unit dosage form, for example about 5 mg, about 15 mg, about 30 mg, about 50 mg, about 60 mg, about 75 mg, about 90 mg, about 120 mg, about 150 mg, about 180 mg, about 210 mg, about 240 mg, about 300 mg, or about 360 mg from a unit dosage form.

III. Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "combination therapy", in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration;

compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents, which may be used in combination with compounds of the present invention, consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents, which may be used in combination with compounds of the present invention, consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), VECTIBIX™ (panitumumab), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aetema, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors and CDK inhibitors, TNF inhibitors, metallomatrix proteases inhibitors (MMP), COX-2 inhibitors including celecoxib, NSAID's, or $\alpha_v\beta_3$ inhibitors.

IV. Therapeutic Uses of the Compounds of the Invention

Compounds and compositions of the present application may thus be used, in one aspect, for the treatment or prevention of angiogenesis related diseases. "Angiogenesis" refers to any alteration of an existing vascular bed or the formation of new vasculature, which benefits tissue perfasion. This includes the formation of new vessels by sprouting of endothelial cells from existing blood vessels or the remodelling of existing vessels to alter size, maturity, direction or flow properties to improve blood perfusion of tissue.

Hh is known to stimulate angiogenesis. It has been demonstrated that Matrigel plugs impregnated with hedgehog protein and inserted into mice evince substantial neovascularization, whereas Matrigel plugs not carrying hedgehog show comparatively little vascularization. Hedgehog protein is also capable of increasing vascularization of the normally avascular mouse cornea. The PTCH1 gene is expressed in normal vascular tissues, including the endothelial cells of the aorta, vascular smooth muscle cells, adventitial fibroblasts of the aorta, the coronary vasculature and cardiomyocytes of the atria and ventricles. These tissues are also sensitive to hedgehog protein. Treatment with exogenous hedgehog causes upregulation of PTCH1 expression. In addition, hedgehog proteins have been shown to stimulate proliferation of vascular smooth muscle cells in vivo. Hedgehog proteins also cause fibroblasts to increase expression of angiogenic growth factors such as VEGF, bFGF, Ang-1 and Ang-2. Lastly, hedgehog proteins are known to stimulate recovery from ischemic injury and stimulate formation of collateral vessels. Given that Hh promotes angiogenesis, antagonists of Hh pathway, such as SMO antagonists of the present invention are useful as angiogenesis inhibitors, particularly in situations where some level of hedgehog signaling is necessary for angiogenesis.

Angiogenesis is fundamental to many disorders. Persistent, unregulated angiogenesis occurs in a range of disease states, tumor metastases and abnormal growths by endothelial cells. The vasculature created as a result of angiogenic processes supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

The compounds and compositions of the current invention can be used to treat diseases supported by or associated with angiogenesis. These diseases include ocular neovascular disease, age-related macular degeneration, diabetic retinopathy, retinopathy of prematurity, corneal graft rejection, neovascular glaucoma, retrolental fibroplasia, epidemnic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, corneal graph rejection, rheumatoid arthritis, osteoarthritis chronic inflammation (e.g., ulcerative colitis or Crohn's disease), hemangioma, Osler-Weber-Rendu disease, and hereditary hemorrhagic telangiectasia.

In addition, angiogenesis plays a critical role in cancer. A tumor cannot expand without a blood supply to provide nutrients and remove cellular wastes. Tumors in which angiogenesis is important include solid tumors such as rhabdomyosarcomas, retinoblastoma, Ewing sarcoma, neuroblastoma, and osteosarcoma, and benign tumors such as acoustic neuroma, neurofibroma, trachoma and pyogenic granulomas. Angiogenic factors have been found associated with several solid tumors. Prevention of angiogenesis could halt the growth of these tumors and the resultant damage to the animal due to the presence of the tumor. Angiogenesis is also associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

In addition to tumor growth, angiogenesis is important in metastasis. Initially, angiogenesis is important in the vascularization of the tumor which allows cancerous cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

It is further contemplated that the use of the smoothened antagonists of the present invention may be specifically targeted to disorders where the affected tissue and/or cells evince high Hh pathway activation. Expression of GLI genes is activated by the hedgehog signaling pathway, including GLI-1, GLI-2 and GLI-3. GLI-1 expression is most consistently correlated with hedgehog signaling activity across a wide range of tissues and disorders, while GLI-3 is somewhat less so. The GLI genes encode transcription factors that activate expression of many genes needed to elicit the full effects of Hh signaling. However, the GLI-3 transcription factor can also act as a repressor of hedgehog effector genes, and therefore, expression of GLI-3 can cause a decreased effect of the hedgehog signaling pathway. Whether GLI-3 acts as a transcriptional activator or repressor depends on post-translational events, and therefore it is expected that methods for detecting the activating form (versus the repressing form) of GLI-3 protein would also be a reliable measure of hedgehog pathway activation. GLI-2 gene expression is expected to provide a reliable marker for Hh pathway activation. The GLI-1 gene is strongly expressed in a wide array of cancers, hyperplasias and immature lungs, and serves as a marker for the relative activation of the hedgehog pathway. In addition, tissues, such as immature lung, that have high GLI gene expression are strongly affected by hedgehog inhibitors. Accordingly, it is contemplated that the detection of GLI gene expression may be used as a powerful predictive tool to identify tissues and disorders that will particularly benefit from treatment with an antagonist of Hh pathway.

In one aspect, GLI-1 expression levels can be detected, either by direct detection of the transcript or by detection of protein levels or activity. Transcripts may be detected using any of a wide range of techniques that depend primarily on hybridization of probes to the GLI-1 transcripts or to cDNAs synthesized therefrom. Well-known techniques include Northern blotting, reverse-transcriptase PCR and microarray analysis of transcript levels. Methods for detecting GLI protein levels include Western blotting, immunoprecipitation, two-dimensional polyacrylamide gel electrophoresis (2D SDS-PAGE) (for example, compared against a standard wherein the position of the GLI proteins has been determined), and mass spectroscopy. Mass spectroscopy may be coupled with a series of purification steps to allow high-throughput identification of many different protein levels in a particular sample. Mass spectroscopy and 2D SDS-PAGE can also be used to identify post-transcriptional modifications to proteins including proteolytic events, ubiquitination, phosphorylation, lipid modification etc. GLI activity may also be assessed by analyzing binding to substrate DNA or in vitro transcriptional activation of target promoters. Gel shift assays, DNA footprinting assays and DNA-protein crosslinking assays are all methods that may be used to assess the presence of a protein capable of binding to GLI binding sites on DNA. (*J Mol Med* 1999; 77(6):459-68; *Cell* 2000 Feb. 18; 100(4): 423-34; *Development* 2000; 127(19):4293-4301).

In another aspect, GLI transcript levels are measured and diseased or disordered tissues showing abnormally high GLI levels are treated with a hedgehog antagonist. Premature lung tissue, lung cancers (e.g., adenocarcinomas, broncho-alveolar adenocarcinomas, small cell carcinomas), breast cancers (e.g., inferior ductal carcinomas, inferior lobular carcinomas, tubular carcinomas), prostate cancers (e.g., adenocarcinomas), pancreatic adenocarcinomas, gastric cancers, and benign prostatic hyperplasias all show strongly elevated GLI-1 expression levels in certain cases. Accordingly, GLI-1 expression levels are a powerful diagnostic device to determine which of these tissues should be treated with a smoothened antagonist. In addition, there is substantial correlative evidence that cancers of urothelial cells (e.g., bladder cancer, other urogenital cancers) will also have elevated GLI-1 levels in certain cases. For example, it is known that loss of heterozygosity on chromosome 9q22 is common in bladder cancers. The ptc-1 gene is located at this position and ptc-1 loss of function is probably a partial cause of hyperproliferation, as in many other cancer types. Accordingly, such cancers would also show high GLI expression and would be particularly amenable to treatment with a smoothened antagonist.

It is anticipated that any degree of GLI overexpression may be useful in determining that a smoothened antagonist will be an effective therapeutic. In one aspect, GLI should be expressed at a level at least twice as high as normal.

The compounds and compositions of the present invention can be used in the treatment of neoplastic or hyperplastic transformations such as may occur in the central nervous system. For instance, the smoothened antagonists can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas. In one aspect, the subject method can be used as part of a treatment regimen for malignant medulloblastoma and other primary CNS malignant neuroectodermal tumors.

In another aspect, the methods of the invention can be used as part of treatment program for medulloblastoma. These tumors are also referred to as primitive neuroectodermal tumor (PNET). Medulloblastoma, a primary brain tumor, is the most common brain tumor in children. It is a primitive neuroectodermal tumor arising in the posterior fossa. Medulloblastomas account for approximately 25% of all pediatric brain tumors. Histologically, they are small round cell tumors commonly arranged in true rosettes, but may display some differentiation to astrocytes, ependymal cells or neurons. They may arise in other areas of the brain including the pineal gland (pineoblastoma) and cerebrum. Those arising in the supratentorial region generally fare worse than their counterparts. Medulloblastoma/PNETs are known to recur anywhere in the CNS after resection, and can even metastasize to bone. Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other aspects, the smoothened antagonists of the invention can be used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. In 51 children reported with ependymomas, ¾ were histologically benign. Approximately ⅔ arose from the region of the 4th ventricle. One third presented in the supratentorial region. Age at presentation peaks between birth and 4 years. The median age is about 5 years. Because so many children with this disease are babies, they often require multimodal therapy.

It has been reported that Sonic hedgehog regulates lung mesenchymal cell proliferation in vivo. Accordingly, methods of the present invention can be used to regulate regeneration of lung tissue, e.g., in the treatment of emphysema. It has also been demonstrated that Sonic hedgehog is expressed in human lung squamous carcinoma and adenocarcinoma cells.

Fujita et al. (1997) *Biochem Biophys Res Commun* 238: 658. The expression of Sonic hedgehog was also detected in the human lung squamous carcinoma tissues, but not in the normal lung tissue of the same patient. They also observed that Sonic hedgehog stimulates the incorporation of BrdU into the carcinoma cells and stimulates their cell growth, while anti-Shh-antibody inhibited their cell growth. These results suggest that Hh, and/or SMO is involved in the cell growth of such transformed lung tissue and therefore indicate that the smoothened antagonists of the invention can be used as part of a treatment of lung carcinoma and adenocarcinomas, and other proliferative disorders involving the lung epithelia.

BCC is the most common human cancer, accounting for about 70% of human skin cancers, and representing at least one third of all cancer diagnosed in the US each year. More than 99% of BCC cases arise sporadically in the population, with only 0.5% of cases arising in individuals with Gorlin's Syndrome (GS). BCC rarely metastasizes, but can be locally aggressive and recurrent. Inactivating mutations in PTCH1 occur most commonly in these tumors. A subset of BCC is driven via mutations in SMO, and these mutations activate the pathway by generating proteins with decreased sensitivity to PTCH1 suppression. In one aspect, the methods of the current invention can be used for treatment of BCC.

Hh pathway has been implicated in many other types of cancer, including pancreatic cancer, other tumors of the gastrointestinal (GI) tract and prostate cancer. Abnormal expression of SHH, PTCH1 and SMO has been shown early in the formation of human pancreatic tumors. Thayer, S. P. et al. (2003) *Nature* 425: 313-317. Several pancreatic cancer cell lines were found to be PTCH1 and SMO-positive and growth inhibited in vitro by cyclopamine, suggesting an active autocrine loop through which tumor cells both make and respond to Hh ligand. Furthermore, systemic treatment with cyclopamine slowed the growth of tumors formed by these cell lines when implanted into nude mice. Similar observations were made for pancreatic and other GI tumors. Berman, D. M. et al. (2003) *Nature* 425: 846-851. Similar data was provided for prostate cancer as well, including SHH overexpression in tumor biopsies, especially in higher Gleason grade tumors, and in vitro and in vivo inhibitory effects of cyclopamine on growth of prostate cancer cell lines. The Hh pathway was further implicated in prostate tumor metastasis, as the capacity of AT6.3 cells to metastasize to the lung was completely abrogated by cyclopamine, and AT2.1, a rarely metastasizing clone, could be induced to metastasize by overexpression of GLI1, in a cyclopamine-insensitive manner. Thus, the smoothened antagonists of the invention can be used for the treatment of pancreatic and prostatic cancers.

Many other tumors may, based on evidence such as involvement of the Hh pathway in these tumors, or detected expression of hedgehog or its receptor in these tissues during development, be affected by treatment with the subject compounds. Such tumors include, but are by no means limited to, tumors related to Gorlin's syndrome (e.g., medulloblastoma, meningioma, etc.), tumors evidenced in PTCH1 knock-out mice (e.g., hemangioma, rhabdomyosarcoma, etc.), tumors resulting from GLI-1 amplification (e.g., glioblastoma, sarcoma, etc.), tumors connected with TRC8, a PTCH1 homolog (e.g., renal carcinoma, thyroid carcinoma, etc.), Ext-1-related tumors (e.g., bone cancer, etc.), Shh-induced tumors (e.g., lung cancer, chondrosarcomas, etc.), and other tumors (e.g., breast cancer, urogenital cancer (e.g., kidney, bladder, ureter, prostate, etc.), adrenal cancer, gastrointestinal cancer (e.g., stomach, intestine, etc.).

Further, the pharmaceutical preparations of the invention can be used for the treatment of hyperplastic epidermal conditions, such as keratosis, as well as for the treatment of neoplastic epidermal conditions such as those characterized by a high proliferation rate for various skin cancers, as for example squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

The present invention, thus generally described, will be understood more readily by reference to the following examples, which are provided by way of illustration and are not intended to be limiting of the present invention. Compounds of the invention may be synthesized from simple starting molecules and commercially available materials as illustrated in the Examples. Various modifications of the invention in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence. The structure of the prepared compounds is verified by mass spectral (MS) data. For some compounds, ions having mass greater than M+H are reported. These ions generally represent dimers or trimers of the synthesized compound, and in some instances represent trifluoroacetate adducts generated from the mobile phase of the MS. The trifluoroacetate adducts will have a weight of M+115.

Example 1

Synthesis of (2-methyl-4-(4-phenylphthalazin-1-yl)piperazin-1-yl)(thiophen-2-yl)methanone (1)

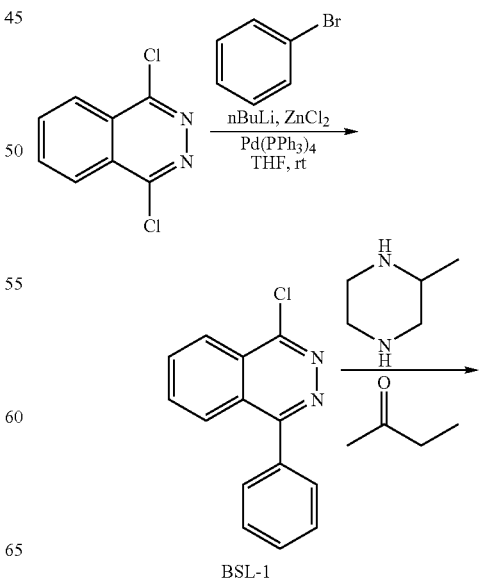

BSL-1

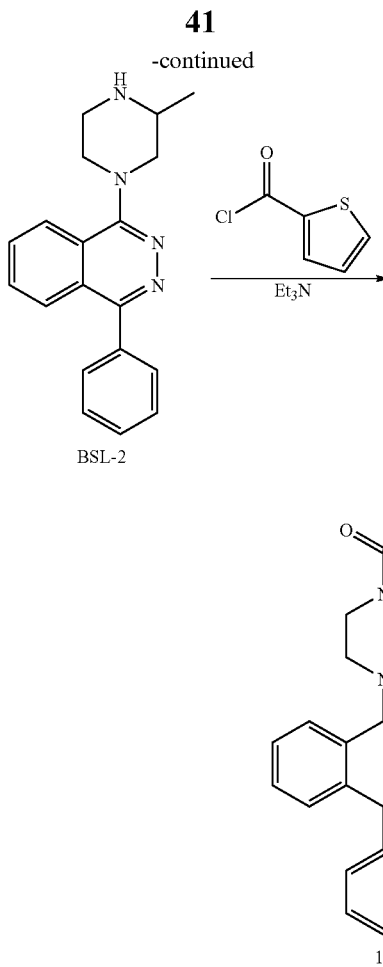

BSL-2

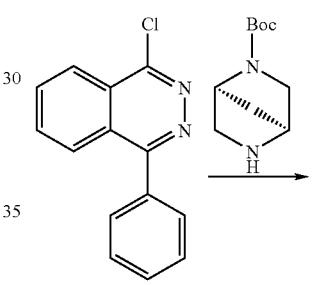

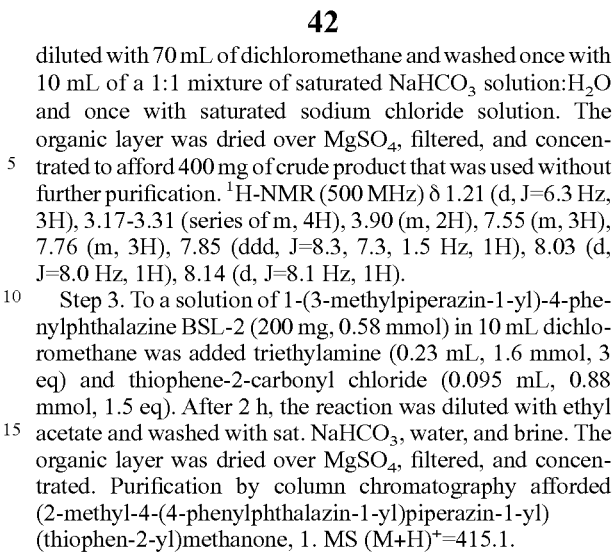

1

Compound 1 was prepared according to the scheme described in Method A.

Step 1. Synthesis of 1-chloro-4-phenylphthalazine (BSL-1). Bromobenzene (1.68 mL, 16 mmol, 1.6 eq) was dissolved in 60 mL of anhydrous THF and cooled to −78° C. n-BuLi (1.6 M in hexanes, 10 mL, 16 mmol, 1.6 eq) was added dropwise with stirring. After 30 min, ZnCl$_2$ (0.5 M in ethyl ether, 32 mL, 16 mmol, 1.6 eq) was added and the solution was warmed to room temperature and aged for 30 min. Separately, 1,4-dichlorophthalazine (1.99 g, 10 mmole, 1 eq) and Pd(PPh$_3$)$_4$ were slurried in 20 mL of anhydrous THF and then transferred via cannula to the reaction mixture, followed by 2×20 mL THF rinses. The reaction mixture was allowed to stir overnight, and then quenched by addition of 50 mL of saturated NaHCO$_3$ solution. The biphasic mixture was filtered through Celite®, and the layers were separated. The aqueous layer was extracted with CH$_2$Cl$_2$, and the combined organic layers were dried over MgSO$_4$, filtered, and concentrated in vacuo. Purification by column chromatography (8:2 hexanes: ethyl acetate) afforded 1.1 g (4.6 mmol, 46%) of 1-chloro-4-phenylphthalazine (BSL-1). If necessary, the product can be further purified by recrystallization from isopropanol. ($^1$H NMR, 500 MHz) δ 7.60 (m, 3H), 7.75 (m, 2H), 7.95 (t, J=7.3 Hz, 1H), 8.08 (t, J=7.1 Hz, 1H), 8.10 (d, J=8.3 Hz, 1H), 8.43 (d, J=8.3 Hz, 1H).

Step 2. A solution of 1-chloro-4-phenylphthalazine BSL-1 (240 mg, 1 mmol) and 2-methyl piperazine (500 mg, 5 mmol, 5 eq) in 5 mL of methylisobutylketone (MIBK) was heated to 120° C. for 3 h. The reaction was cooled to rt and the MIBK was removed under vacuum. The crude reaction mixture was diluted with 70 mL of dichloromethane and washed once with 10 mL of a 1:1 mixture of saturated NaHCO$_3$ solution:H$_2$O and once with saturated sodium chloride solution. The organic layer was dried over MgSO$_4$, filtered, and concentrated to afford 400 mg of crude product that was used without further purification. $^1$H-NMR (500 MHz) δ 1.21 (d, J=6.3 Hz, 3H), 3.17-3.31 (series of m, 4H), 3.90 (m, 2H), 7.55 (m, 3H), 7.76 (m, 3H), 7.85 (ddd, J=8.3, 7.3, 1.5 Hz, 1H), 8.03 (d, J=8.0 Hz, 1H), 8.14 (d, J=8.1 Hz, 1H).

Step 3. To a solution of 1-(3-methylpiperazin-1-yl)-4-phenylphthalazine BSL-2 (200 mg, 0.58 mmol) in 10 mL dichloromethane was added triethylamine (0.23 mL, 1.6 mmol, 3 eq) and thiophene-2-carbonyl chloride (0.095 mL, 0.88 mmol, 1.5 eq). After 2 h, the reaction was diluted with ethyl acetate and washed with sat. NaHCO$_3$, water, and brine. The organic layer was dried over MgSO$_4$, filtered, and concentrated. Purification by column chromatography afforded (2-methyl-4-(4-phenylphthalazin-1-yl)piperazin-1-yl)(thiophen-2-yl)methanone, 1. MS (M+H)$^+$=415.1.

Example 2

Synthesis of (1S,4S)-2-(4-phenylphthalazin-1-yl)-2,5-diaza-bicyclo[2.2.1]heptane (BSL-4)

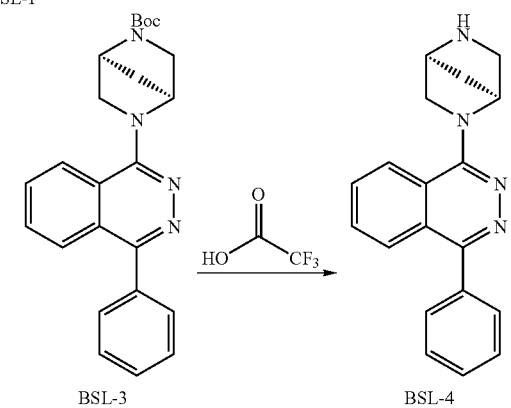

To a 20 mL reaction vial was added 1-chloro-4-phenylphthalazine BSL-1 (300 mg, 1.25 mmol) and (1S,4S)-2-boc-2,5-diazabicyclo[2.2.1]heptane (494 mg, 2.5 mmol, 2 eq). The mixture was heated under nitrogen at 90° C. for 1 h. The reaction was cooled to room temperature and the solid mass was dissolved in dichloromethane (50 mL) and washed once with 5 mL of sat. NaHCO$_3$ and once with 50 mL of sat. NaCl solution. The organic layer was dried over MgSO$_4$, filtered, and concentrated. Purification by column chromatography (70% ethyl acetate in hexanes) afforded (1S,4S)-tert-butyl 5-(4-phenylphthalazin-1-yl)-2,5-diaza-bicyclo[2.2.1]heptane-2-carboxylate (BSL-3). MS (M+H)$^+$=403.1.

To a round bottomed flask containing BSL-3 (410 mg, 1 mmol) was added dichloromethane (10 mL), followed by trifluoroacetic acid (1.96 mL, 25 mmol, 25 eq). After 1 h, the reaction was poured into sat. NaHCO$_3$ solution and extracted with dichloromethane (2×25 mL). The combined organic layers were dried over MgSO$_4$, filtered, and concentrated to afford 294 mg of the title compound (BSL-4). MS (M+H)$^+$=303.1.

Example 3

Synthesis of 4-(4-chlorophthalazin-1-yl)-2,5-dimethylpiperazin-1-yl)(phenyl)methanone (BSL-5)

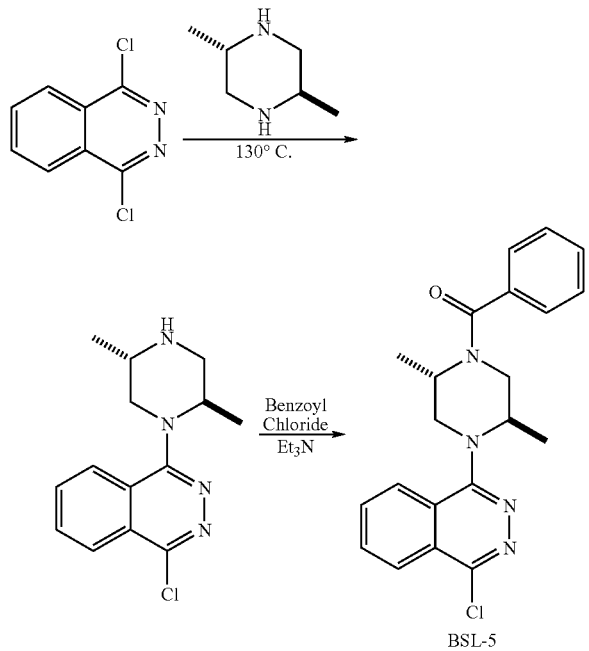

BSL-5

Example 4

Synthesis of 1-(cis-3,5-dimethylpiperazin-1-yl)-4-phenylphthalazine (BSL-6)

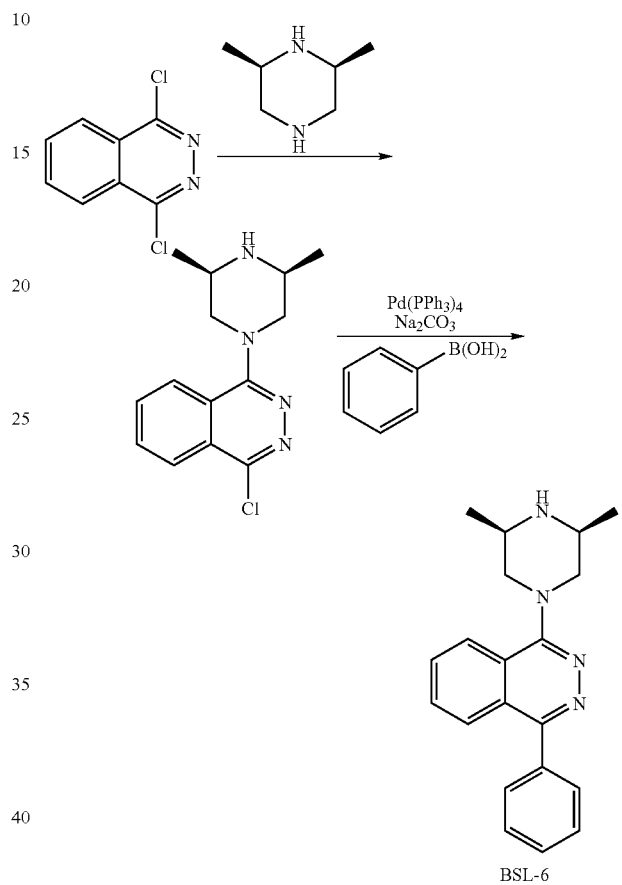

BSL-6

1,4-dichlorophthalazine (1.0 g, 5 mmole) and trans-2,5-dimethyl piperazine were combined in a reaction vial and heated to 130° C. for 3 h with stirring. After cooling to room temperature, the solid residue was dissolved in 150 mL of dichloromethane and washed with 1×20 mL of 1:1 saturated NaHCO$_3$ solution:H$_2$O and 1×20 mL of saturated NaCl solution. The organic phase was dried over MgSO$_4$, filtered, and concentrated. Purification by column chromatography (100:5:1 dichloromethane:methanol:triethylamine) afforded 1-chloro-4-(trans-2,5-dimethylpiperazin-1-yl)phthalazine. MS (M+H)$^+$=277.1.

To a solution of 1-chloro-4-(trans-2,5-dimethylpiperazin-1-yl)phthalazine (700 mg, 2.5 mmol) in 10 mL of dichloromethane was added triethylamine (0.70 mL, 5 mmol, 2 eq), followed by benzoyl chloride (0.32 mL, 2.75 mmol, 1.1 eq). After 5 min, the reaction was diluted with 200 mL of ethyl acetate and washed with 1×20 mL of sat. NaHCO$_3$, 1×20 mL of H$_2$O, and 1×20 mL of sat. NaCl. The organic layer was dried over MgSO$_4$, filtered, and concentrated. Purification by column chromatography (60% ethyl acetate in hexanes) afforded 670 mg (70% yield) of racemic trans-4-(4-chlorophthalazin-1-yl)-2,5-dimethylpiperazin-1-yl)(phenyl)methanone (BSL-5). $^1$H-NMR (400 MHz) δ 1.18 (d, J=6.7 Hz, 3H), 1.43 (d, J=7.0 Hz, 3H), 3.20-4.55 (series of m, 6H), 7.43 (s, 5H), 7.91 (m, 2H), 8.08 (m, 1H), 8.27 (m, 1H).

1,4-dichlorophthalazine (1.6 g, 8 mmol) was slurried in 80 mL of MIBK and 2,6 cis-dimethyl piperazine (3.6 g, 32 mmol, 4 eq) was added. The reaction was stirred overnight and the solvent was removed in vacuo. The crude material was dissolved in 200 mL of CH$_2$Cl$_2$ and washed with 1×30 mL of a 1:1 mixture of H$_2$O and sat. sodium bicarbonate and 1×30 mL of sat. NaCl solution. The organic layer was dried over MgSO$_4$, filtered, and concentrated. Purification by column chromatography (100:5:1 dichloromethane:methanol:triethylamine) afforded 1.6 g (72%) of 1-chloro-4-(cis)-3,5-dimethylpiperazin-1-yl)phthalazine. MS (M+H)$^+$=277.1.

To a reaction flask containing 1-chloro-4-(cis)-3,5-dimethylpiperazin-1-yl)phthalazine (552 mg, 2 mmol) and phenylboronic acid (366 mg, 3 mmol, 1.5 eq) was added toluene (20 mL), 2M Na$_2$CO$_3$ (2 mL, 4 mmol, 2 eq), and Pd(PPh$_3$)$_4$ (115.2 mg, 0.1 mmol, 0.05 eq). The flask was fitted with a reflux condenser, purged with nitrogen, and heated to 100° C. for 12 h. After cooling to room temperature, the reaction was diluted with 150 mL of ethyl acetate and washed with 1×10 mL of sat. NaHCO$_3$, 1×10 mL of H$_2$O, and 1×10 mL of brine. The combined organic layers were dried over MgSO$_4$, filtered, and concentrated. Purification by column chromatography (100:5:1 dichloromethane:methanol:triethylamine) afforded 200 mg (31%) of 1-(cis-3,5-dimethylpiperazin-1-yl)-4-phenylphthalazine BSL-6. MS (M+H)$^+$=319.1.

Example 5

Synthesis of 1-(3,3-dimethylpiperazin-1-yl)-4-phenylphthalazine (BSL-7)

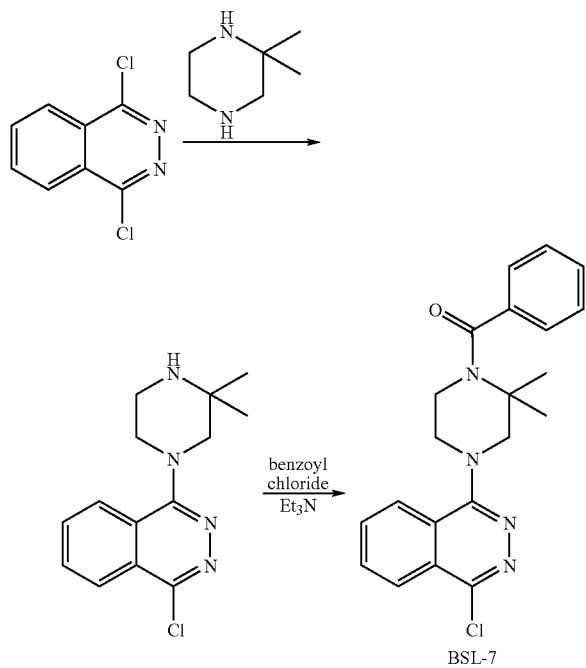

1,4-dichlorophthalazine (1 g, 5 mmol) and 2,2-dimethyl piperazine (1.75 g, 15 mmol, 3 eq) were slurried in 5 mL of MEK for 3 h at 45° C. After cooling to rt, the reaction was diluted with 150 mL of dichloromethane and washed with 1×20 mL of sat. NaHCO$_3$ and 1×20 mL of sat. NaCl solution. The organic layer was dried over MgSO$_4$, filtered, and concentrated. Purification by column chromatography (100:5→8:1 dichloromethane:methanol:triethylamine) afforded 1-chloro-4-(3,3-dimethylpiperazin-1-yl)phthalazine. MS (M+H)$^+$=277.0.

To a solution of 1-chloro-4-(3,3-dimethylpiperazin-1-yl) phthalazine (540 mg, 2 mmol) in 10 mL of dichloromethane was added triethylamine (0.56 mL, 4 mmol, 2 eq), followed by benzoyl chloride (0.26 mL, 2.2 mmol, 1.1 eq). The reaction was stirred at rt for 30 min and diluted with 100 mL of ethyl acetate. The organic layer was washed with 1×10 mL of sat. NaHCO$_3$ solution and 1×10 mL of sat. NaCl solution. Purification by column chromatography (100:2 dichloromethane:methanol) afforded 1-(3,3-dimethylpiperazin-1-yl)-4-phenylphthalazine (BSL-7). $^1$H-NMR (400 Mhz) δ 1.65 (s, 6H), 3.46 (s, 2H), 3.63 (m, 4H), 7.34 (m, 3H), 7.42 (m, 3H), 7.42 (m, 3H), 7.83 (m, 2H), 8.03 (m, 1H), 8.17 (m, 1H).

Example 6

The following compounds were produced as described in Example 1 using the appropriate substrate (BSL#) and acylation reagent as indicated in Table 1.

TABLE 1

| Comp # | Name | Structure | M cal'd | M + H found | Substrate | Acylation Reagent |
|---|---|---|---|---|---|---|
| 2 | (2-methyl-4-(4-phenylphthalazin-1-yl)piperazin-1-yl)(phenyl)methanone | 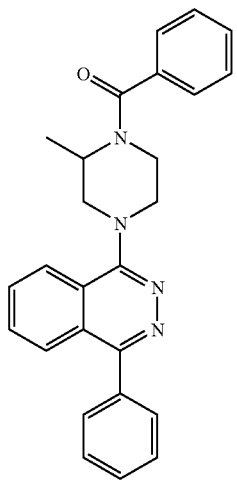 | 408.2 | 409.1 | BSL-2 | Benzoyl chloride |

TABLE 1-continued

| Comp # | Name | Structure | M cal'd | M + H found | Substrate | Acylation Reagent |
|---|---|---|---|---|---|---|
| 3 | phenyl((1S,4S)-5-(4-phenylphthalazin-1-yl)-2,5-diazabicyclo[2.2.1]-heptan-2-yl)-methanone | 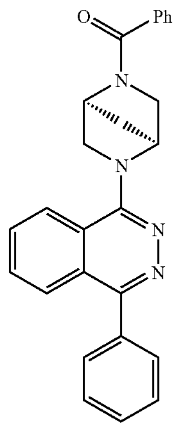 | 406.2 | 407.2 | BSL-4 | Benzoyl Chloride |

Example 7

Synthesis of (R)-(3-methyl-4-(4-phenylphthalazin-1-yl)piperazin-1-yl)(phenyl)methanone 4

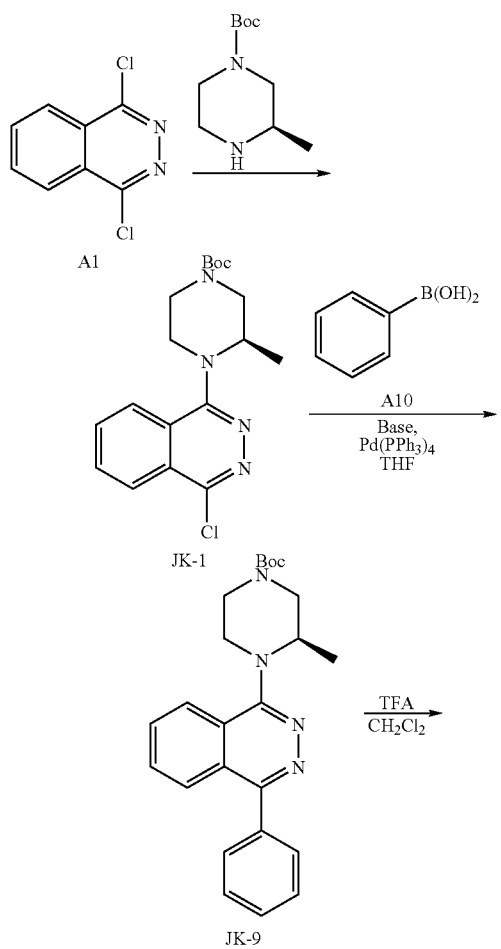

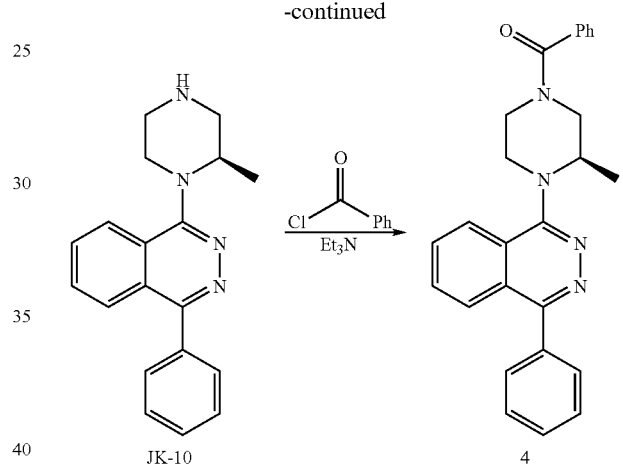

Compound 4 was prepared as described in general Method B.

Step 1. Preparation of (R)-tert-butyl 4-(4-chlorophthalazin-1-yl)-3-methylpiperazine-1-carboxylate (JK-1)

1,4-dichlorophthalazine (5.00 g, 25.1 mmol) and (R)-tert-butyl 3-methylpiperazine-1-carboxylate (11.06 g, 55.2 mmol) were mixed intimately and placed in a flask under an Argon atmosphere. The flask was heated at 120° C. for approximately 16 hours, after which time LC/MS showed disappearance of the starting material. The reaction was cooled, taken up in dichloromethane (150 mL), and washed once with aqueous sodium bicarbonate (50% of saturated) and once with saturated sodium chloride solution. The organic phase was dried (MgSO$_4$) and evaporated to give an orange oil. Chromatography over silica gel with a gradient of hexanes/0-10% acetone gave a pale yellow solid JK-1. MS (M+H)$^+$=363.1.

Step 2. Preparation of (R)-tert-butyl 3-methyl-4-(4-phenylphthalazin-1-yl)piperazine-1-carboxylate (JK-9)

(R)-tert-butyl 4-(4-chlorophthalazin-1-yl)-2-methylpiperazine-1-carboxylate (0.500 g, 1.38 mmol), phenylboronic acid (0.168 g, 1.38 mmol), and tetrakis(triphenylphosphine) palladium (0) (79.9 mg, 0.069 mmol) were placed in a flask under argon. Degassed toluene (15 mL) and aqueous sodium carbonate (2.0 M, 1.5 mL) were added and the reaction heated at 100° C. for 22 hours. The reaction was allowed to cool before being added to 80 mL aqueous $K_2CO_3$ (10%). The aqueous phase was extracted with dichloromethane three times, and the combined organics were dried ($MgSO_4$) and evaporated to give a yellow oil. Chromatography over silica gel with a gradient of hexanes/0-70% ethyl acetate gave an off-white solid. $^1$H-NMR (500 Mhz) δ 1.17 (br d, J=5.5 Hz, 3H), 1.44 (s, 9H), 3.40-3.65 (series of m, 5H), 3.82 (m, 1H), 4.06 (m, 1H), 7.47 (m, 3H), 7.69 (m, 3H), 7.78 (td, J=6.7, 1.2 Hz, 1H), 7.97 (d, J=7.9 Hz, 1H), 8.09 (d, J=8.5 Hz, 1H).

Step 3. Preparation of (R)-1-(2-methylpiperazin-1-yl)-4-phenylphthalazine (JK-10)

(R)-tert-butyl 2-methyl-4-(4-phenylphthalazin-1-yl)piperazine-1-carboxylate (495 mg, 1.22 mmol) was dissolved in dichloromethane (15 mL). Trifluoroacetic acid (2.36 mL) was added and the reaction stirred at rt for 1.5 hours. The reaction was added to saturated $NaHCO_3$ (30 mL) and neutralized by the portion wise addition of solid $NaHCO_3$. The layers were separated and extracted twice with dichloromethane. The combined organics were dried ($MgSO_4$) and evaporated to give a pale yellow foam. MS $(M+H)^+=305.4$.

Step 4. Preparation of (R)-(3-methyl-4-(4-phenylphthalazin-1-yl)piperazin-1-yl)(phenyl)methanone (4)

(R)-1-(2-methylpiperazin-1-yl)-4-phenylphthalazine (JK-10) (200 mg, 0.65 mmol) was dissolved in 5 mL of dichloromethane at room temperature. To this solution was added triethylamine (0.18 mL, 1.3 mmol, 2 eq) and benzoyl chloride (0.083 mL, 0.72 mmol, 1.1 eq). After 5 minutes, the reaction was diluted with 75 mL of ethyl acetate and washed with 5 mL of sat. $NaHCO_3$, 5 mL of water, and 5 mL of brine. The organic phase was dried over $MgSO_4$, filtered, and concentrated. Purification by column chromatography (35% ethyl acetate in hexanes) afforded 200 mg (75% yield) of (R)-(3-methyl-4-(4-phenylphthalazin-1-yl)piperazin-1-yl)(phenyl)methanone (4). MS $(M+H)^+=409.1$

Example 8

Preparation of (R)-1-chloro-4-(2-methylpiperazin-1-yl)phthalazine (JK-2)

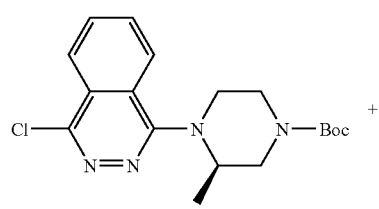

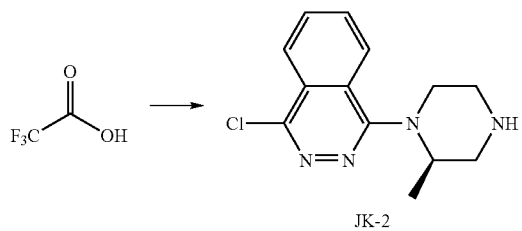

(R)-tert-butyl 4-(4-chlorophthalazin-1-yl)-3-methylpiperazine-1-carboxylate (1.20 g, 3.31 mmol) was dissolved in dry dichloromethane (40 mL). Trifluoroacetic acid (8 mL) was added dropwise and allowed to stir at RT for 2 hours. The reaction was added to saturated $NaHCO_3$ (200 mL) and the aqueous phase was extracted with 3×100 mL of dichloromethane. The combined organics were dried ($MgSO_4$) and evaporated to give a pale yellow solid. MS $(M+H)^+=263.1$.

Example 9

Preparation of (S)-1-chloro-4-(3-methylpiperazin-1-yl)phthalazine (JK-3)

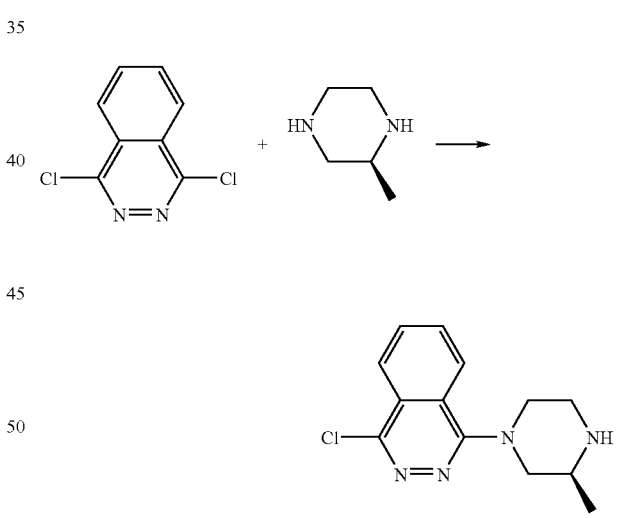

1,4-dichlorophthalazine (5.00 g, 25.1 mmol) and (R)-2-methylpiperazine (6.29 g, 62.8 mmol) were dissolved in methyl ethyl ketone (80 mL) and stirred at rt for 2 days. The reaction was added to ethyl acetate (350 mL) and washed once with aqueous $K_2CO_3$ (10%), once with water, and once with saturated sodium chloride. The organic phase was dried ($MgSO_4$) and evaporated to give an orange oil. Chromatography over silica gel with a gradient of dichloromethane/0-5% methanol gave a pale yellow solid. MS $(M+H)^+=263.1$.

Example 10

Preparation of (S)-(4-(4-chlorophthalazin-1-yl)-2-methylpiperazin-1-yl)(phenyl)methanone (JK-4)

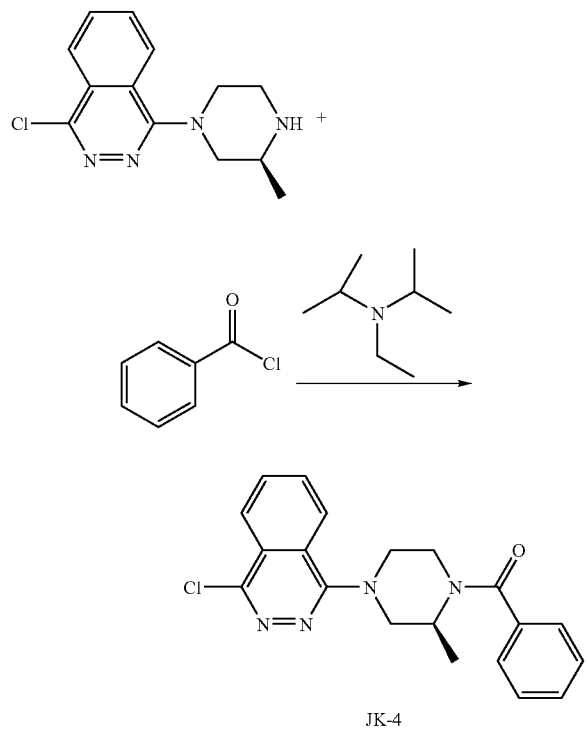

JK-4

(S)-1-chloro-4-(3-methylpiperazin-1-yl)phthalazine (3.64 g, 13.9 mmol) was dissolved in dry dichloromethane (30 mL) and triethylamine (4.26 mL, 30.6 mmol). Benzoyl chloride (1.77 mL, 15.3 mmol) was added and stirred at rt for 1 hour. The reaction was added to saturated NaHCO$_3$ (150 mL) and the aqueous layer was extracted with 3× dichloromethane. The combined organics were dried (MgSO$_4$) and evaporated to give a yellow oil. Chromatography over silica gel with a gradient of hexanes/30-100% ethyl acetate gave an off-white solid. MS (M+H)$^+$=367.1.

Example 11

Preparation of (R)-(4-(4-chlorophthalazin-1-yl)-3-methylpiperazin-1-yl)(phenyl)methanone (JK-5)

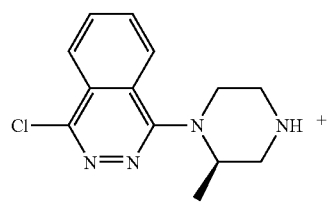

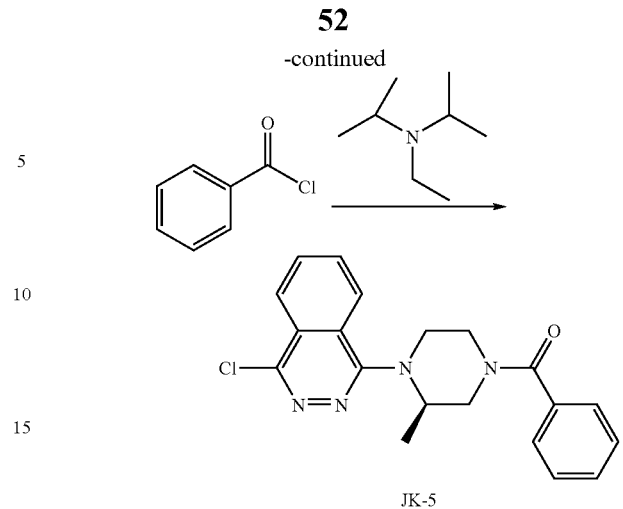

JK-5

(R)-1-chloro-4-(2-methylpiperazin-1-yl)phthalazine (2.94 g, 11.94 mmol) was dissolved in dry DMF (24 mL) and N,N-diisopropylethylamine (3.12 mL, 17.9 mmol). Benzoyl chloride (1.43 mL, 12.3 mmol) was added dropwise and the reaction stirred at rt for 16 hours. The reaction was taken up in ethyl acetate (200 mL), and washed with aqueous K$_2$CO$_3$ (10%), water, and then saturated sodium chloride. The organic phase was dried (MgSO$_4$) and evaporated to give a yellow oil. Chromatography over silica gel with a gradient of hexanes/0-70% ethyl acetate gave an off-white solid. MS (M+H)$^+$=367.

Example 12

Preparation of (S)-tert-butyl 4-(4-chlorophthalazin-1-yl)-2-methylpiperazine-1-carboxylate (JK-6)

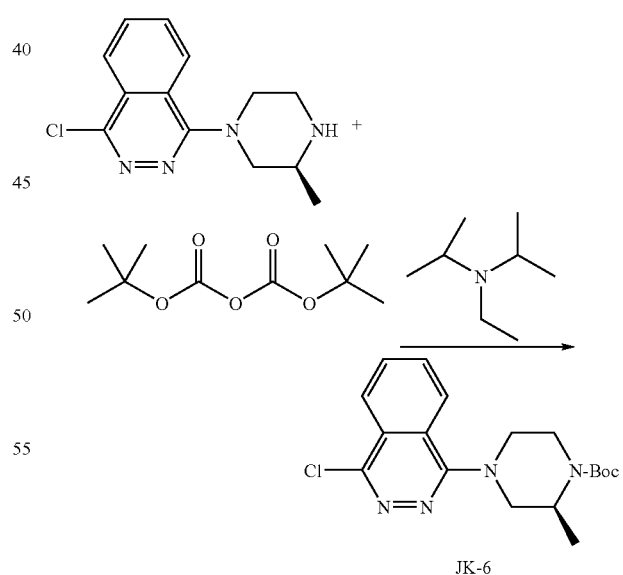

JK-6

(S)-1-chloro-4-(3-methylpiperazin-1-yl)phthalazine (1.50 g, 5.71 mmol) and di-t-butylcarbonate (1.73 g, 6.56 mmol) were dissolved in DMF (12 mL) and N,N-diisopropylethylamine (2 mL) and stirred at rt for 4 hours. The reaction was taken up in ethyl acetate (150 mL) and washed with aqueous K$_2$CO$_3$ (10%), water, and saturated sodium chloride. The organics were dried (MgSO$_4$) and evaporated to give a yellow oil. Chromatography over silica gel with a gradient of hexanes/0-40% ethyl acetate gave an off-white solid. MS (M+H)$^+$=363.1.

Example 13

Preparation of (S)-tert-butyl 2-methyl-4-(4-phenylphthalazin-1-yl)piperazine-1-carboxylate (JK-7)

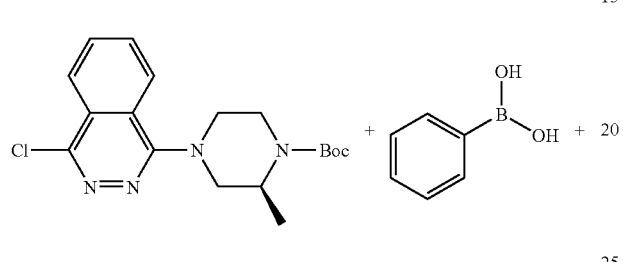

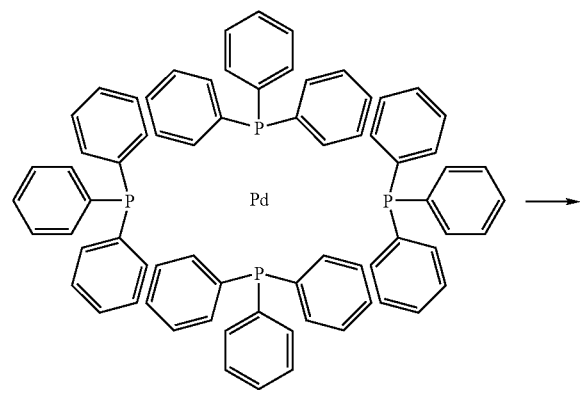

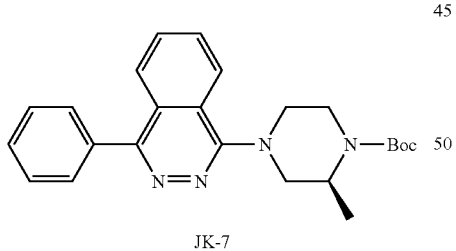

JK-7

(S)-tert-butyl 4-(4-chlorophthalazin-1-yl)-2-methylpiperazine-1-carboxylate (2.10 g, 5.79 mmol), phenylboronic acid (1.06 g, 8.69 mmol), and tetrakis(triphenylphosphine)palladium (0) (0.334 g, 0.289 mmol) were placed in a flask under argon. Degassed toluene (50 mL) and aqueous sodium carbonate (2.0 M, 5.0 mL) were added and the reaction heated at 100° C. for 16 hours. The reaction was allowed to cool, diluted with 150 mL of ethyl acetate, and then washed with aqueous K$_2$CO$_3$ (10%), and saturated sodium chloride. The dried organics (MgSO$_4$) were evaporated to give yellow oil. Chromatography over silica gel with a gradient of hexanes/0-40% ethyl acetate gave an off-white solid. MS (M+H)$^+$=405.2.

Example 14

Preparation of (S)-1-(3-methylpiperazin-1-yl)-4-phenylphthalazine (JK-8)

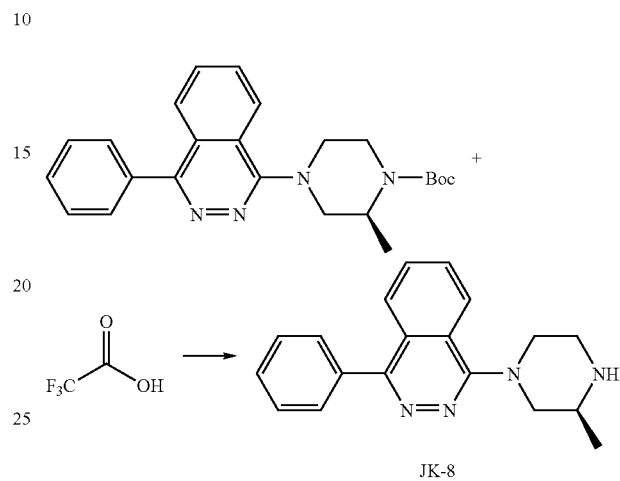

(S)-tert-butyl 2-methyl-4-(4-phenylphthalazin-1-yl)piperazine-1-carboxylate (2.05 g, 5.07 mmol) was dissolved in dichloromethane (75 mL). Trifluoroacetic acid (15 mL) was added and the reaction stirred at rt for 1.5 hours. The reaction was added to saturated NaHCO$_3$ (150 mL) and neutralized by the portion wise addition of solid NaHCO$_3$. The layers were separated and the aqueous phase was extracted twice with dichloromethane. The combined organics were dried (MgSO$_4$) and evaporated to give a pale yellow foam. MS (M+H)$^+$=305.2.

Example 15

Preparation of (S)-tert-butyl 4-benzoyl-3-methylpiperazine-1-carboxylate (JK-11)

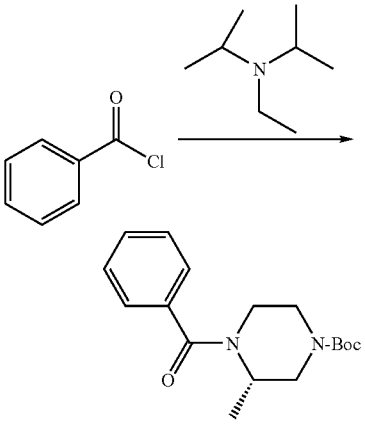

(S)-tert-butyl 3-methylpiperazine-1-carboxylate (6.00 g, 30.0 mmol) was dissolved in dry DMF (40 mL) and N,N-diisopropylethylamine (DIEA) (6.00 mL). Benzoyl chloride (3.65 mL, 31.5 mmol) was added drop-wise and the reaction was stirred at rt for 16 hours. The reaction was taken up in ethyl acetate (200 mL) and washed with aqueous K$_2$CO$_3$ (10%), water, and saturated sodium chloride. The organic phase was dried (MgSO$_4$) and evaporated to give a yellow oil. Chromatography over silica gel with a gradient of hexanes/0-50% ethyl acetate gave an off-white solid.

Example 16

Preparation of (S)-(2-methylpiperazin-1-yl)(phenyl)methanone (JK-12)

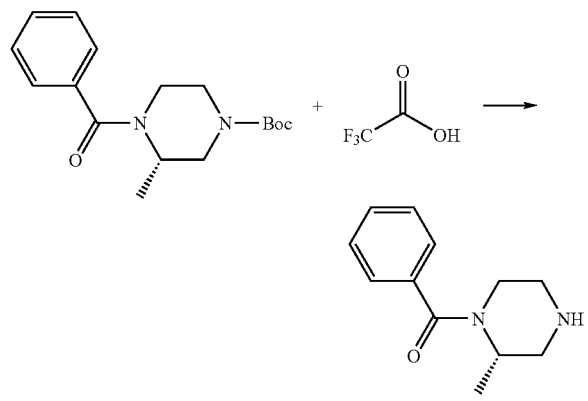

(S)-tert-butyl 4-benzoyl-3-methylpiperazine-1-carboxylate (8.16 g, 26.8 mmol) was dissolved in dichloromethane (200 mL). Trifluoroacetic acid (20.7 ml) was added and the reaction was stirred at rt for 1.5 hours. The reaction was quenched into saturated K$_2$CO$_3$ (30 mL) and neutralized by the portion-wise addition of solid NaHCO$_3$. The layers were separated and extracted twice with dichloromethane. The combined organics were dried (MgSO$_4$) and evaporated to give a yellow oil. MS (M+H)$^+$=205.3.

Example 17

Preparation of 1-chloro-4-((2R,5R)-2,5-dimethylpiperazin-1-yl)phthalazine (JK-13)

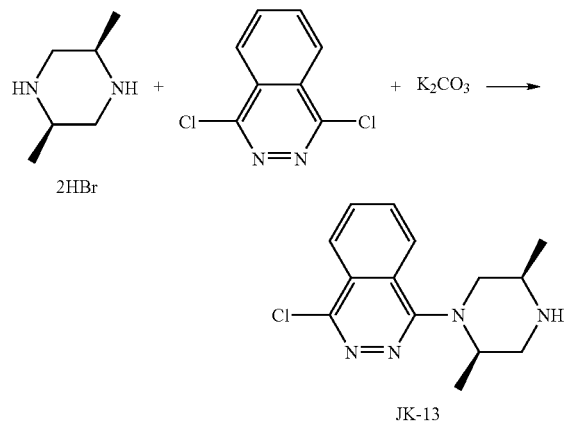

(2R,5R)-2,5-dimethylpiperazine dihydrobromide (2.08 g, 7.54 mmol), 1,4-dichlorophthalazine (0.500 g, 2.52 mmol), potassium carbonate (2.08 g, 15.0 mmol), and N-methylpyrrolidinone (7 mL) were heated at 120° C. for 6 hours. The reaction was taken up in ethyl acetate (75 mL) washed with aqueous K$_2$CO$_3$ (10%), water, and then saturated sodium chloride. The organics were dried (MgSO$_4$) and evaporated to give a yellow oil. Chromatography over silica gel with a gradient of hexanes/0-40% ethyl acetate gave a yellow oil. MS (M+H)$^+$=277.2.

Example 18

Preparation of ((2R,5R)-4-(4-chlorophthalazin-1-yl)-2,5-dimethylpiperazin-1-yl)(phenyl)methanone (JK-14)

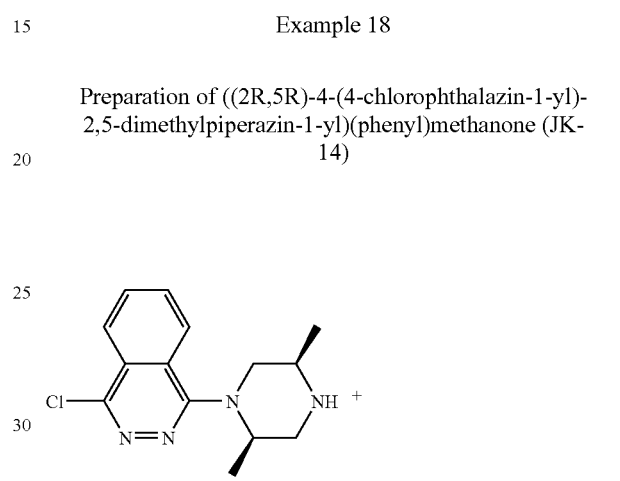

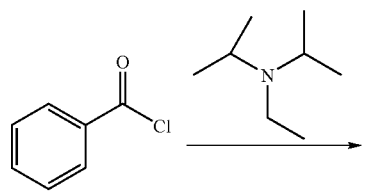

1-chloro-4-((2R,5R)-2,5-dimethylpiperazin-1-yl)phthalazine (245 mg, 0.885 mmol) was dissolved in DMF (3.5 mL) and N,N-diisopropylethylamine (0.70 mL). Benzoyl chloride (0.118 mL, 1.02 mmol) was added and the mixture stirred at rt for 16 hours. The reaction was taken up in ethyl acetate (80 mL) and washed with aqueous K$_2$CO$_3$ (10%), water, and saturated sodium chloride. The organics were dried (MgSO$_4$) and evaporated to give a yellow oil. Chromatography over silica gel with a gradient of hexanes/0-40% ethyl acetate gave an off-white foam. MS (M+H)$^+$=381.8

Example 19

Preparation of 1-benzyl-4-(4-chlorophthalazin-1-yl) piperazin-2-one (JK-15)

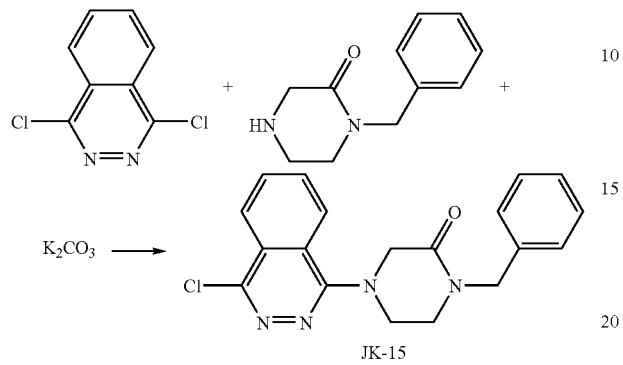

1,4-dichlorophthalazine (500 mg, 2.51 mmol), 1-benzylpiperazin-2-one (526 mg, 2.76 mmol), potassium carbonate (521 mg, 3.01 mmol), and N-methylpyrrolidinone (3 mL) were heated at 110° for 8 hours. The reaction was taken up in ethyl acetate (80 mL) and washed with aqueous $K_2CO_3$ (10%), water, and saturated sodium chloride. The organics were dried ($MgSO_4$) and evaporated to give an orange oil. Chromatography over silica gel with a gradient of hexanes/0-40% ethyl acetate gave an off-white solid. MS $(M+H)^+=353.9$.

Example 20

Preparation of 1-tert-butyl 2-methyl 4-(4-chlorophthalazin-1-yl)piperazine-1,2-dicarboxylate (JK-16)

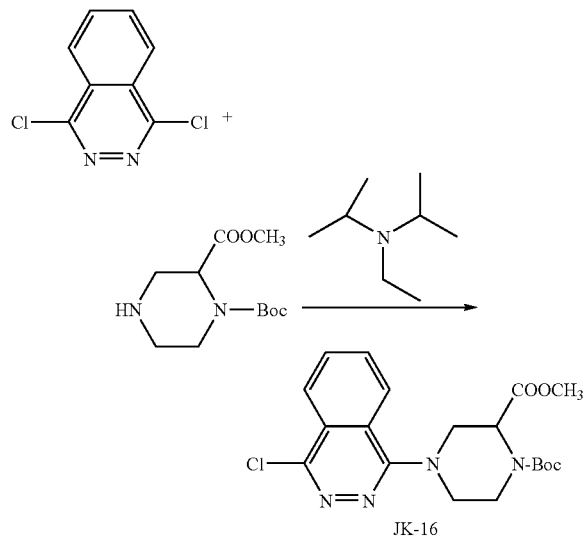

1,4-dichlorophthalazine (741 mg, 3.72 mmol), 1-tert-butyl 2-methyl piperazine-1,2-dicarboxylate (1.00 g, 4.09 mmol), N,N-diisopropylethylamine (0.972 mL), and 4-methyl-2-pentanone (6 mL) were heated at 120° for 16 hours. The solvent was removed and the residue purified by chromatography over silica using a gradient of hexanes/0-70% ethyl acetate. The compound was obtained as a white solid. MS $(M+H)^+=407.1$.

Example 21

Preparation of methyl 4-(4-chlorophthalazin-1-yl) piperazine-2-carboxylate (JK-17)

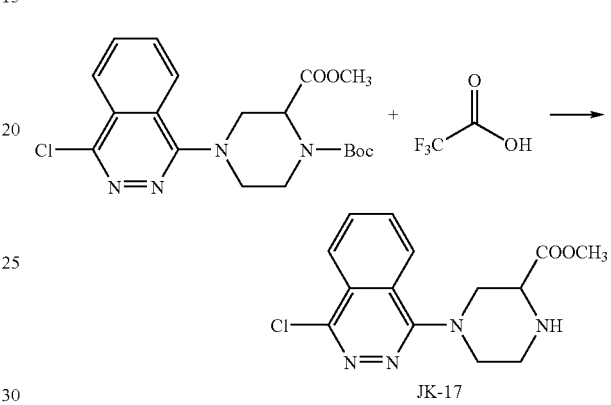

1-tert-butyl 2-methyl 4-(4-chlorophthalazin-1-yl)piperazine-1,2-dicarboxylate (754 mg, 1.85 mmol) was partially dissolved in dichloromethane (20 mL). Trifluoroacetic acid (3.50 mL) was added and the reaction stirred at rt for 4 hours. Saturated sodium bicarbonate (50 mL) was added and stirred for 15 minutes. The layers were separated and the aqueous phase was extracted two more times with dichloromethane. The combined extracts were dried ($MgSO_4$) and evaporated to give a foamy yellow solid. MS $(M+H)^+=307.1$.

Example 22

Preparation of methyl 1-benzoyl-4-(4-chlorophthalazin-1-yl)piperazine-2-carboxylate (JK-18)

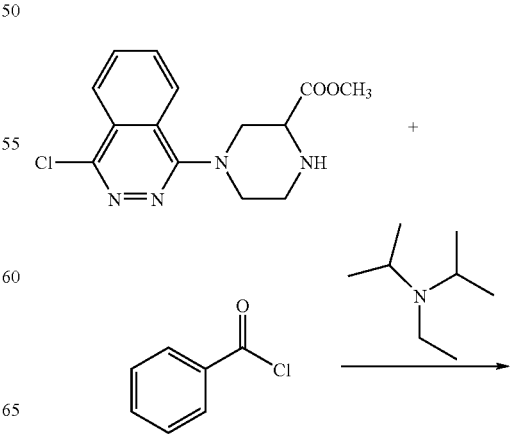

-continued

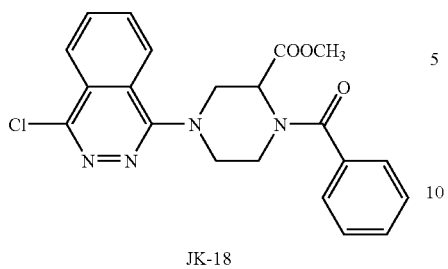

JK-18

Methyl 4-(4-chlorophthalazin-1-yl)piperazine-2-carboxylate (563 mg, 1.84 mmol) was dissolved in DMF (6 mL) and N,N-diisopropylethylamine (1 mL). Benzoyl chloride (0.23 mL, 2.02 mmol) was added and the mixture stirred at rt for 16 hours. The reaction was taken up in ethyl acetate (80 mL), washed with aqueous $K_2CO_3$ (10%), water, and then saturated sodium chloride. The organics were dried ($MgSO_4$) and evaporated to give a yellow oil. Chromatography over silica gel with a gradient of hexanes/0-75% ethyl acetate gave an off-white foam. MS $(M+H)^+=381.8$.

Example 23

Preparation of 1-chloro-4-((2S,5S)-2,5-dimethylpiperazin-1-yl)phthalazine (JK-19)

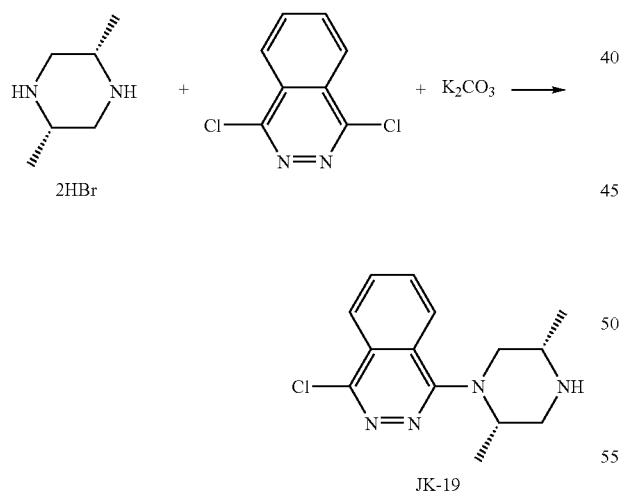

JK-19

(2S,5S)-2,5-dimethylpiperazine dihydrobromide (1.16 g, 4.20 mmol), 1,4-dichlorophthalazine (700 mg, 3.52 mmol), potassium carbonate (973 mg, 7.04 mmol), and N-methylpyrrolidinone (7 mL) were heated at 120° C. for 22 hours. The reaction was taken up in ethyl acetate (80 mL) and washed with aqueous $K_2CO_3$ (10%), water, and saturated sodium chloride. The organics were dried ($MgSO_4$) and evaporated to give an orange oil. Chromatography over silica gel with a gradient of hexanes+2.5% triethylamine/0-100% ethyl acetate+2.5% triethylamine gave a pale yellow semi-solid. MS $(M+H)^+=277.8$.

Example 24

Preparation of ((2S,5S)-4-(4-chlorophthalazin-1-yl)-2,5-dimethylpiperazin-1-yl)(phenyl)methanone (JK-20)

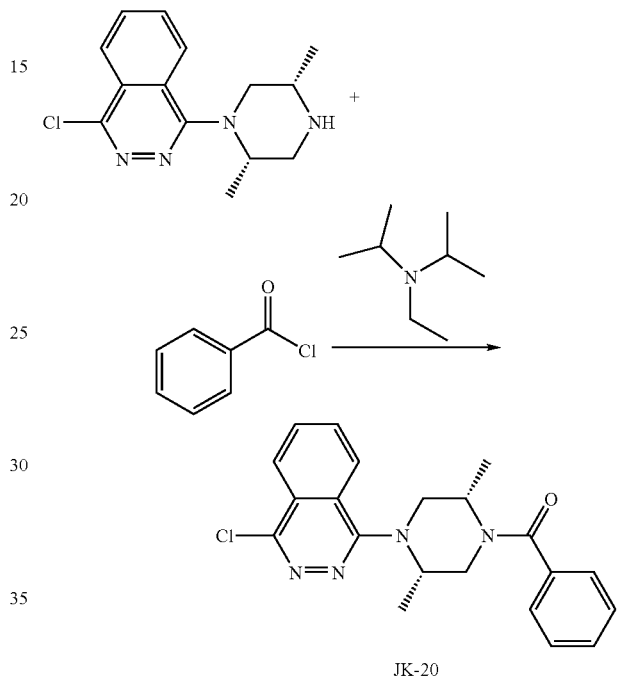

JK-20

1-chloro-4-((2S,5S)-2,5-dimethylpiperazin-1-yl)phthalazine (496 mg, 1.79 mmol) was dissolved in DMF (5 mL) and N,N-diisopropylethylamine (0.5 mL). Benzoyl chloride (0.23 mL, 2.02 mmol) was added and the mixture stirred at rt for 16 hours. The reaction was taken up in ethyl acetate (80 mL) and washed with aqueous $K_2CO_3$ (10%), water, and saturated sodium chloride. The organics were dried ($MgSO_4$) and evaporated to give a yellow oil. Chromatography over silica gel with a gradient of hexanes/0-70% ethyl acetate gave off-white foam. MS $(M+H)^+=381.0$.

Example 25

Preparation of (R)-(4-(4-chlorophthalazin-1-yl)-3-methylpiperazin-1-yl)(cyclohexyl)methanone (JK-21)

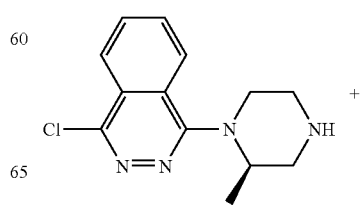

-continued

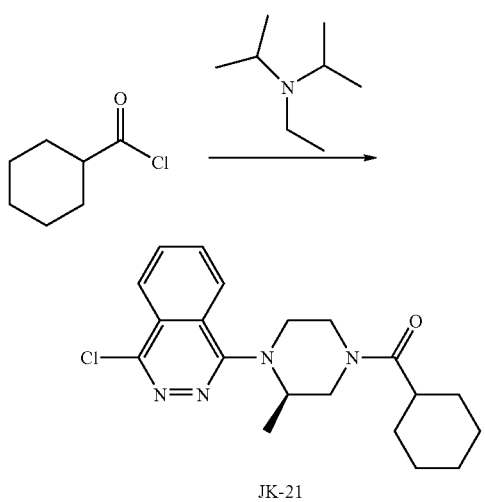

JK-21

(R)-1-chloro-4-(2-methylpiperazin-1-yl)phthalazine (JK-2, 752 mg, 2.86 mmol) was dissolved in DMF (8 mL) and N,N-diisopropylethylamine (1.5 mL). Cyclohexanecarbonyl chloride (0.498 mL, 3.72 mmol) was added and the mixture stirred at rt for 16 hours. The reaction was taken up in ethyl acetate (80 mL) and washed with aqueous K$_2$CO$_3$ (10%), water, and saturated sodium chloride. The organics were dried (MgSO$_4$) and evaporated to give a yellow oil. Chromatography over silica gel with a gradient of hexanes/0-75% ethyl acetate gave an off-white foam. MS (M+H)$^+$=373.1.

Example 26

Preparation of (R)-(3-methylpiperazin-1-yl)(phenyl)methanone (JK-22)

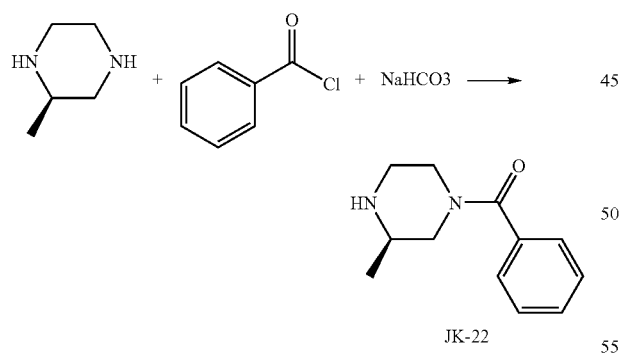

JK-22

(R)-2-methylpiperazine (13.85 g, 138 mmol), and sodium bicarbonate (52.3 g, 622 mmol) were dissolved/suspended in water (182 mL) and acetone (112 mL). The flask was cooled in an ice bath and a solution of benzoyl chloride (17.7 mL, 152 mmol) in acetone (56 mL) was added drop-wise over 1 hour. After 16 hours the acetone was removed on the rotovap. Water (400 mL) was added and the resulting mixture acidified using 6 M HCl to pH <2. The aqueous layer was washed with 200 mL CH$_2$Cl$_2$ three times. Aqueous sodium hydroxide (5M) was added to pH >12, and this solution was extracted three times with 200 mL of CH$_2$Cl$_2$. The combined organics were dried (MgSO$_4$) and evaporated to give a thick yellow oil. MS (M+H)$^+$=205.1

Example 27

Preparation of (R)-(4-(4-chloro-7-nitrophthalazin-1-yl)-3-methylpiperazin-1-yl)(phenyl)methanone and (R)-(4-(4-chloro-6-nitrophthalazin-1-yl)-3-methylpiperazin-1-yl)(phenyl)methanone (JK-23A and JK-24B)

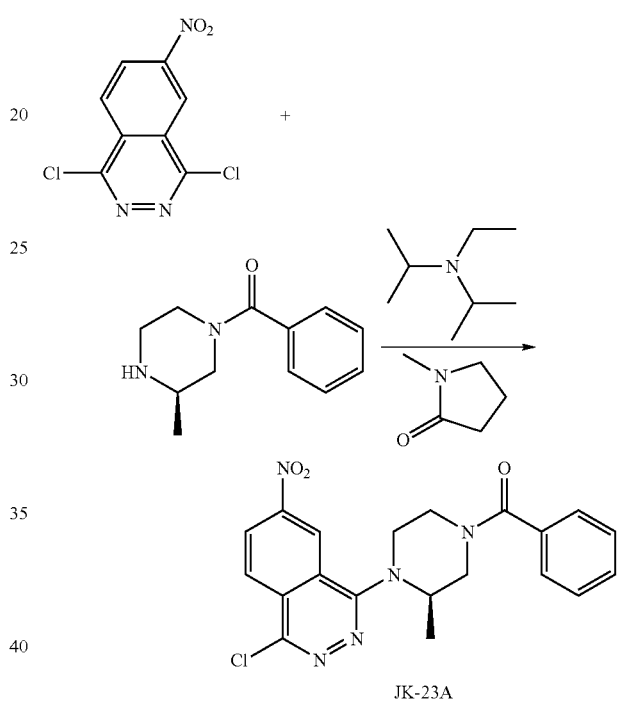

JK-23A

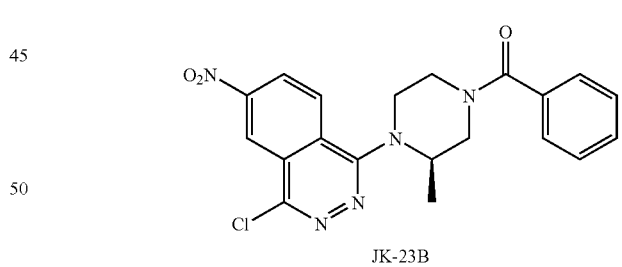

JK-23B 1,4-dichloro-6-nitrophthalazine (1.50 g, 6.147 mmol) and (R)-(3-methylpiperazin-1-yl)(phenyl)methanone (1381 mg, 6.761 mmol) were dissolved/suspended in N,N-diisopropylethylamine (2.14 mL) and N-methylpyrrolidinone (NMP) (2.50 mL), fitted with an argon balloon and heated at 100° C. for 5.5 hours. The reaction was taken up in ethyl acetate (80 mL) and washed with aqueous K$_2$CO$_3$ (10%), water, and saturated sodium chloride. The organics were dried (MgSO$_4$) and evaporated to give a brown oil. Chromatography over silica gel with a gradient of hexanes/0-70% ethyl acetate gave two products. Product JK-23A was an orange solid (906 mg);

product JK-23B was 380 mg of an orange solid. Both compounds had MS (M+H)⁺=412.9.

Example 28

Preparation of (R)-(4-(4-chloro-7-fluorophthalazin-1-yl)-3-methylpiperazin-1-yl)(phenyl)methanone (JK-24A) and (R)-(4-(4-chloro-6-fluorophthalazin-1-yl)-3-methylpiperazin-1-yl)(phenyl)methanone (JK-24B)

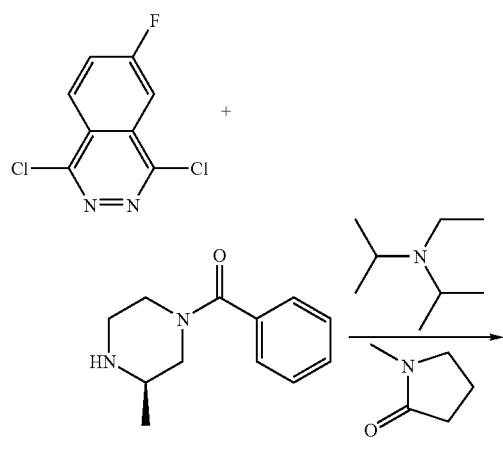

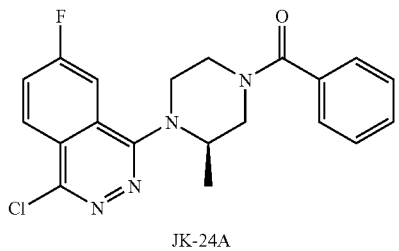
JK-24A

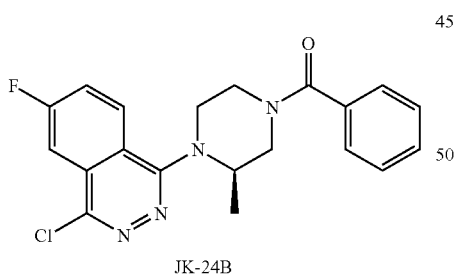
JK-24B 1,4-dichloro-6-fluorophthalazine (2.00 g, 9.22 mmol) and (R)-(3-methylpiperazin-1-yl)(phenyl)methanone (2.07 g, 10.1 mmol) were dissolved/suspended in N,N-diisopropylethylamine (3.21 mL) and NMP (4.00 mL), fitted with an argon balloon and heated at 100° C. for 4.5 hours. The reaction was taken up in ethyl acetate (80 mL) and washed with aqueous K₂CO₃ (10%), water, and saturated sodium chloride. The organics were dried (MgSO₄) and evaporated to give a brown oil. Chromatography over silica gel with a gradient of hexanes/0-80% ethyl acetate gave two products. Product JK-24A was a white solid 279 mg; product JK-24B was 123 mg of an white solid. Both compounds had MS (M+H)⁺=385.1.

Example 29

Preparation of (R)-(4-(4-chloro-7-cyanophthalazin-1-yl)-3-methylpiperazin-1-yl)(phenyl)methanone (JK-25A) and (R)-(4-(4-chloro-6-cyanophthalazin-1-yl)-3-methylpiperazin-1-yl)(phenyl)methanone (JK-25B)

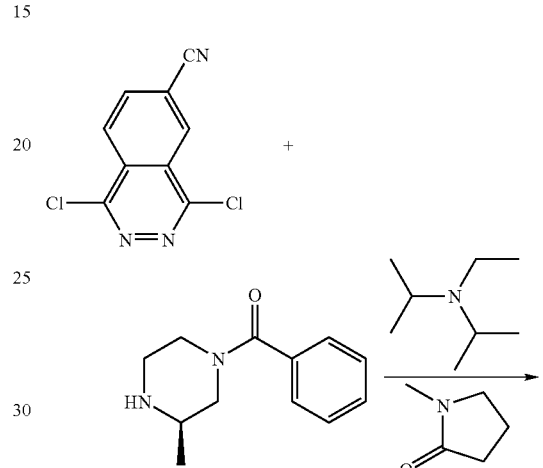

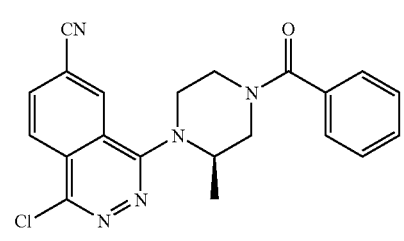
JK-25A

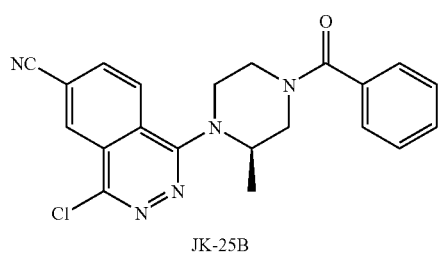
JK-25B 1,4-dichloro-6-cyanophthalazine (1.38 g, 6.16 mmol) and (R)-(3-methylpiperazin-1-yl)(phenyl)methanone (1.38 g, 6.78 mmol) were dissolved/suspended in N,N-diisopropylethylamine (2.15 mL) and NMP (3 mL), fitted with an argon balloon and heated at 100° C. for 4.5 hours. The reaction was taken up in ethyl acetate (80 mL) and washed with aqueous K₂CO₃ (10%), water, and saturated sodium chloride. The organics were dried (MgSO₄) and evaporated to give a brown oil. Chromatography over silica gel with a gradient of hexanes/0-70% ethyl acetate gave two products. Product JK-25A was a yellow solid 1.14 g; product JK-25B was 392 mg of a yellow solid. Both compounds had MS (M+H)⁺=385.1.

Example 30

Preparation of (S)-(4-(4-chloro-7-fluorophthalazin-1-yl)-2-methylpiperazin-1-yl)(phenyl)methanone (JK-26A) and (S)-(4-(4-chloro-6-fluorophthalazin-1-yl)-2-methylpiperazin-1-yl)(phenyl)methanone (JK-26B)

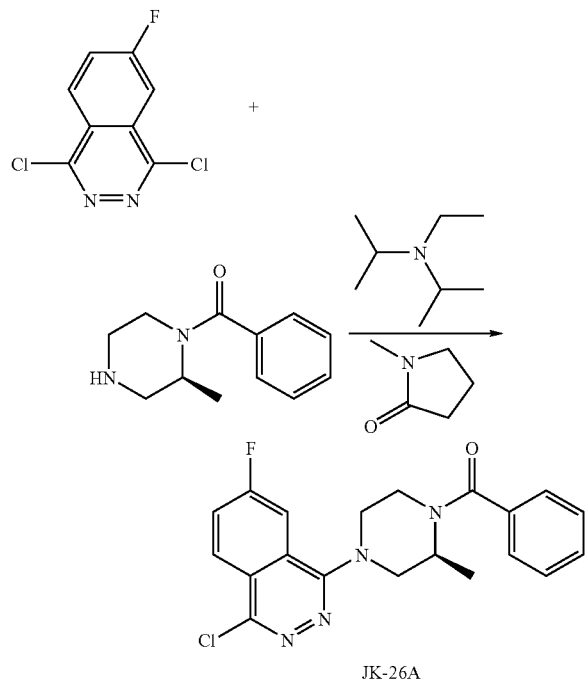

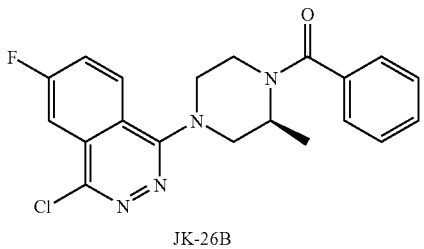

JK-26B 1,4-dichloro-6-fluorophthalazine (2.00 g, 9.22 mmol) and (S)-(2-methylpiperazin-1-yl)(phenyl)methanone (2.07 g, 10.1 mmol) were dissolved/suspended in N,N-diisopropylethylamine (3.21 mL) and NMP (4.00 mL), fitted with an argon balloon, and heated at 100° C. for 4.5 hours. The reaction was taken up in ethyl acetate (80 mL) and washed with aqueous $K_2CO_3$ (10%), water, and saturated sodium chloride. The organics were dried ($MgSO_4$) and evaporated to give a brown oil. Chromatography over silica gel with a gradient of hexanes/0-80% ethyl acetate gave two products. Product JK-26A was a white solid, 304 mg; product JK-26B was 179 mg of a white solid. Both compounds had MS (M+H)⁺=385.1.

Example 31

The compounds summarized in Table 2 were prepared as described in general Method B and in more detail in Example 7 substituting substrates as indicated.

TABLE 2

| Comp # | Name | Structure | M Calc'd | M + 1 found | Substrate | Boronic acid |
|---|---|---|---|---|---|---|
| 5 | (S)-(2-methyl-4-(4-phenylphthalazin-1-yl)piperazin-1-yl)(phenyl)-methanone | 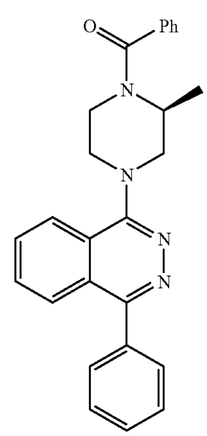 | 408.2 | 409.1 | (S)-JK-3 | Phenylboronic acid |

TABLE 2-continued

| Comp # | Name | Structure | M Calc'd | M + 1 found | Substrate | Boronic acid |
|---|---|---|---|---|---|---|
| 6 | (R)-(2-methyl-4-(4-phenylphthalazin-1-yl)piperazin-1-yl)(phenyl)-methanone | 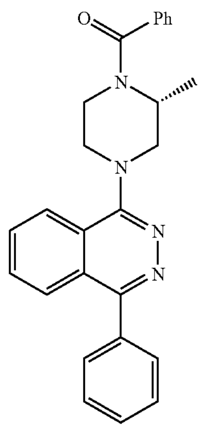 | 408.2 | 409.1 | (R)-JK-3 | Phenyl-boronic acid |
| 7 | (S)-(4-(4-(4-chlorophenyl)phthalazin-1-yl)-2-methylpiperazin-1-yl)(phenyl)methanone | 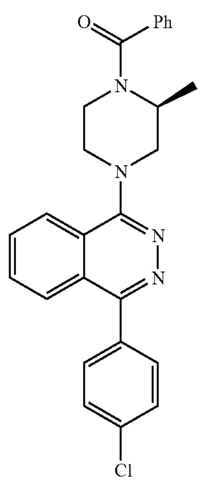 | 442.2 | 443.1 | (S)-JK-3 | 4-chloro-phenyl-boronic acid |
| 8 | (S)-(2-methyl-4-(4-p-tolylphthalazin-1-yl)piperazin-1-yl)(phenyl)methanone | 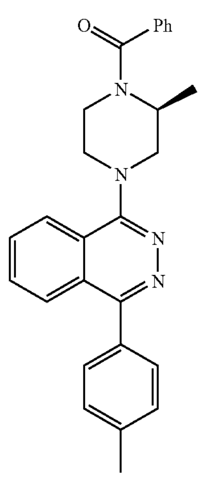 | 422.2 | 423.3 | (S)-JK-3 | p-tolyl-boronic acid |

TABLE 2-continued

| Comp # | Name | Structure | M Calc'd | M + 1 found | Substrate | Boronic acid |
|---|---|---|---|---|---|---|
| 9 | ((S)-4-(4-(3,4-dichlorophenyl)-phthalazin-1-yl)-2-methylpiperazin-1-yl)(phenyl)-methanone | 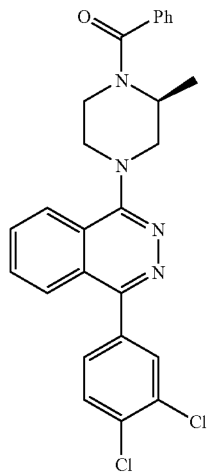 | 476.1 | 477.1 | (S)-JK-3 | 3,4-dichloro-phenyl-boronic acid |
| 10 | (S)-(3-methyl-4-(4-phenylphthalazin-1-yl)piperazin-1-yl)(phenyl)-methanone | 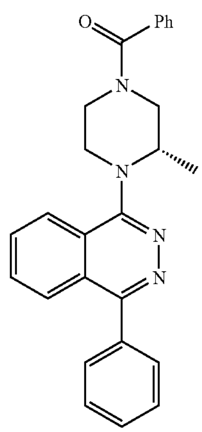 | 408.2 | 409.1 | (S)-JK-2 | Phenyl-boronic acid |
| 11 | (cis-2,6-dimethyl-4-(4-phenylphthalazin-1-yl)piperazin-1-yl)(phenyl)-methanone | 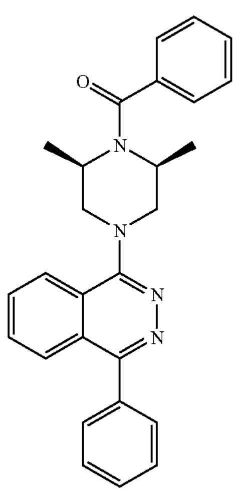 | 422.2 | 423.3 | BSL-6 | Phenyl-boronic acid |

Example 32

The compounds summarized in Table 3 were prepared as described in general Method B and in detail in Example 7 using the substrate as indicated, phenylboronic acid, and an appropriate acid chloride.

TABLE 3

| Comp # | Name | Structure | M Calc'd | M + 1 found | Precursor | Acid chloride |
|---|---|---|---|---|---|---|
| 12 | (S)-(2-methyl-4-(4-phenylphthalazin-1-yl)piperazin-1-yl)(pyridin-3-yl)methanone | 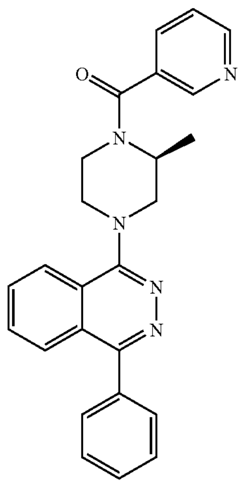 | 409.2 | 410.1 | JK-8 | Nicotinoyl chloride |
| 13 | (S)-(2-methyl-4-(4-phenylphthalazin-1-yl)piperazin-1-yl)(pyridin-4-yl)methanone | 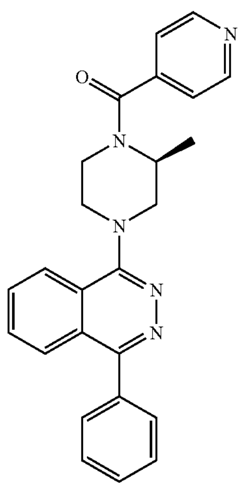 | 409.2 | 410.2 | JK-8 | Isonicotinoyl chloride |
| 14 | (S)-(2-methyl-4-(4-phenylphthalazin-1-yl)piperazin-1-yl)(thiazol-2-yl)methanone | 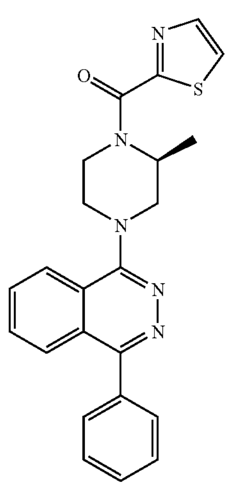 | 415.2 | 416.3 | JK-8 | 2-thiazolyl carbonyl chloride |

TABLE 3-continued

| Comp # | Name | Structure | M Calc'd | M + 1 found | Precursor | Acid chloride |
|---|---|---|---|---|---|---|
| 15 | (R)-cyclopentyl(3-methyl-4-(4-phenylphthalazin-1-yl)piperazin-1-yl)methanone | 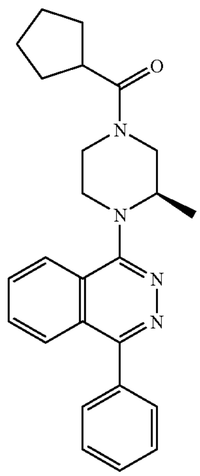 | 400.2 | 401.1 | JK-10 | Cyclopentanecarbonyl chloride |
| 16 | (R)-cyclopropyl(3-methyl-4-(4-phenylphthalazin-1-yl)piperazin-1-yl)methanone | 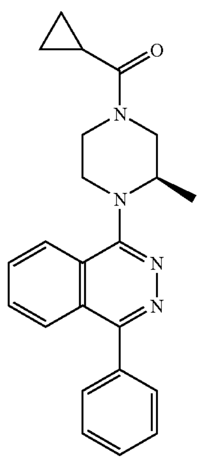 | 372.2 | 373.1 | JK-10 | Cyclopropanecarbonyl chloride |
| 17 | (R)-cyclohexyl(3-methyl-4-(4-phenylphthalazin-1-yl)piperazin-1-yl)methanone | 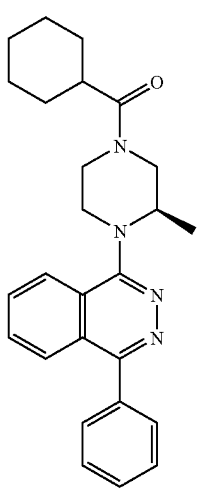 | 414.2 | 415.2 | JK-10 | Cyclohexanecarbonyl chloride |

Example 33

Preparation of ((S)-2-methyl-4-(4-(pyridin-2-yl)phthalazin-1-yl)piperazin-1-yl)(phenyl)methanone (18)

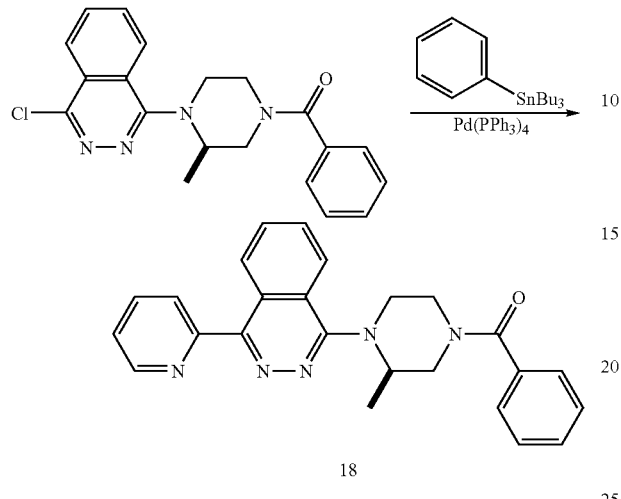

Compound 18 was prepared as described in general Method C. To (R)-(4-(4-chlorophthalazin-1-yl)-3-methylpiperazin-1-yl)(phenyl)methanone (0.150 g, 0.409 mmol) (JK-5) and tetrakis(triphenylphosphine)palladium (0.0236 g, 0.0204 mmol) was added degassed toluene under argon atmosphere. To the solution was added in ⅓ portions 2-tri-n-butylstannylpyridine (0.301 mL, 0.818 mmol) over a period of 30 min. The reaction was brought to 100° C. and stirred for 16 h. The cooled reaction was stirred with 4 mL of saturated aqueous potassium fluoride solution for 1 h, diluted with water (10 mL) and extracted with 10% MeOH in CH$_2$Cl$_2$ (3×30 mL). The combined organics were dried with Na$_2$SO$_4$ and concentrated in vacuo. The crude material was purified by column chromatography (40 g column, gradient of 50 to 100% ethyl acetate in hexanes with 2.5% TEA additive) to yield compound 18. MS (M+H)$^+$=410.2.

Example 34

Synthesis of ((R)-3-methyl-4-(4-(pyridin-2-yl)phthalazin-1-yl)piperazin-1-yl)(phenyl)methanone (19)

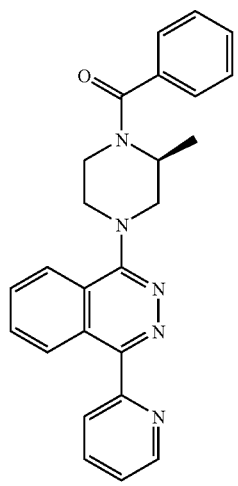

((R)-3-methyl-4-(4-(pyridin-2-yl)phthalazin-1-yl)piperazin-1-yl)(phenyl)methanone 19 was prepared via the same route as compound 18, using JK-4 substrate and 2-tri-n-butylstannylpyridine. MS (M+H)$^+$=410.2.

Example 35

Preparation of (R)-(3-methyl-4-(4-p-tolylphthalazin-1-yl)piperazin-1-yl)(phenyl)methanone (20)

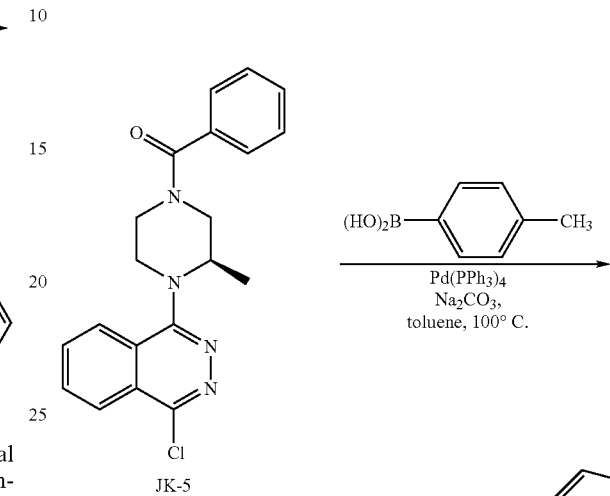

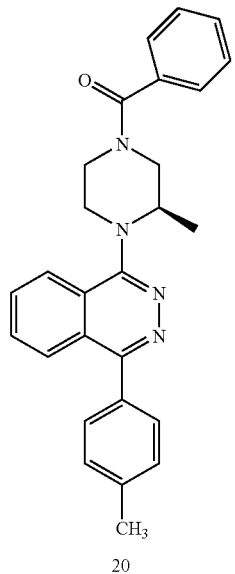

Compound 20 was prepared as described generally in synthetic Method D. Substrate JK-5 was prepared as described in detail in Example 11. To a reaction flask was added (R)-(4-(4-chlorophthalazin-1-yl)-3-methylpiperazin-1-yl)(phenyl)methanone (JK-5) (200 mg, 0.54 mmol), p-tolyl boronic acid (111 mg, 0.82 mmol, 1.5 eq), and Pd(PPh$_3$)$_4$ (31 mg, 0.027 mmol, 0.05 eq). The flask was fitted with a reflux condenser and purged with nitrogen. Toluene (5.4 mL) and aqueous Na$_2$CO$_3$ (2 M, 0.54 mL, 2 eq) were added and the reaction was heated to 100° C. overnight. The reaction was then cooled to rt and diluted with 75 mL of ethyl acetate. The organic phase was washed with 1×10 mL of sat. NaHCO$_3$ solution, 1×10 mL of H$_2$O, and 1×10 mL of sat. NaCl solution. The organic layer was dried over MgSO$_4$, filtered, and concentrated in vacuo. Purification by column chromatography (60% ethyl acetate in hexanes) afforded 197 mg (86%) of (R)-(3-methyl-4-(4-p-tolylphthalazin-1-yl)piperazin-1-yl)(phenyl)methanone 20 MS (M+H)$^+$=423.3.

Example 36

The compounds summarized in Table 3 were prepared according to general Method D and as described in more detail in Example 35 using the appropriate substrates as indicated below.

TABLE 3

| Comp # | Name | Structure | M Calc'd | M + 1 found | Substrate | Boronic acid |
|---|---|---|---|---|---|---|
| 21 | (R)-(4-(4-(4-chlorophenyl)-phthalazin-1-yl)-3-methylpiperazin-1-yl)(phenyl)-methanone | 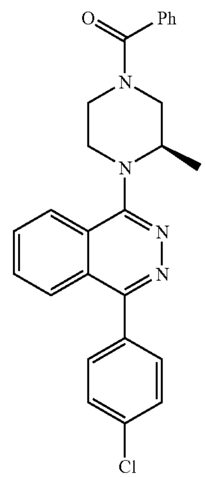 | 442.2 | 443.0 | JK-5 | 4-chloro-phenyl-boronic acid |
| 22 | (R)-(4-(4-(4-tert-butylphenyl)-phthalazin-1-yl)-3-methyl-piperazin-1-yl)(phenyl)-methanone | 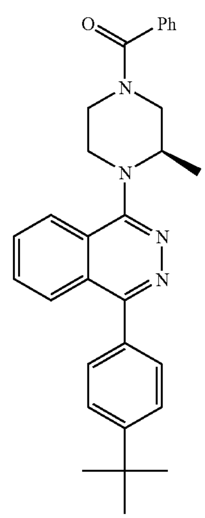 | 464.3 | 465.2 | JK-5 | 4-tert-butyl-phenyl-boronic acid |

TABLE 3-continued

| Comp # | Name | Structure | M Calc'd | M + 1 found | Substrate | Boronic acid |
|---|---|---|---|---|---|---|
| 23 | (R)-(3-methyl-4-(4-(4-(trifluoromethyl)-phenyl)-phthalazin-1-yl)piperazin-1-yl)(phenyl)-methanone | 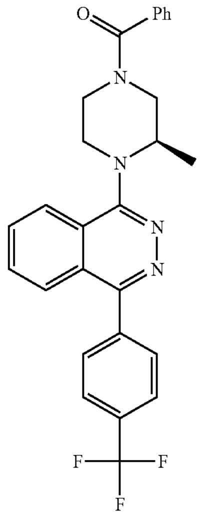 | 476.2 | 477.1 | JK-5 | 4-trifluoro-methyl phenyl-boronic acid |
| 24 | (R)-(4-(4-(4-isopropylphenyl)-phthalazin-1-yl)-3-methylpiperazin-1-yl)(phenyl)-methanone | 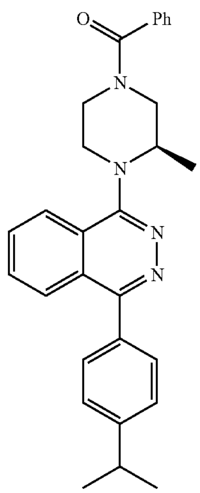 | 450.2 | 451.3 | JK-5 | 4-isopropyl-phenyl boronic acid |
| 25 | ((R)-4-(4-(benzofuran-2-yl)phthalazin-1-yl)-3-methylpiperazin-1-yl)(phenyl)-methanone | 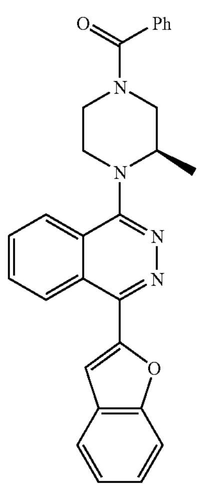 | 448.2 | 449.2 | JK-5 | benzo[b]furan-2-boronic acid |

TABLE 3-continued

| Comp # | Name | Structure | M Calc'd | M + 1 found | Substrate | Boronic acid |
|---|---|---|---|---|---|---|
| 26 | Racemic trans-2,5-dimethyl-4-(4-phenylphthalazin-1-yl)piperazin-1-yl)(phenyl)methanone | 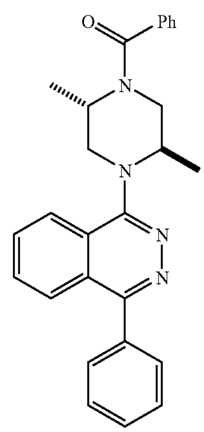 | 422.2 | 423.1 | BSL-5 | Phenyl boronic acid |
| 27 | ((2S,5R)-2,5-dimethyl-4-(4-phenylphthalazin-1-yl)piperazin-1-yl)(phenyl)methanone | 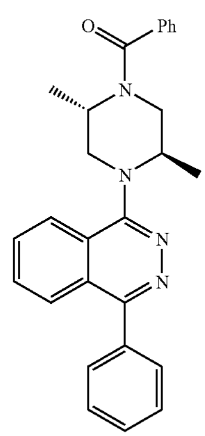 | 422.2 | 423.1 | BSL-5 (enantiopure) | Phenyl boronic acid |
| 28 | ((2R,5S)-2,5-dimethyl-4-(4-phenylphthalazin-1-yl)piperazin-1-yl)(phenyl)methanone | 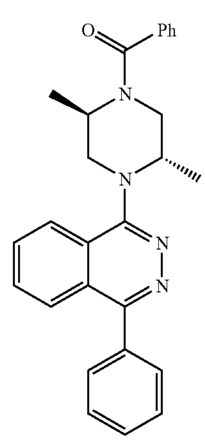 | 422.2 | 423.1 | BSL-5 (enantiopure) | Phenyl boronic acid |

TABLE 3-continued

| Comp # | Name | Structure | M Calc'd | M + 1 found | Substrate | Boronic acid |
|---|---|---|---|---|---|---|
| 29 | Racemic trans-2,5-dimethyl-4-(4-(4-(trifluoromethyl)-phenyl)-phthalazin-1-yl)piperazin-1-yl)(phenyl)methanone | 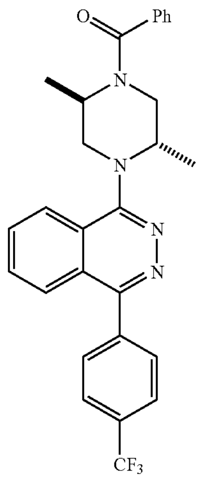 | 490.2 | 491.2 | BSL-5 | 4-trifluoro-methyl-phenyl boronic acid |
| 30 | (S)-(2-methyl-4-(4-(4-(trifluoromethyl)phenyl)phthalazin-1-yl)piperazin-1-yl)(phenyl)methanone | 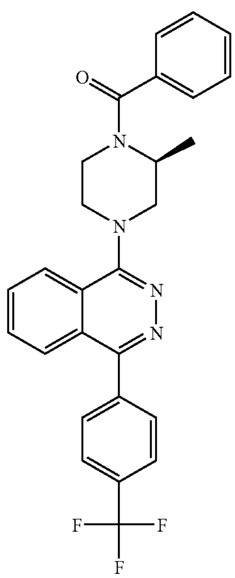 | 476.2 | 477.2 | JK-4 | 4-(trifluoro-methyl) phenyl boronic acid |
| 31 | (S)-(2-methyl-4-(4-(4-vinylphenyl)phthalazin-1-yl)piperazin-1-yl)(phenyl)methanone | 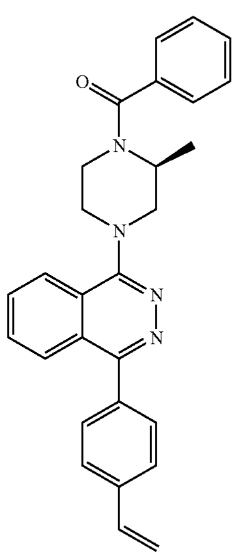 | 434.2 | 435.2 | JK-4 | 4-vinyl-benzene-boronic acid |

TABLE 3-continued

| Comp # | Name | Structure | M Calc'd | M + 1 found | Substrate | Boronic acid |
|---|---|---|---|---|---|---|
| 32 | ((S)-4-(4-(2-fluoro-4-methylphenyl)phthalazin-1-yl)-2-methylpiperazin-1-yl)(phenyl)methanone | 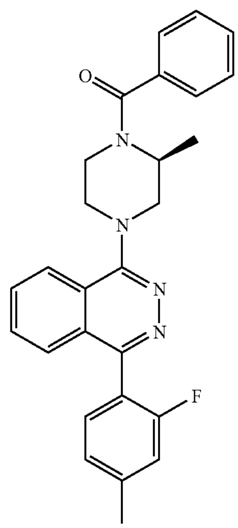 | 440.2 | 441.2 | JK-4 | 2-fluoro-4-methyl-boronic acid |
| 33 | ((S)-4-(4-(3-fluoro-4-methylphenyl)phthalazin-1-yl)-2-methylpiperazin-1-yl)(phenyl)methanone | 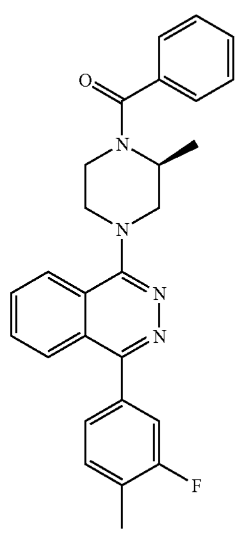 | 440.2 | 441.2 | JK-4 | 3-fluoro-4-methyl-boronic acid |
| 34 | ((S)-4-(4-(2-fluorophenyl)phthalazin-1-yl)-2-methylpiperazin-1-yl)(phenyl)methanone | 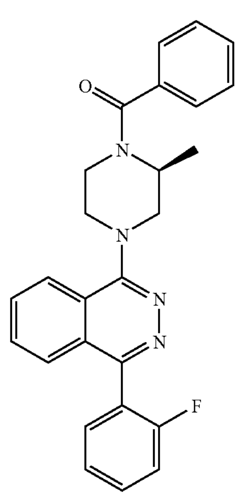 | 426.2 | 427.3 | JK-4 | 2-fluoro-phenyl-boronic acid |

TABLE 3-continued

| Comp # | Name | Structure | M Calc'd | M + 1 found | Substrate | Boronic acid |
|---|---|---|---|---|---|---|
| 35 | ((R)-4-(4-(2-fluoro-4-methylphenyl)phthalazin-1-yl)-3-methylpiperazin-1-yl)(phenyl)methanone | 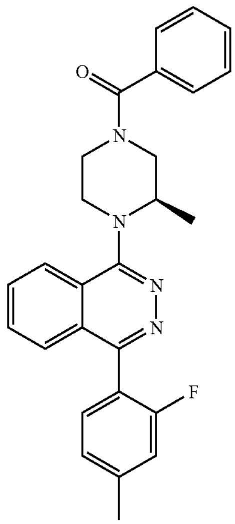 | 440.2 | 441.2 | JK-5 | 2-fluoro-4-methyl-boronic acid |
| 36 | ((R)-4-(4-(3-fluoro-4-methylphenyl)phthalazin-1-yl)-3-methylpiperazin-1-yl)(phenyl)methanone | 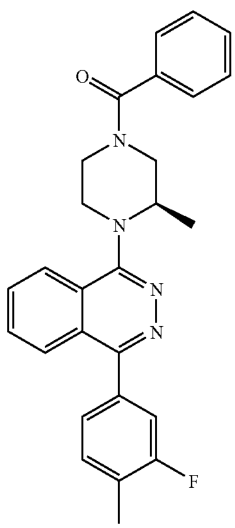 | 440.2 | 441.2 | JK-5 | 3-fluoro-4-methyl-boronic acid |
| 37 | ((R)-4-(4-(4-chloro-2-fluorophenyl)phthalazin-1-yl)-3-methylpiperazin-1-yl)(phenyl)methanone | 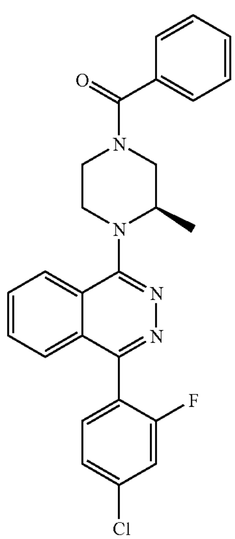 | 460.2 | 461.3 | JK-5 | 4-chloro-2-fluorophenyl-boronic acid |

TABLE 3-continued

| Comp # | Name | Structure | M Calc'd | M + 1 found | Substrate | Boronic acid |
|---|---|---|---|---|---|---|
| 38 | ((S)-4-(4-(4-chloro-2-fluorophenyl)phthalazin-1-yl)-2-methylpiperazin-1-yl)(phenuyl)methanone | 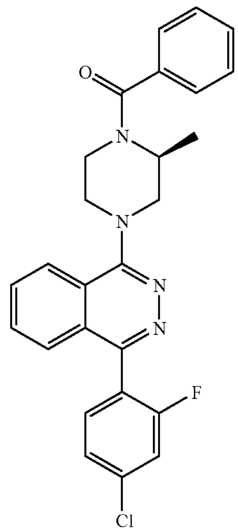 | 460.2 | 461.2 | JK-4 | 4-chloro-2-fluorophenyl-boronic acid |
| 39 | ((R)-4-(4-(2-fluorophenyl)phthalazin-1-yl)-3-methylpiperazin-1-yl)(phenyl)methanone | 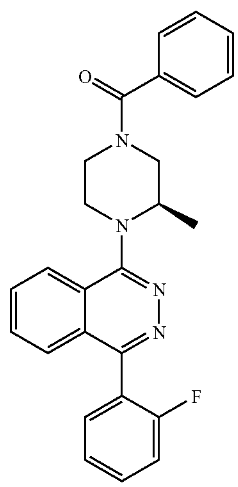 | 426.2 | 427.3 | JK-5 | 2-fluorophenyl-boronic acid |
| 40 | 1-benzyl-4-(4-(4-(trifluoromethyl)phenyl)phthalazin-1-yl)piperazin-2-one | 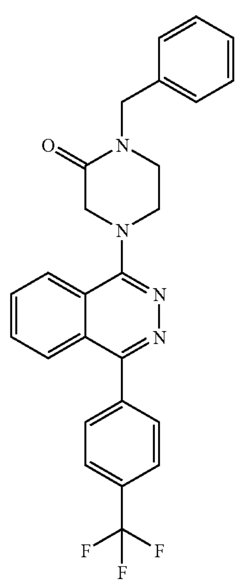 | 462.2 | 463.1 | JK-15 | 4-(trifluoromethyl)phenyl boronic acid |

TABLE 3-continued
| Comp # | Name | Structure | M Calc'd | M + 1 found | Substrate | Boronic acid |
|---|---|---|---|---|---|---|
| 41 | (R)-(4-(4-(4-fluorophenyl)phthalazin-1-yl)-3-methylpiperazin-1-yl)(phenyl)methanone | 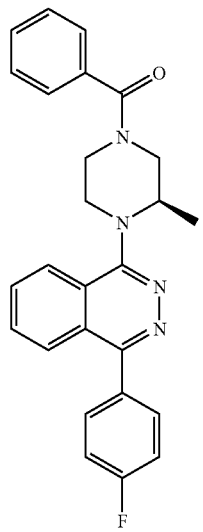 | 426.2 | 427.2 | JK-5 | 4-fluorophenyl-boronic acid |
| 42 | (R)-methyl 4-(4-(4-benzoyl-2-methylpiperazin-1-yl)phthalazin-1-yl)benzoate | 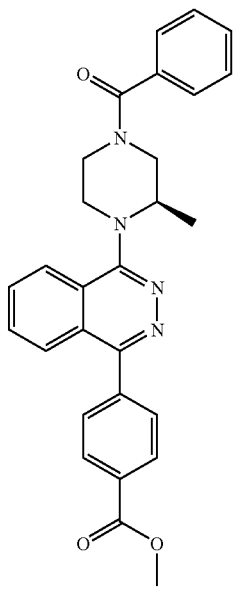 | 466.2 | 467.1 | JK-5 | 4-carboxy methylphenyl-boronic acid |

TABLE 3-continued

| Comp # | Name | Structure | M Calc'd | M + 1 found | Substrate | Boronic acid |
|---|---|---|---|---|---|---|
| 43 | (R)-(4-(4-(4-(dimethylamino)phenyl)phthalazin-1-yl)-3-methylpiperazin-1-yl)(phenyl)methanone | 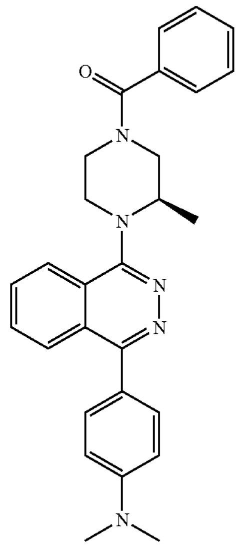 | 451.2 | 452.3 | JK-5 | 4-(dimethyl-amino)phenyl boronic acid |
| 44 | methyl 1-benzoyl-4-(4-phenylphthalazin-1-yl)piperazine-2-carboxylate | 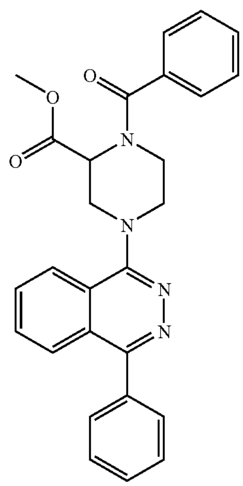 | 452.2 | 453.2 | JK-18 | Phenyl-boronic acid |
| 45 | ((2S,5S)-2,5-dimethyl-4-(4-phenylphthalazin-1-yl(piperazin-1-yl)(phenyl)methanone | 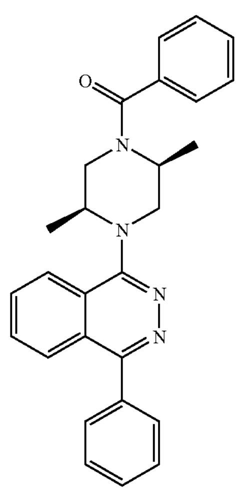 | 422.2 | 423.2 | JK-20 | Phenyl-boronic acid |

TABLE 3-continued

| Comp # | Name | Structure | M Calc'd | M + 1 found | Substrate | Boronic acid |
|---|---|---|---|---|---|---|
| 46 | (R)-4-(4-(4-benzoyl-2-methylpiperazin-1-yl)phthalazin-1-yl)benzonitrile | 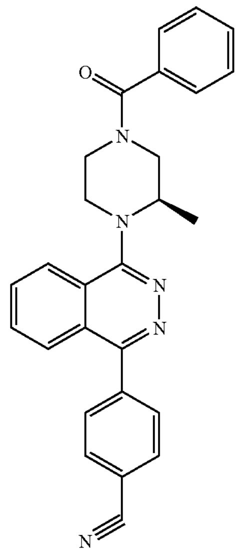 | 433.2 | 343.2 | JK-5 | 4-cyano-phenyl-boronic acid |
| 47 | (R)-(4-(4-(4-(hydroxymethyl)phenyl)phthalazin-1-yl)-3-methylpiperazin-1-yl)(phenyl)methanone | 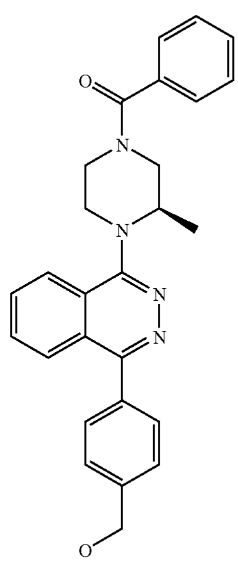 | 438.2 | 439.2 | JK-5 | 4-(Hydroxy-methyl)phenyl boronic acid |

TABLE 3-continued

| Comp # | Name | Structure | M Calc'd | M + 1 found | Substrate | Boronic acid |
|---|---|---|---|---|---|---|
| 48 | (R)-(3-methyl-4-(4-(4-morpholinophenyl)phthalazin-1-yl)piperazin-1-yl)(phenyl)methanone | 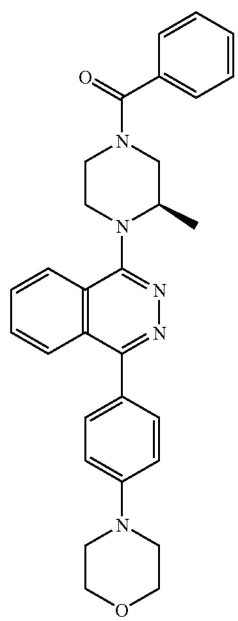 | 493.2 | 494.1 | JK-5 | 4-morpholinophenylboronic acid |
| 49 | (R)-(4-(4-(4-hydroxyphenyl)phthalazin-1-yl)-3-methylpiperazin-1-yl)(phenyl)methanone | 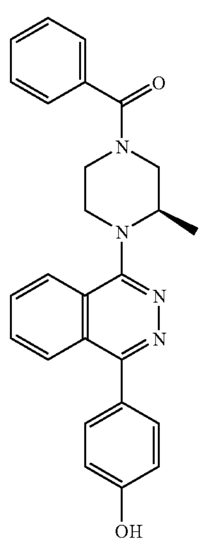 | 424.2 | 425.4 | JK-5 | 4-hydroxyphenylboronic acid |

TABLE 3-continued

| Comp # | Name | Structure | M Calc'd | M + 1 found | Substrate | Boronic acid |
|---|---|---|---|---|---|---|
| 50 | (R)-cyclohexyl(4-(4-(4-fluorophenyl)phthalazin-1-yl)-3-methylpiperazin-1-yl)methanone | 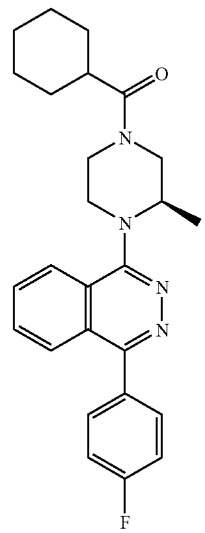 | 432.2 | 433.2 | JK-21 | 4-fluoro-phenyl-boronic acid |
| 51 | (R)-(3-methyl-4-(7-nitro-4-phenylphthalazin-1-yl)piperazin-1-yl)(phenyl)methanone | 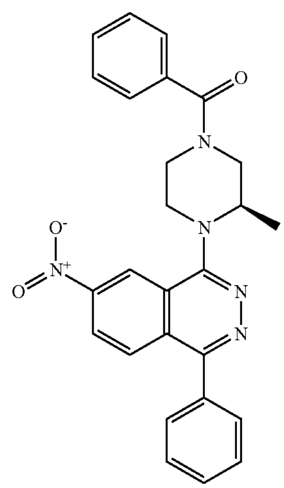 | 453.2 | 454.1 | JK-23A | Phenyl-boronic acid |
| 52 | (R)-(3-methyl-4-(6-nitro-4-phenylphthalazin-1-yl)piperazin-1-yl)(phenyl)methanone | 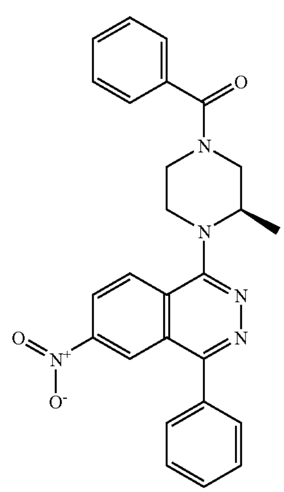 | 453.2 | 454.1 | JK-23B | Phenyl-boronic acid |

TABLE 3-continued

| Comp # | Name | Structure | M Calc'd | M + 1 found | Substrate | Boronic acid |
|---|---|---|---|---|---|---|
| 53 | (R)-cyclohexyl(4-(4-(4-(hydroxymethyl)phenyl)phthalazin-1-yl)-3-methylpiperazin-1-yl)methanone | 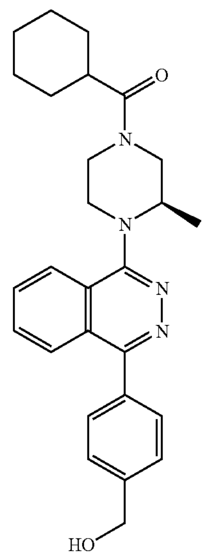 | 444.2 | 445.3 | JK-21 | 4-(Hydroxymethyl)phenyl boronic acid |
| 54 | (R)-(4-(7-fluoro-4-phenylphthalazin-1-yl)-3-methylpiperazin-1-yl)(phenyl)methanone | 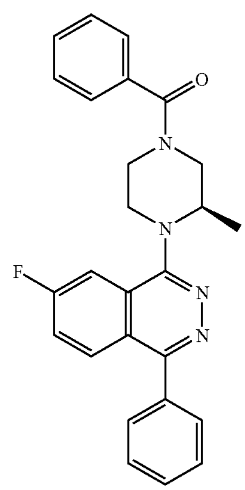 | 426.2 | 427.2 | JK-24A | Phenylboronic acid |
| 55 | (R)-(4-(6-fluoro-4-phenylphthalazin-1-yl)-3-methylpiperazin-1-yl)(phenyl)methanone | 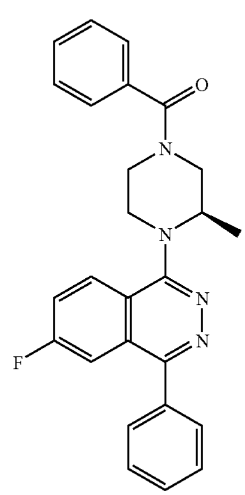 | 426.2 | 427.3 | JK-24B | Phenylboronic acid |

TABLE 3-continued

| Comp # | Name | Structure | M Calc'd | M + 1 found | Substrate | Boronic acid |
|---|---|---|---|---|---|---|
| 56 | (S)-(4-(6-fluoro-4-phenylphthalazin-1-yl)-2-methylpiperazin-1-yl)(phenyl)methanone | 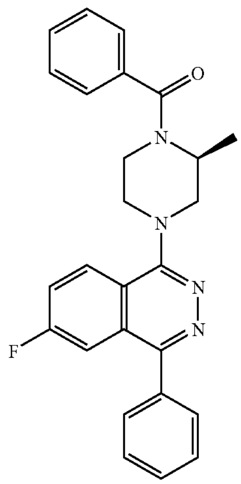 | 426.2 | 427.3 | JK-26 | Phenyl-boronic acid |
| 57 | (S)-(4-(4-cyclopropylphthalazin-1-yl)-2-methylpiperazin-1-yl)(phenyl)methanone | 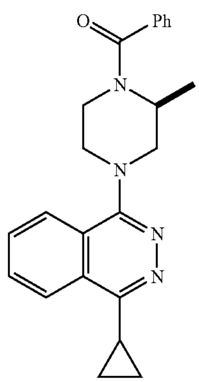 | 372.5 | 373.1 | JK-4 | Cyclopropyl boronic acid |
| 58 | (S)-(2-methyl-4-(4-(pyridin-4-yl)phthalazin-1-yl)piperazin)-1-yl)(phenyl)methanone | 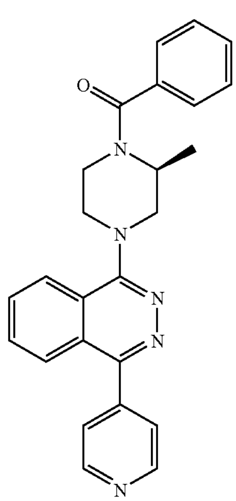 | 409.5 | 410.2 | JK-4 | 4-pyridyl boronic acid |

TABLE 3-continued

| Comp # | Name | Structure | M Calc'd | M + 1 found | Substrate | Boronic acid |
|---|---|---|---|---|---|---|
| 59 | (R)-(3-methyl-4-(4-pyridin-4-yl)phthalzin-1-yl)piperazin-1-yl)(phenyl)methanone | 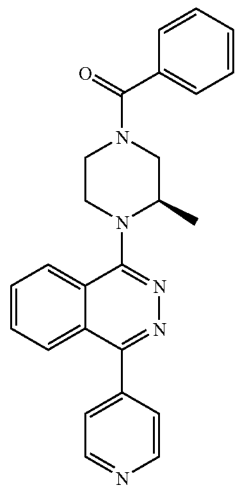 | 409.5 | 410.2 | JK-5 | 4-pyridyl boronic acid |
| 60 | ((2S,5R)-4-(4-(hydroxymethyl)phenyl)phthalazin-1-yl)-2,5-dimethylpiperazin-1-yl)(phenyl)methanone | 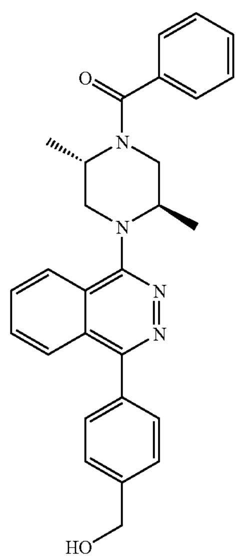 | 452.6 | 453.1 | Enantiomerically pure BSL-5 | 4-(hydroxymethyl)phenyl boronic acid |
| 61 | ((2R,5S)-4-(4-(hydroxymethyl)phenyl)phthalazin-1-yl)-2,5-dimethylpiperazin-1-yl)(phenyl)methanone | 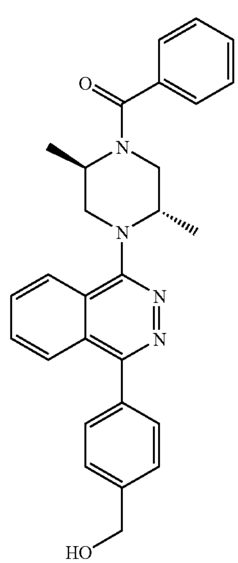 | 452.6 | 453.1 | Enantiomerically pure BSL-5 | 4-(hydroxymethyl)phenyl boronic acid |

TABLE 3-continued

| Comp # | Name | Structure | M Calc'd | M + 1 found | Substrate | Boronic acid |
|---|---|---|---|---|---|---|
| 62 | ((2S,5R)-4-(4-(4-chloro-2-fluorophenyl)phthalazin-1-yl)-2,5-dimethylpiperazin-1-yl)(phenyl)methanone | 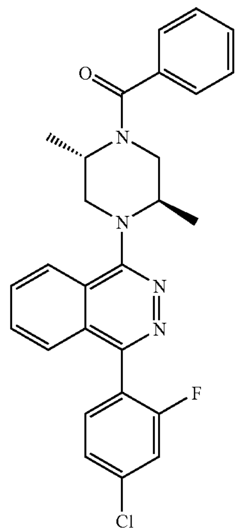 | 474.2 | 475.1 | Enantiomerically pure BSL-5 | 4-chloro-2-fluoro-phenyl-boronic acid |
| 63 | ((2R,5S)-4-(4-(4-chloro-2-fluorophenyl)phthalazin-1-yl)-2,5-dimethylpiperazin-1-yl)(phenyl)methanone | 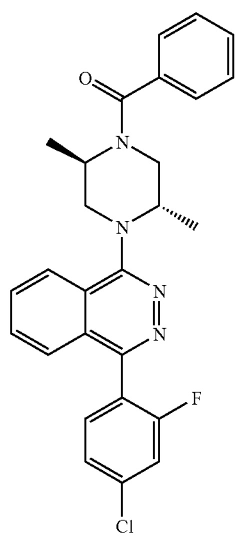 | 474.2 | 475.1 | Enantiomerically pure BSL-5 | 4-chloro-2-fluoro-phenyl-boronic acid |
| 64 | (2,2-dimethyl-4-(4-phenylphthalazin-1-yl)piperazin-1-yl)(phenyl)methanone | 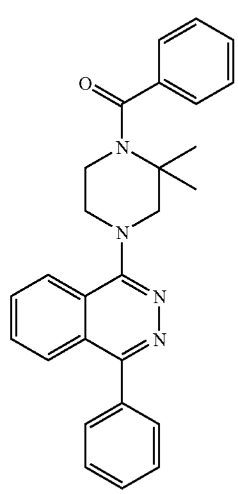 | 422.2 | 423.3 | BSL-7 | Phenyl boronic acid |

TABLE 3-continued

| Comp # | Name | Structure | M Calc'd | M + 1 found | Substrate | Boronic acid |
|---|---|---|---|---|---|---|
| 65 | (R)-4-(4-(4-(4,4-difluorocyclohexanecarbonyl)-2-methylpiperazin-1-yl)phthalazin-1-yl)benzonitrile | 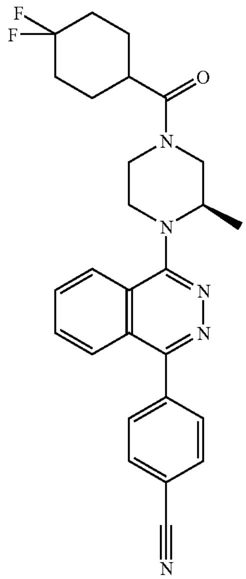 | 475.2 | 476.2 | JK-27 | 4-cyanophenyl |

Example 37

Preparation of (R)-(3-methyl-4-(4-morpholinophthalazin-1-yl)piperazin-1-yl)(phenyl)methanone (66)

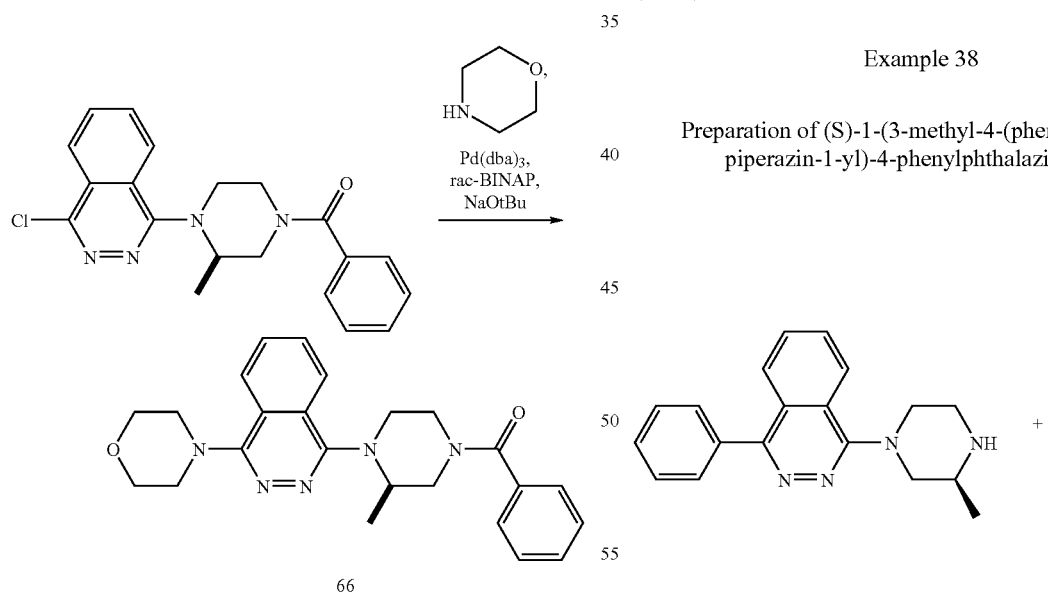

66

Compound 66 was prepared as described in general method E. Sodium t-butoxide (0.0550 g, 0.572 mmol), rac-2,2-bis(diphenylphosphino)-1,1-binaphthalene (0.0102 g, 0.0164 mmol), tris(dibenzylideneacetone)dipalladium (0) (0.00749 g, 0.00818 mmol), and (R)-(4-(4-chlorophthalazin-1-yl)-3-methylpiperazin-1-yl)(phenyl)methanone JK-5 (0.150 g, 0.409 mmol) were combined in a screw cap vial, purged to argon, and solvated with degassed morpholine (0.142 mL, 1.64 mmol). The reaction vial was sealed and stirred at 80° C. After 16 h, the reaction was taken up in dichloromethane and directly loaded onto silica gel. Purification by column chromatography (gradient elution 40 to 100% ethyl acetate in hexanes) afforded 66. MS (M+H)$^+$=418.1.

Example 38

Preparation of (S)-1-(3-methyl-4-(phenylsulfonyl)piperazin-1-yl)-4-phenylphthalazine (67)

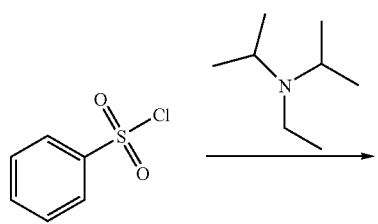

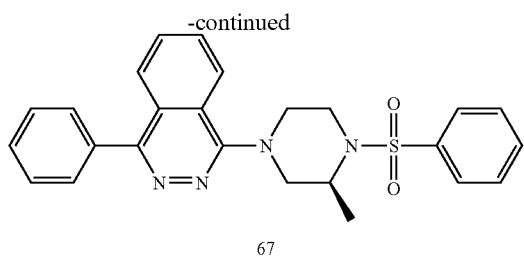

67

Compound 67 was prepared as described in general Method F. (S)-1-(3-methylpiperazin-1-yl)-4-phenylphthalazine (JK-8) (150 mg, 0.493 mmol) was dissolved in DMF (3 mL) and N,N-diisopropylethylamine (0.400 mL). Benzenesulfonyl chloride (104 mg, 0.591 mmol) was added and the reaction stirred at rt for 18 hours. The reaction was taken up in ethyl acetate (75 mL) and washed with aqueous $K_2CO_3$ (10%), water, and saturated sodium chloride. The organics were dried ($MgSO_4$) and evaporated to give a brown oil. Chromatography over silica gel with a gradient of hexanes/0-70% ethyl acetate gave 67 as an off-white solid. MS $(M+H)^+=445.2$

Example 39

Preparation of (R)-1-(2-methyl-4-(phenylsulfonyl)piperazin-1-yl)-4-phenylphthalazine (68)

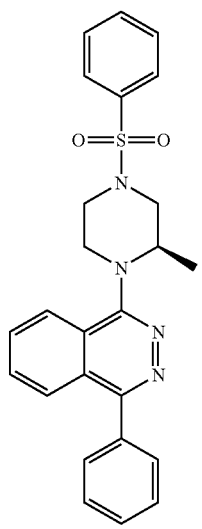

68

Compound 68 was prepared as described in Example 38 using JK-10 and benzene-sulfonyl chloride. MS $(M+H)^+=445.1$.

Example 40

Preparation of (R)-4-(2-methyl-1-(4-phenylphthalazin-1-yl)piperazine-4-carbonyl)cyclohexanone (69)

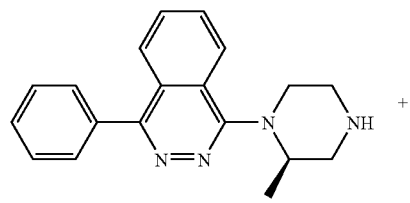

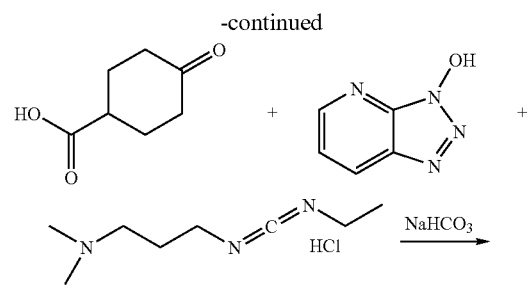

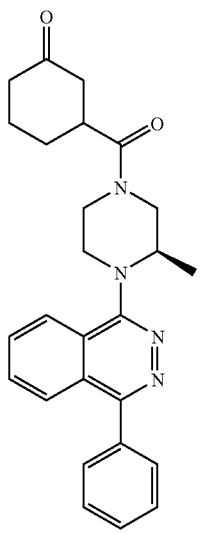

69

(R)-1-(2-methylpiperazin-1-yl)-4-phenylphthalazine (JK-10) (509 mg, 1.67 mmol), 4-oxocyclohexanecarboxylic acid (261 mg, 1.84 mmol), 3H-[1,2,3]triazolo[4,5-b]pyridin-3-ol (273 mg, 2.01 mmol) (HOAt), N1-((ethylimino)methylene)-N3,N3-dimethylpropane-1,3-diamine hydrochloride (385 mg, 2.01 mmol), sodium bicarbonate (281 mg, 3.34 mmol), and DMF (6 mL) were stirred at rt for 22 hours. The reaction was taken up in ethyl acetate (80 mL) and washed with aqueous $K_2CO_3$ (10%), water, and saturated sodium chloride. The organics were dried ($MgSO_4$) and evaporated to give a yellow oil. Chromatography over silica gel with a gradient of hexanes/0-70% ethyl acetate gave an off-white solid, compound 69. MS $(M+H)^+=429.2$.

Example 41

Preparation of 3-((R)-2-methyl-1-(4-phenylphthalazin-1-yl)piperazine-4-carbonyl)cyclohexanone (70)

70

Compound 70 was prepared as described in Example 40 using substrate JK-10 and 3-oxo-cyclohexane-carboxylic acid. MS (M+H)$^+$=429.2.

Example 42

Preparation of (R)-4-(4-(4-benzoyl-2-methylpiperazin-1-yl)phthalazin-1-yl)benzamide (71)

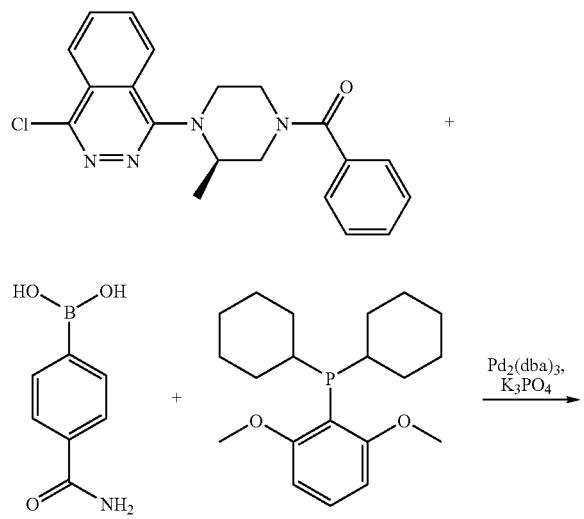

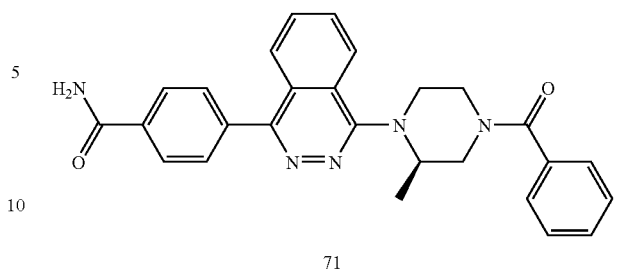

71

Compound 71 was prepared according to general method H. A 15 mL Schlenk tube was charged with (R)-(4-(4-chlorophthalazin-1-yl)-3-methylpiperazin-1-yl)(cyclohexyl)methanone JK-5 (130 mg, 349 μmol), 4-carbamoylphenylboronic acid (77 mg, 523 μmol), tris(dibenzylideneacetone)dipalladium (0) (3.2 mg, 3.5 μmol), dicyclohexyl(2,6-dimethoxyphenyl)phosphine (2.3 mg, 7.0 μmol), and potassium phosphate tribasic (148 mg, 697 μmol). The vessel was evacuated, backfilled with argon 5 times, and then previously degassed n-butanol (1 mL) was added. The reaction was heated at 100° C. for 20 hours. After cooling, the reaction was added to aqueous K$_2$CO$_3$ (10%) and extracted three times with dichloromethane. The combined organics were dried (MgSO$_4$) and evaporated to give a yellow oil. Chromatography over silica gel with a gradient of hexanes/0-100% ethyl acetate gave a pale yellow solid, compound 71. MS (M+H)$^+$=452.2.

Example 43

The compounds summarized in Table 4 were prepared as described in detail in Example 42 using the appropriate substrates as indicated.

TABLE 4

| Comp # | Name | Structure | M Calc'd | M + 1 found | Substrate | Boronic Acid |
|---|---|---|---|---|---|---|
| 72 | (R)-4-(4-(4-(cyclohexanecarbonyl)-2-methylpiperazin-1-yl)phthalazin-1-yl)benzonitrile | 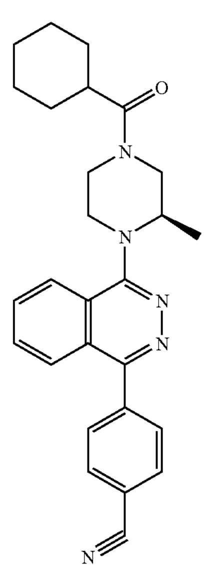 | 439.2 | 440.2 | JK-21 | 4-cyanophenylboronic acid |

TABLE 4-continued

| Comp # | Name | Structure | M Calc'd | M + 1 found | Substrate | Boronic Acid |
|---|---|---|---|---|---|---|
| 73 | ((S)-2-methyl-4-(4-(pyridin-3-yl)phthalazin-1-yl)piperazin-1-yl)(phenyl)methanone | 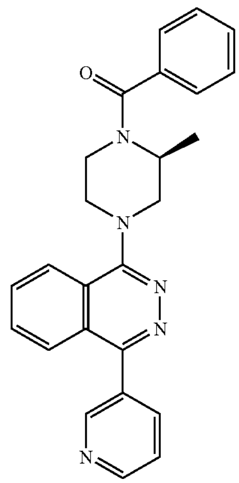 | 409.5 | 410.2 | JK-4 | 3-pyridyl boronic acid |
| 74 | ((R)-3-methyl-4-(4-(pyridin-3-yl)phthalazin-1-yl)piperazin-1-yl)(phenyl)methanone | 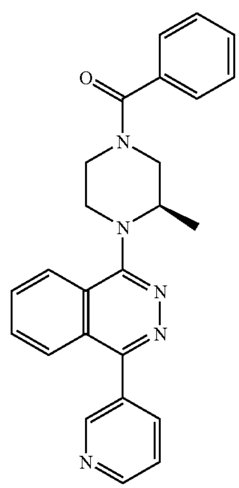 | 409.5 | 410.2 | JK-5 | 3-pyridyl boronic acid |
| 75 | 4-(4-((2R,5S)-4-benzoyl-2-5-dimethylpiperazin-1-yl)phthalazin-1-yl)benzonitrile | 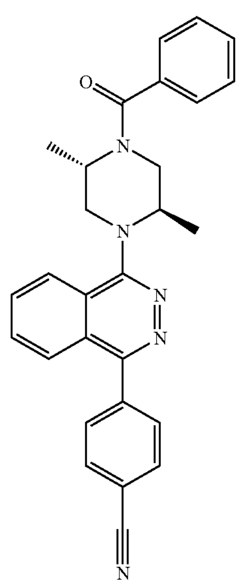 | 447.5 | 448.1 | Enantiopure BSL-5 | 4-cyanophenyl boronic acid |

TABLE 4-continued

| Comp # | Name | Structure | M Calc'd | M + 1 found | Substrate | Boronic Acid |
|---|---|---|---|---|---|---|
| 76 | 4-(4-((2S,5R)-4-benzoyl-2,5-dimethylpiperazin-1-yl)phthalazin-1-yl)benzonitrile | 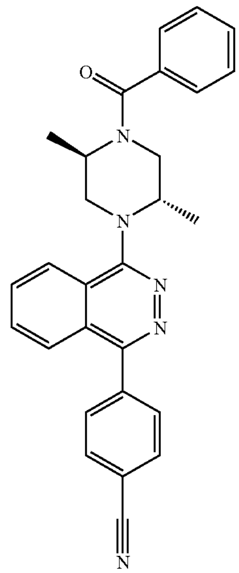 | 447.5 | 449.2 | Enantiopure BSL-5 | 4-cyanophenyl boronic acid |

Example 44

Preparation of ((S)-4-(4-(1H-imidazol-1-yl)phthalazin-1-yl)-2-methylpiperazin-1-yl)(phenyl)methanone (77)

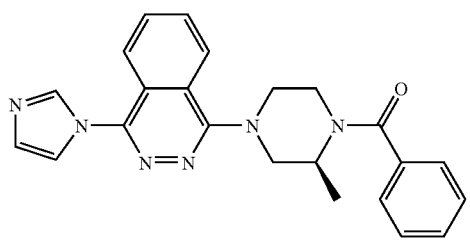

77

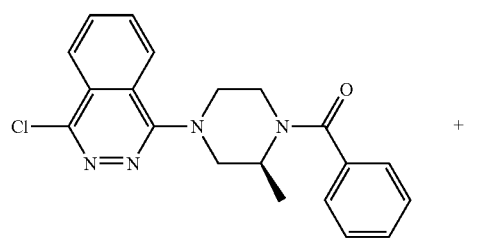

Compound 77 was prepared as described in general Method I. A 15 mL Schlenk tube was charged with (S)-(4-(4-chlorophthalazin-1-yl)-2-methylpiperazin-1-yl)(phenyl)methanone JK-4 (100 mg, 0.273 mmol), 1H-imidazole (22.3 mg, 0.328 mmol), copper (I) iodide (2.6 mg, 0.0136 mmol), potassium phosphate (122 mg, 0.573 mmol), trans-cyclohexanediamine (3.3 µl, 0.0273 mmol), and dioxane (0.75 mL). The vessel was evacuated, backfilled with argon 5 times, and then heated at 110° C. for 22 hours. After cooling, the reaction was then taken up in ethyl acetate (80 mL) and washed with aqueous $K_2CO_3$ (10%), water, and saturated sodium chloride. The organics were dried ($MgSO_4$) and evaporated to give a yellow oil. Chromatography over silica gel with a gradient of hexanes/0-100% ethyl acetate gave a white solid, compound 77. MS $(M+H)^+=399.2$.

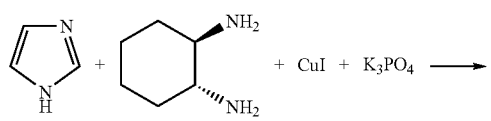

Example 45

The compounds summarized in Table 5 were prepared as described in detail in Example 44 using the appropriate substrates as indicated.

TABLE 5

| Comp # | Name | Structure | M Calc'd | M + 1 found | Precursor | Heterocycle |
|---|---|---|---|---|---|---|
| 78 | ((R)-4-(4-(1H-pyrazol-1-yl)phthalazin-1-yl)-3-methylpiperazin-1-yl)(phenyl)methanone | 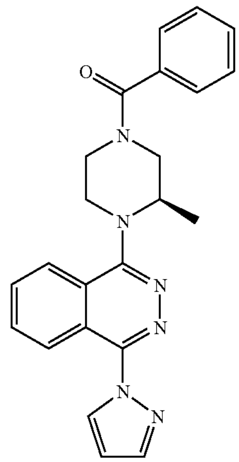 | 398.2 | 399.2 | JK-5 | 1H-pyrazole |
| 79 | ((R)-4-(4-(1H-indol-1-yl)phthalazin-1-yl)-3-methylpiperazin-1-yl)(phenyl)methanone | 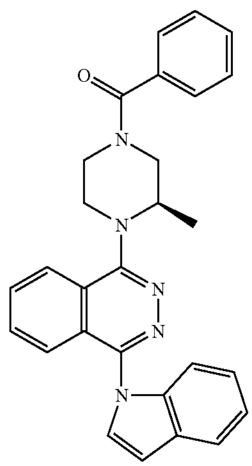 | 447.2 | 448.2 | JK-5 | 1H-indole |
| 80 | (R)-(4-(4-(1H-pyrrol-1-yl)phthalazin-1-yl)-3-methylpiperazin-1-yl)(phenyl)methanone | 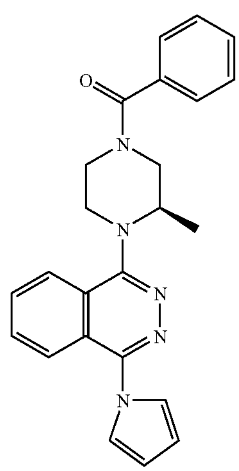 | 397.2 | 398.3 | JK-5 | 1H-pyrrole |

Example 46

Preparation of (R)-(4-(4-chlorophthalazin-1-yl)-3-methylpiperazin-1-yl)(4,4-difluorocyclohexyl)methanone (JK-27)

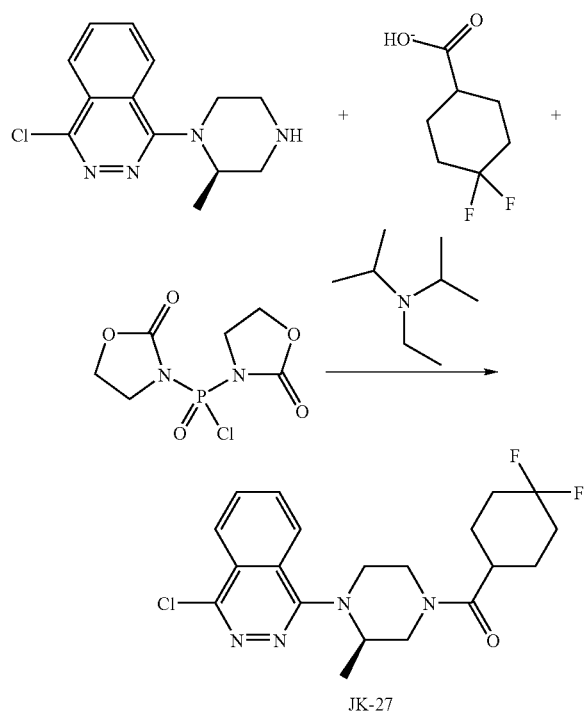

4,4-difluorocyclohexanecarboxylic acid (386 mg, 2.35 mmol) and bis(2-oxo-3-oxazolidinyl)phosphinic chloride (624 mg, 2.45 mmol), DMF (4 mL), and triethylamine (0.57 mL) were stirred at RT for 2 minutes. (R)-1-chloro-4-(2-methylpiperazin-1-yl)phthalazine (JK-2) (537 mg, 2.04 mmol) was added and the reaction stirred at rt for 24 hours. The reaction was then taken up in ethyl acetate (80 mL), washed with aqueous K$_2$CO$_3$ (10%), water, and then saturated sodium chloride. The organics were dried (MgSO$_4$) and evaporated to give a brown oil. Chromatography over silica gel with a gradient of hexanes/0-70% ethyl acetate gave an off-white solid, JK-27. MS (M+H)$^+$=409.1

Example 47

Preparation of (R)-(4-(4-(4-(hydroxymethyl)phenyl)phthalazin-1-yl)-3-methylpiperazin-1-yl)(phenyl)methanone (JK-28)

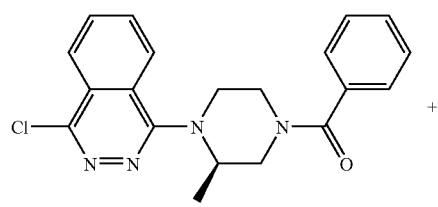

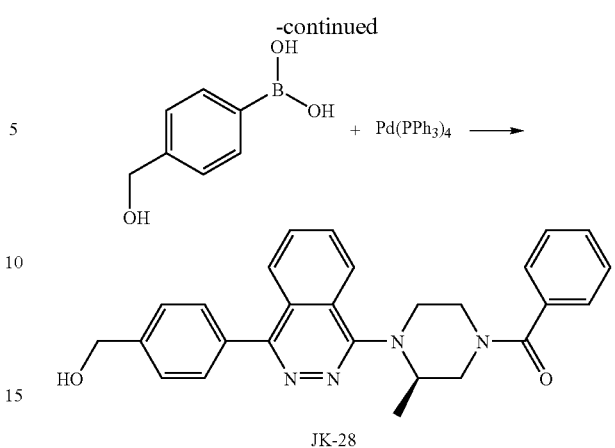

(R)-(4-(4-chlorophthalazin-1-yl)-3-methylpiperazin-1-yl)(phenyl)methanone (JK-5) (150 mg, 0.409 mmol), 4-(hydroxymethyl)phenylboronic acid (93.2 mg, 0.613 mmol), and tetrakis(triphenylphosphine)palladium (0) (23.6 mg, 0.023 mmol) were dissolved in toluene (4 mL) and aqueous sodium carbonate (2.0 M, 0.400 mL) under an atmosphere of argon. The reaction was heated at 100° C. for 15 hours, then cooled and taken up in ethyl acetate (80 mL). After washing with aqueous K$_2$CO$_3$ (10%), water, and then saturated sodium chloride, the organics were dried (MgSO$_4$) and evaporated to give a yellow oil. Chromatography over silica gel with a gradient of hexanes/0-100% ethyl acetate gave a pale yellow solid, JK-28. MS (M+H)$^+$=439.2.

Example 48

Preparation of (R)-cyclohexyl(4-(4-(4-(hydroxymethyl)phenyl)phthalazin-1-yl)-3-methylpiperazin-1-yl)methanone (JK-29)

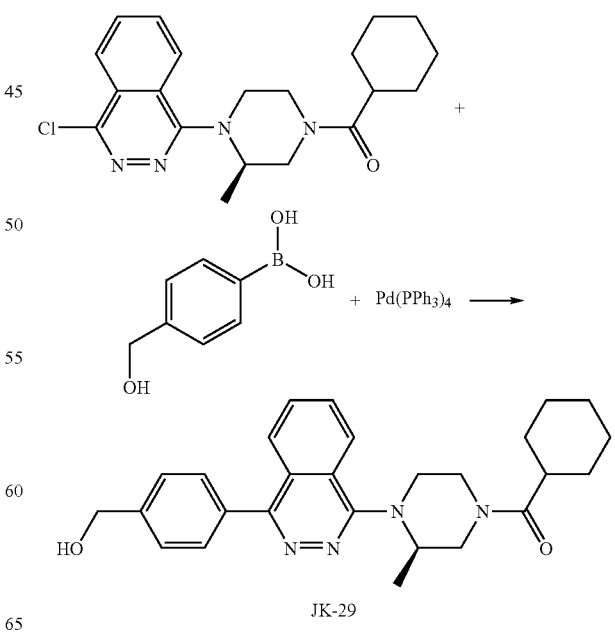

(R)-(4-(4-chlorophthalazin-1-yl)-3-methylpiperazin-1-yl)(cyclohexyl)methanone (JK-21) (150 mg, 0.402 mmol), 4-(hydroxymethyl)phenylboronic acid (85.6 mg, 0.563 mmol), and tetrakis(triphenylphosphine)palladium (0) (23.6 mg, 0.0201 mmol) were dissolved in toluene (5 mL) and aqueous sodium carbonate (2.0M, 0.500 mL) under an atmosphere of argon. The reaction was heated at 100° C. for 23 hours, then cooled and taken up in ethyl acetate (80 mL). After washing with aqueous $K_2CO_3$ (10%), water, and saturated sodium chloride, the organics were dried ($MgSO_4$) and evaporated to give a yellow oil. Chromatography over silica gel with a gradient of hexanes/0-100% ethyl acetate gave a pale yellow solid, JK-29. MS (M+H)+=445.4.

Example 49

Preparation of (R)-(4-(4-(4-benzoyl-2-methylpiperazin-1-yl)phthalazin-1-yl)phenyl)methyl carbamate (81)

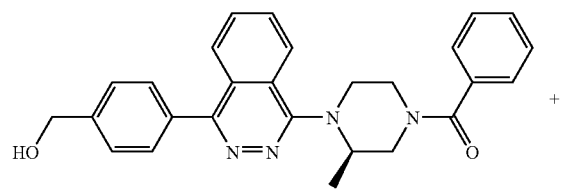

+

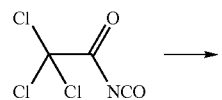

→

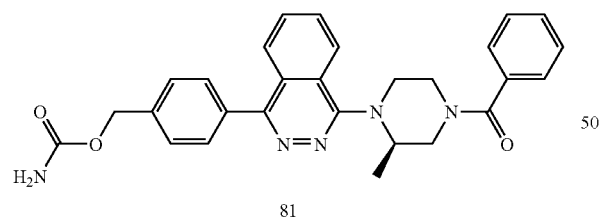

81

Compound 81 was prepared as described in general Method K. (R)-(4-(4-(4-(hydroxymethyl)phenyl)phthalazin-1-yl)-3-methylpiperazin-1-yl)(phenyl)methanone (JK-28) (125 mg, 0.285 mmol), was dissolved in chloroform (2.50 mL). 2,2,2-trichloroacetyl isocyanate (40.5 µl, 0.342 mmol) was added and the reaction stirred at rt for 80 minutes. The reaction was adsorbed onto alumina (Brockmann II, 3 g), and after 2 hours was eluted with 10% methanol in dichloromethane. The resulting solution was evaporated to give a yellow oil. Chromatography over silica gel with a gradient of hexanes/0-45% ethyl acetate gave a pale yellow solid, compound 81. MS (M+H)+=482.2

Example 50

Preparation of (R)-(4-(4-(4-(cyclohexanecarbonyl)-2-methylpiperazin-1-yl)phthalazin-1-yl)phenyl)methyl carbamate (82)

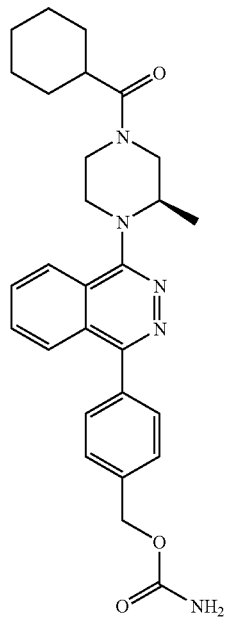

82

Compound 82 was prepared as described in Example 49 using JK-29. MS (M+H)+=488.2.

Example 51

Preparation of ((R)-3-methyl-4-(4-(4-(2-(tetrahydro-2H-pyran-2-yloxy)ethyl)phenyl)phthalazin-1-yl)piperazin-1-yl)(phenyl)methanone (83)

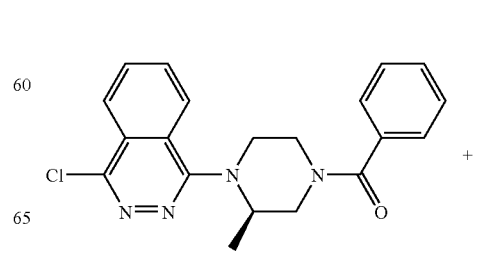

+

-continued

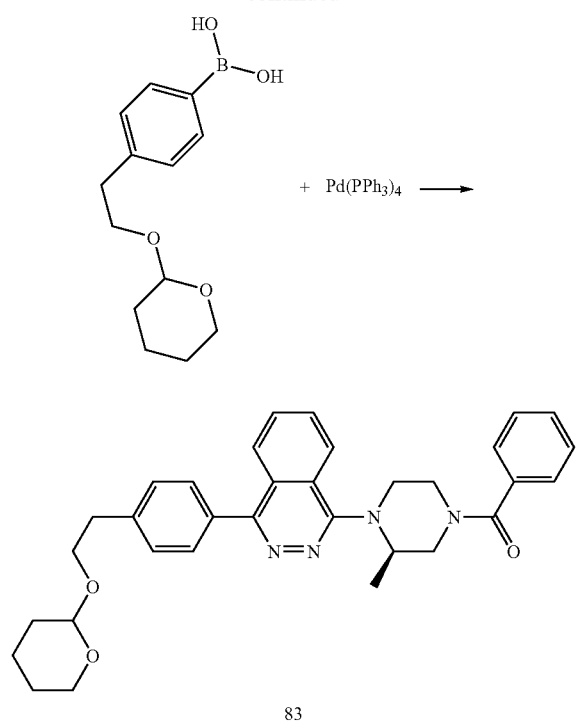

83

(R)-(4-(4-chlorophthalazin-1-yl)-3-methylpiperazin-1-yl)(phenyl)methanone (JK-5) (200 mg, 0.545 mmol), 4-(2-(tetrahydro-2H-pyran-2-yloxy)ethyl)phenylboronic acid (136 mg, 0.545 mmol) and tetrakis(triphenylphosphine)palladium (0) (31.5 mg, 0.0273 mmol) were dissolved in toluene (4 mL) and aqueous sodium carbonate (2.0M, 0.400 mL) under an atmosphere of argon. The reaction was heated at 100° C. for 15 hours, cooled to rt, and taken up in ethyl acetate (80 mL). After washing with aqueous K$_2$CO$_3$ (10%), water, and saturated sodium chloride, the organics were dried (MgSO$_4$) and evaporated to give a yellow oil. Chromatography over silica gel with a gradient of hexanes/0-100% ethyl acetate gave a pale yellow solid, compound 83. MS (M+H)$^+$=537.4.

Example 52

Preparation of (R)-(4-(4-(4-(2-hydroxyethyl)phenyl)phthalazin-1-yl)-3-methylpiperazin-1-yl)(phenyl)methanone (84)

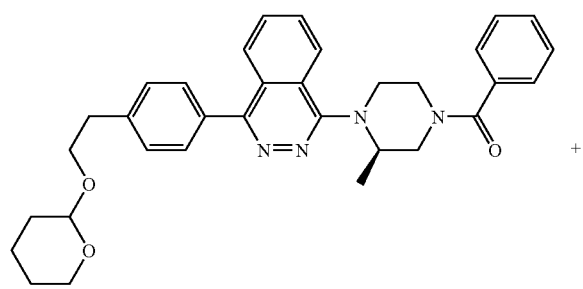

+

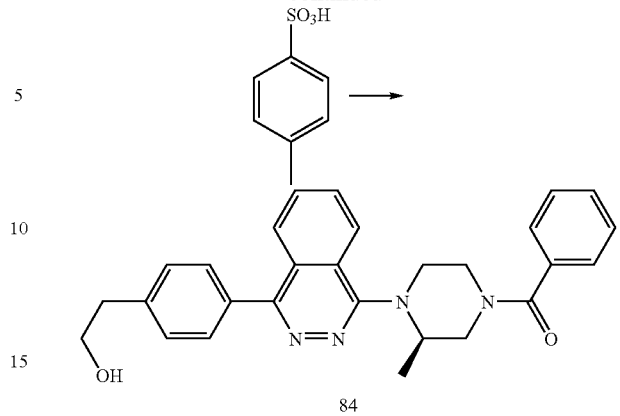

84

((R)-3-methyl-4-(4-(4-(2-(tetrahydro-2H-pyran-2-yloxy)ethyl)phenyl)phthalazin-1-yl)piperazin-1-yl)(phenyl)methanone (122 mg, 0.227 mmol) 83 and p-toluenesulfonic acid (130 mg, 0.682 mmol) were dissolved in methanol (4 mL) and stirred at rt for 1.5 hours. The reaction was added to 35 mL aqueous K$_2$CO$_3$ (10%) and extracted three times with 30 mL portions of dichloromethane. The combined organic extracts were dried over MgSO$_4$ and evaporated to give a pale yellow solid, compound 84. MS (M+H)$^+$=453.2.

Example 53

Smoothened Receptor Activity

Antagonist activity of compounds for mouse Smoothened was assessed by measuring inhibition of Luciferase activity in Shh-stimulated NIH-3T3 cells stably transfected with a luciferase reporter construct with 5 GLI binding sites upstream of a basal promoter, similar to methods described by others (Chen et al. (2002) *PNAS* 99 14071-14076; Taipale et al. (2000) *Nature* 406 1005-1009.) Antagonist activity of compounds on human Smoothened was assessed by measuring inhibition of GLI1 transcription in Shh-stimulated HEPM cells (American Type Culture Collection, Manassas, Va. USA), similar to methods described by others. See U.S. Pat. No. 6,613,798. For this work GLI1 transcription in HEPM cells was measured using a Quantigene assay specific for GLI1 (Panomics Inc., Freemont, Calif., USA) in place of PCR based methods.

All exemplified compounds demonstrated antagonist activity of 1 μM or less.

Example 54

Smoothened Antagonist Activity In Vivo

Depilation has been demonstrated to induce the Hh pathway in mouse skin, including increased transcription of the Gli1 gene. Paladini et al. (2005) J Invest Dermatol 125:638-646. For this work, the mice were depilated using wax strips (Sally Hansen, Del Laboratories, Inc, Uniondale, N.Y.). Five days after depilation, mice were dosed orally with compound or vehicle. Six hours after compound administration, animals were euthanized and skin samples were collected. RNA was purified from the skin samples using a mirVana miRNA Isolation kit (Ambion, Austin, Tex.). cDNA was prepared from the RNA, and Gli1 expression levels were determined by real-time, quantitative PCR relative to the RGS reference gene. As illustrated in Table 6, compounds of the invention reduced Gli1 expression compared to the vehicle, thus demonstrating inhibition of Smoothened signaling in vivo.

TABLE 6

Gli1 Expression in Mouse Skins After Compound Dosing

| Compound | Dose (mg/kg) | [Gli1/RGS ratio compound]/ [Gli1/RGS ratio vehicle] |
|---|---|---|
| 5 | 100 | 0.41 |
| 23 | 50 | 0.33 |

Example 55

Antitumor Activity In Vivo

Figure 2:
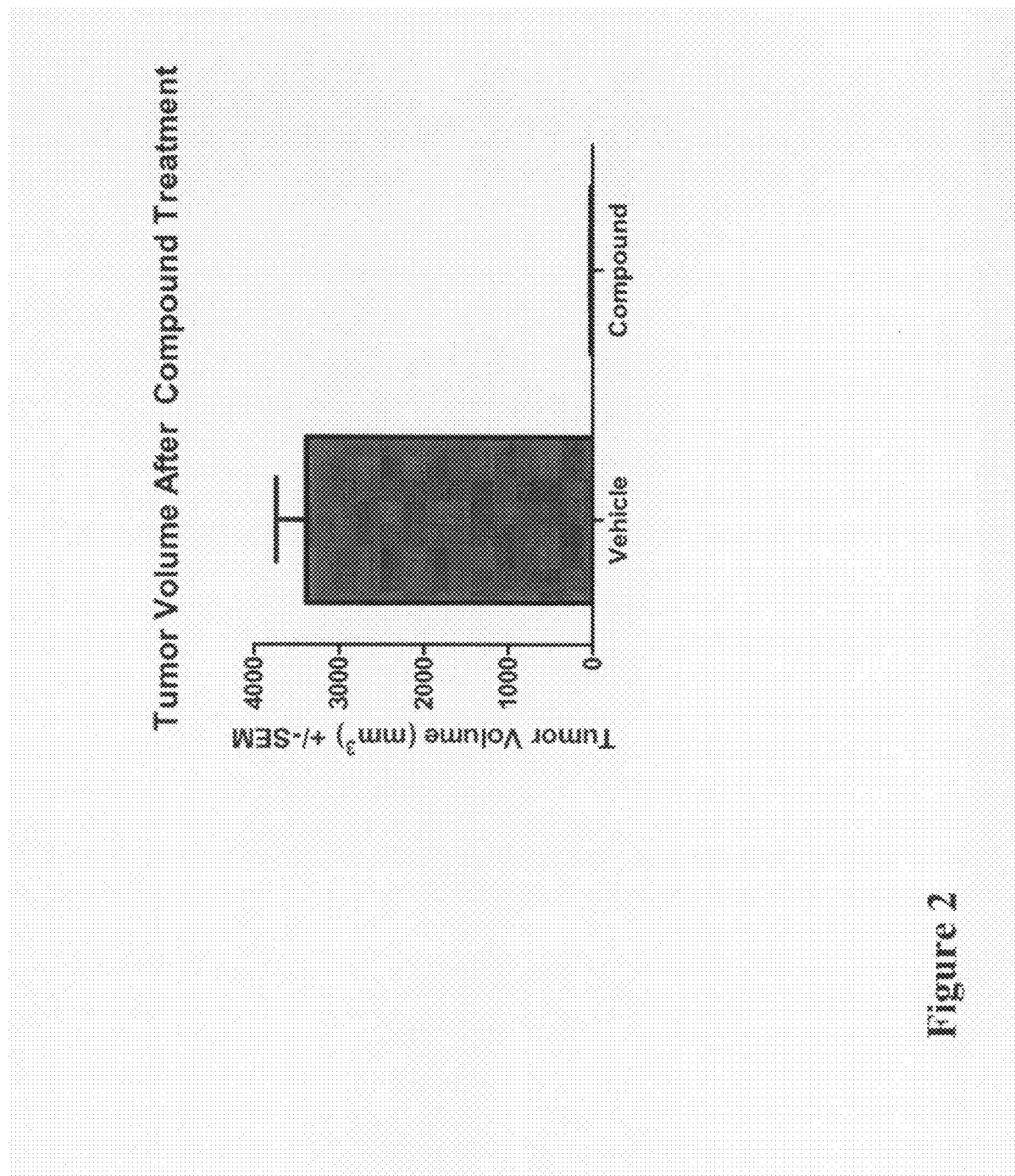
FIG. 2 illustrates the comparison of volume of primary pancreatic tumors grown in compound versus vehicle treated mice.

Anti-tumor activity of compound 23 was demonstrated using a mouse medulloblastoma allograft model (Sasai, K. et al. (2006) *Cancer Research* 66:4215-4222). Briefly, medulloblastomas from Ptch+/−p53−/− mice were subcutaneously implanted into immunocompromised mice, and subsequent passages of these tumor allografts were used for compound testing. For compound studies, animals bearing tumors with an average size of 200 mm$^3$ were treated with vehicle or 10 mg/kg compound 23 on a schedule of one dose per day for a total of 6 days. The treatment resulted in a >99% reduction in tumor size relative to vehicle control after 6 days of treatment, see FIGS. 1 and 2.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:
1. A compound of Formula I

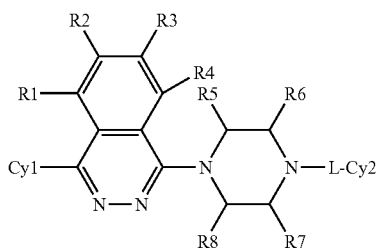

or a pharmaceutically acceptable salt thereof, wherein
Cy$^1$ is a partially or fully saturated or unsaturated 3-8 membered monocyclic, or 6-12 membered bicyclic ring system, the ring system formed of carbon atoms optionally including 1-3 heteroatoms if monocyclic, or 1-6 heteroatoms if bicyclic, and wherein each ring of the ring system is optionally substituted independently with 1-5 substituents, wherein the substituents are selected from the group consisting of C$_{1-8}$alkyl, C$_{2-8}$alkenyl, C$_{2-8}$alkynyl, C$_{1-6}$haloalkyl, halogen, cyano, hydroxy, oxo, —OR$^c$, —NR$^a$R$^b$, NR$^a$C(=O)R$^b$, —C(=O)OR$^c$, —R$^c$OC(=O)NR$^a$R$^b$, —R$^c$OH, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and S(=O)$_m$R$^c$;
R$^1$, R$^2$, R$^3$, and R$^4$ are each H;

R$^5$, R$^6$, R$^7$, and R$^8$ are each independently selected from H, C$_{1-6}$alkyl, C$_{1-6}$haloalkyl, oxo, —C(=O)OR$^a$, —R$^c$OH, —OR$^c$, —NR$^a$R$^b$, NR$^a$C(=O)R$^b$, —C(=O)OR$^c$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and S(=O)$_m$R$^c$, provided that at least one of R$^5$, R$^6$, R$^7$, and R$^8$ is not H;
R$^a$, R$^b$, and R$^c$ are each independently selected from H, C$_{1-8}$alkyl, C$_{2-8}$alkenyl, C$_{2-8}$alkynyl, C$_{1-6}$haloalkyl, heterocyclyl, aryl, and heteroaryl;
m is 1 or 2;
L is —C(=O)—, —S(=O)$_m$— or —CH$_2$—;
Cy$^2$ is a partially or fully saturated or unsaturated 3-8 membered monocyclic ring system, the ring system formed of carbon atoms optionally including 1-3 heteroatoms, and wherein the ring system is optionally substituted independently with 1-5 substituents, wherein the substituents are selected from the group consisting of C$_{1-8}$alkyl, C$_{2-8}$alkenyl, C$_{2-8}$alkynyl, C$_{1-6}$haloalkyl, halogen, cyano, hydroxy, oxo, —C(=O)OR$^c$, —R$^c$OH, —OR$^c$, —NR$^a$R$^b$, NR$^a$C(=O)R$^b$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and S(=O)$_m$R$^c$.

2. The compound of claim 1 or a pharmaceutically acceptable salt thereof, wherein Cy$^1$ is aryl optionally substituted independently with 1-5 substituents selected from C$_{1-8}$alkyl, C$_{2-8}$alkenyl, C$_{2-8}$alkynyl, C$_{1-6}$haloalkyl, halogen, cyano, hydroxy, oxo, —C(=O)OR$^c$, —R$^c$OH, —OR$^c$, —NR$^a$R$^b$, NR$^a$C(=O)R$^b$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and S(=O)$_m$R$^c$.

3. The compound of claim 1 or a pharmaceutically acceptable salt thereof, wherein Cy$^1$ is cycloalkyl optionally substituted independently with 1-5 substituents selected from C$_{1-8}$alkyl, C$_{2-8}$alkenyl, C$_{2-8}$alkynyl, C$_{1-6}$haloalkyl, halogen, cyano, hydroxy, oxo, —C(=O)OR$^c$, —R$^c$OH, —OR$^c$, —NR$^a$R$^b$, NR$^a$C(=O)R$^b$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and S(=O)$_m$R$^c$.

4. The compound of claim 1 or a pharmaceutically acceptable salt thereof, wherein Cy$^1$ is heteroaryl optionally substituted independently with 1-5 substituents selected from C$_{1-8}$alkyl, C$_{2-8}$alkenyl, C$_{2-8}$alkynyl, C$_{1-6}$haloalkyl, halogen, cyano, hydroxy, oxo, —C(=O)OR$^c$, —R$^c$OH, —OR$^c$, —NR$^a$R$^b$, NR$^a$C(=O)R$^b$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and S(=O)$_m$R$^c$.

5. The compound of claim 2 or a pharmaceutically acceptable salt thereof, wherein Cy$^1$ is phenyl optionally substituted independently with 1-5 substituents selected from C$_{1-8}$alkyl, C$_{2-8}$alkenyl, C$_{2-8}$alkynyl, C$_{1-6}$haloalkyl, halogen, cyano, hydroxy, oxo, —C(=O)OR$^c$, —R$^c$OH, —OR$^c$, —NR$^a$R$^b$, NR$^a$C(=O)R$^b$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and S(=O)$_m$R$^c$.

6. The compound of claim 1 or a pharmaceutically acceptable salt thereof, wherein Cy$^1$ is naphthyl, furanyl, benzopuranyl, thienyl, imidazolyl, triazolyl, quinoxalinyl, benzodioxolyl, benzodioxinyl, indolinyl, indolyl, indazolyl, benzoimidazolyl, benzoisoxazolyl, benzoxazolyl, benzothiazolyl, thiazolyl, oxazolyl, morpholinyl, pyridyl, pyrimidinyl, pyrrolidinyl, pyrazonyl, pyranyl, dihidropyranyl, tetrahydropyranyl, pyrazolyl, pyrrolyl, pipearazinyl, piperadinyl, pyridazinyl, phthalazinyl, azetidinyl, quinolinyl, quinazolinyl, dihydroquinolinyl, isoquinolinyl or cinnolinyl, any of which can be optionally substituted independently with 1-5 substituents selected from C$_{1-8}$alkyl, C$_{2-8}$alkenyl, C$_{2-8}$alkynyl, C$_{1-6}$haloalkyl, halogen, cyano, hydroxy, oxo, —C(=O)OR$^c$, —R$^c$OH, —OR$^c$, —NR$^a$R$^b$, NR$^a$C(=O)R$^b$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and S(=O)$_m$R$^c$.

7. The compound of any of claims 2-6 or a pharmaceutically acceptable salt thereof, wherein the substituents are selected independently from the group consisting of C$_{1-8}$alkyl, C$_{2-8}$alkenyl, C$_{1-6}$haloalkyl, cyano, hydroxy and halogen.

8. The compound of claim 1 or a pharmaceutically acceptable salt thereof, wherein R$^5$, R$^6$, R$^7$, and R$^8$ are each independently selected from H, C$_{1-6}$alkyl and C$_{1-6}$haloalkyl, provided that at least one of R$^5$, R$^6$, R$^7$, and R$^8$ is not H.

9. The compound of claim 8 or a pharmaceutically acceptable salt thereof, wherein R$^5$, R$^6$, R$^7$ are each H, and R$^8$ is C$_{1-6}$alkyl.

10. The compound of claim 9 or a pharmaceutically acceptable salt thereof, wherein R$^8$ is methyl.

11. The compound of claim 8 or a pharmaceutically acceptable salt thereof, wherein R$^5$ and R$^7$ are each H, and R$^6$ and R$^8$ are each independently C$_{1-6}$alkyl.

12. The compound of claim 8 or a pharmaceutically acceptable salt thereof, wherein R$^6$ and R$^8$ are each methyl.

13. The compound of claim 8 or a pharmaceutically acceptable salt thereof, wherein R$^5$, R$^7$ and R$^8$ are each H, and R$^6$ is C$_{1-6}$alkyl.

14. The compound of claim 8 or a pharmaceutically acceptable salt thereof, wherein R$^5$, R$^6$, and R$^8$ are each H, and R$^7$ is C$_{1-6}$alkyl.

15. The compound of claim 8 or a pharmaceutically acceptable salt thereof, wherein R$^6$, R$^7$, and R$^8$ are each H, and R$^5$ is C$_{1-6}$alkyl.

16. The compound of claim 8 or a pharmaceutically acceptable salt thereof, wherein R$^5$ and R$^7$ are each independently C$_{1-6}$alkyl, and R$^6$ and R$^8$ are each H.

17. The compound of claim 1 or a pharmaceutically acceptable salt thereof, wherein L is —C(=O)—.

18. The compound of claim 1 or a pharmaceutically acceptable salt thereof, wherein L is —S(=O)$_2$—.

19. The compound of claim 1 or a pharmaceutically acceptable salt thereof, wherein L is —CH$_2$—.

20. The compound of claim 1 or a pharmaceutically acceptable salt thereof, wherein Cy$^2$ is cycloalkyl or heterocycloalkyl, any of which can be optionally substituted independently with 1-5 substituents selected from C$_{1-8}$alkyl, C$_{2-8}$alkenyl, C$_{2-8}$alkynyl, C$_{1-6}$haloalkyl, halogen, cyano, hydroxy, oxo, —C(=O)OR$^c$, —R$^c$OH, —OR$^c$, —NR$^a$R$^b$, NR$^a$C(=O)R$^b$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and S(=O)$_m$R$^c$.

21. The compound of claim 20 or a pharmaceutically acceptable salt thereof, wherein Cy$^2$ is cyclopropyl, cyclobutyl, cyclopentyl, cyclohexyl, or cycloheptyl, any of which can be optionally substituted independently with 1-5 substituents selected from C$_{1-8}$alkyl, C$_{2-8}$alkenyl, C$_{2-8}$alkynyl, C$_{1-6}$haloalkyl, halogen, cyano, hydroxy, oxo, —C(=O)OR$^c$, —R$^c$OH, —OR$^c$, —NR$^a$R$^b$, NR$^a$C(=O)R$^b$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and S(=O)$_m$R$^c$.

22. The compound of claim 1 or a pharmaceutically acceptable salt thereof, wherein Cy$^2$ is aryl or heteroaryl, any of which can be optionally substituted independently with 1-5 substituents selected C$_{1-8}$alkyl, C$_{2-8}$alkenyl, C$_{2-8}$alkynyl, C$_{1-6}$haloalkyl, halogen, cyano, hydroxy, oxo, —C(=O)OR$^c$, —R$^c$OH, —OR$^c$, —NR$^a$R$^b$, NR$^a$C(=O)R$^b$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and S(=O)$_m$R$^c$.

23. The compound of claim 22 or a pharmaceutically acceptable salt thereof, wherein Cy$^2$ is phenyl optionally substituted independently with 1-5 substituents selected from C$_{1-8}$alkyl, C$_{2-8}$alkenyl, C$_{2-8}$alkynyl, C$_{1-6}$haloalkyl, halogen, cyano, hydroxy, oxo, —C(=O)OR$^c$, —R$^c$OH, —OR$^c$, —NR$^a$R$^b$, NR$^a$C(=O)R$^b$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and S(=O)$_m$R$^c$.

24. The compound of any of claim 20 or 22 or a pharmaceutically acceptable salt thereof, wherein the substituents are selected from the group consisting of C$_{1-8}$alkyl, C$_{1-6}$haloalkyl, halogen, cyano, hydroxyl and oxo.

25. The compound of claim 1 selected from
(2-methyl-4-(4-phenyl-phthalazin-1-yl)piperazin-1-yl)-(thiophen-2-yl)-methanone,
(2-methyl-4-(4-phenylphthalazin-1-yl)piperazin-1-yl)(phenyl)methanone,
phenyl(5-(4-phenylphthalazin-1-yl)-2,5-diaza-bicyclo[2.2.1]-heptan-2-yl)-methanone,
(3-methyl-4-(4-phenylphthalazin-1-yl)piperazin-1-yl)(phenyl)methanone,
(2-methyl-4-(4-phenylphthalazin-1-yl)piperazin-1-yl)(phenyl)-methanone,
(4-(4-(4-chlorophenyl)phthalazin-1-yl)-2-methylpiperazin-1-yl)(phenyl)methanone,
(2-methyl-4-(4-p-tolylphthalazin-1-yl)piperazin-1-yl)(phenyl)methanone,
4-(4-(3,4-dichlorophenyl)-phthalazin-1-yl)-2-methylpiperazin-1-yl)(phenyl)-methanone,
(3-methyl-4-(4-phenylphthalazin-1-yl)piperazin-1-yl)(phenyl)-methanone,
2,6-dimethyl-4-(4-phenylphthalazin-1-yl)piperazin-1-yl)(phenyl)-methanone,
(2-methyl-4-(4-phenylphthalazin-1-yl)piperazin-1-yl)(pyridin-3-yl)methanone,
(2-methyl-4-(4-phenylphthalazin-1-yl)piperazin-1-yl)(pyridin-4-yl)methanone,
(2-methyl-4-(4-phenylphthalazin-1-yl)piperazin-1-yl)(thiazol-2-yl)methanone,
cyclopentyl(3-methyl-4-(4-phenylphthalazin-1-yl)piperazin-1-yl)methanone,
cyclopropyl(3-methyl-4-(4-phenylphthalazin-1-yl)piperazin-1-yl)methanone,
cyclohexyl(3-methyl-4-(4-phenylphthalazin-1-yl)piperazin-1-yl)methanone,
2-methyl-4-(4-(pyridin-2-yl)phthalazin-1-yl)piperazin-1-yl)(phenyl)methanone,
3-methyl-4-(4-(pyridin-2-yl)phthalazin-1-yl)piperazin-1-yl)(phenyl)methanone,
(3-methyl-4-(4-p-tolylphthalazin-1-yl)piperazin-1-yl)(phenyl)-methanone,
(4-(4-(4-chlorophenyl)-phthalazin-1-yl)-3-methylpiperazin-1-yl)(phenyl)-methanone,
(4-(4-(4-tert-butylphenyl)-phthalazin-1-yl)-3-methyl-piperazin-1-yl)(phenyl)-methanone,
(3-methyl-4-(4-(4-(trifluoromethyl)-phenyl)-phthalazin-1-yl)piperazin-1-yl) (phenyl)-methanone,
(4-(4-(4-isopropylphenyl)-phthalazin-1-yl)-3-methylpiperazin-1-yl)(phenyl)-methanone,
4-(4-(benzofuran-2-yl)phthalazin-1-yl)-3-methylpiperazin-1-yl)(phenyl)-methanone,
(2,5-dimethyl-4-(4-phenylphthalazin-1-yl)piperazin-1-yl)(phenyl)methanone,
2,5-dimethyl-4-(4-(4-(trifluoromethyl)-phenyl)-phthalazin-1-yl)piperazin-1-yl)(phenyl)methanone, (2-methyl-4-(4-(4-(trifluoromethyl)phenyl)phthalazin-1-yl)piperazin-1-yl)(phenyl)methanone,
(2-methyl-4-(4-(4-vinylphenyl)phthalazin-1-yl)piperazin-1-yl)(phenyl)methanone,
4-(4-(2-fluoro-4-methylphenyl)phthalazin-1-yl)-2-methylpiperazin-1-yl)(phenyl)methanone,
4-(4-(3-fluoro-4-methylphenyl)phthalazin-1-yl)-2-methylpiperazin-1-yl)(phenyl)methanone,
4-(4-(2-fluorophenyl)phthalazin-1-yl)-2-methylpiperazin-1-yl)(phenyl)methanone,
4-(4-(2-fluoro-4-methylphenyl)phthalazin-1-yl)-3-methylpiperazin-1-yl)(phenyl)methanone,
4-(4-(3-fluoro-4-methylphenyl)phthalazin-1-yl)-3-methylpiperazin-1-yl)(phenyl)methanone,
4-(4-(4-chloro-2-fluorophenyl)phthalazin-1-yl)-3-methylpiperazin-1-yl)(phenyl)methanone,
4-(4-(4-chloro-2-fluorophenyl)phthalazin-1-yl)-2-methylpiperazin-1-yl)(phenyl)methanone,
4-(4-(2-fluorophenyl)phthalazin-1-yl)-3-methylpiperazin-1-yl)(phenyl)methanone,
1-benzyl-4-(4-(4-(trifluoromethyl)phenyl)phthalazin-1-yl)piperazin-2-one,
(4-(4-(4-fluorophenyl)phthalazin-1-yl)-3-methylpiperazin-1-yl)(phenyl)methanone,
methyl 4-(4-(4-benzoyl-2-methylpiperazin-1-yl)phthalazin-1-yl)benzoate,
(4-(4-(4-(dimethylamino)phenyl)phthalazin-1-yl)-3-methylpiperazin-1-yl)(phenyl)methanone,
methyl 1-benzoyl-4-(4-phenylphthalazin-1-yl)piperazine-2-carboxylate,
2,5-dimethyl-4-(4-phenylphthalazin-1-yl)piperazin-1-yl)(phenyl)methanone,
4-(4-(4-benzoyl-2-methylpiperazin-1-yl)phthalazin-1-yl)benzonitrile,
(4-(4-(4-(hydroxymethyl)phenyl)phthalazin-1-yl)-3-methylpiperazin-1-yl)(phenyl)methanone,
cyclohexyl(4-(4-(4-fluorophenyl)phthalazin-1-yl)-3-methylpiperazin-1-yl)methanone,
cyclohexyl(4-(4-(4-(hydroxymethyl)phenyl)phthalazin-1-yl)-3-methylpiperazin-1-yl)methanone,
(4-(4-cyclopropylphthalazin-1-yl)-2-methylpiperazin-1-yl)(phenyl)methanone,
(2-methyl-4-(4-(pyridin-4-yl)phthalazin-1-yl)piperazin-1-yl)(phenyl)methanone,
(3-methyl-4-(4-(pyridin-4-yl)phthalazin-1-yl)piperazin-1-yl)(phenyl)methanone,
(4-(4-(4-(hydroxymethyl)phenyl)phthalazin-1-yl)-2,5-dimethylpiperazin-1-yl)(phenyl)methanone,
(4-(4-(4-chloro-2-fluorophenyl)phthalazin-1-yl)-2,5-dimethylpiperazin-1-yl)(phenyl)methanone,
(2,2-dimethyl-4-(4-phenylphthalazin-1-yl)piperazin-1-yl)(phenyl)methanone,
4-(4-(4-(4,4-difluorocyclohexanecarbonyl)-2-methylpiperazin-1-yl)phthalazin-1-yl)benzonitrile,
(3-methyl-4-(4-morpholinophthalazin-1-yl)piperazin-1-yl)(phenyl)methanone,
1-(3-methyl-4-(phenylsulfonyl)piperazin-1-yl)-4-phenylphthalazine,
1-(2-methyl-4-(phenylsulfonyl)piperazin-1-yl)-4-phenylphthalazine,
4-(2-methyl-1-(4-phenylphthalazin-1-yl)piperazine-4-carbonyl)cyclohexanone,
3-(2-methyl-1-(4-phenylphthalazin-1-yl)piperazine-4-carbonyl)cyclohexanone,
4-(4-(4-benzoyl-2-methylpiperazin-1-yl)phthalazin-1-yl)benzamide,
4-(4-(4-(cyclohexanecarbonyl)-2-methylpiperazin-1-yl)phthalazin-1-yl)benzonitrile,
2-methyl-4-(4-(pyridin-3-yl)phthalazin-1-yl)piperazin-1-yl)(phenyl)methanone,
3-methyl-4-(4-(pyridin-3-yl)phthalazin-1-yl)piperazin-1-yl)(phenyl)methanone,
4-(4-(4-benzoyl-2,5-dimethylpiperazin-1-yl)phthalazin-1-yl)benzonitrile,
4-(4-(1H-imidazol-1-yl)phthalazin-1-yl)-2-methylpiperazin-1-yl)(phenyl)methanone,
4-(4-(1H-pyrazol-1-yl)phthalazin-1-yl)-3-methylpiperazin-1-yl)(phenyl)methanone,
4-(4-(1H-indol-1-yl)phthalazin-1-yl)-3-methylpiperazin-1-yl)(phenyl)methanone,
4-(4-(1H-pyrrol-1-yl)phthalazin-1-yl)-3-methylpiperazin-1-yl)(phenyl)methanone,
(4-(4-(4-benzoyl-2-methylpiperazin-1-yl)phthalazin-1-yl)phenyl)methyl carbamate,
(4-(4-(4-(cyclohexanecarbonyl)-2-methylpiperazin-1-yl)phthalazin-1-yl)phenyl)methyl carbamate,
3-methyl-4-(4-(4-(2-(tetrahydro-2H-pyran-2-yloxy)ethyl)phenyl)phthalazin-1-yl)piperazin-1-yl)(phenyl)methanone, and
4-(4-(4-(2-hydroxyethyl)phenyl)phthalazin-1-yl)-3-methylpiperazin-1-yl)(phenyl)methanone,
or a stereoisomer or a pharmaceutically acceptable salt thereof.

26. A pharmaceutical composition comprising a compound of claim 1 or a pharmaceutically acceptable salt thereof and a pharmaceutically acceptable carrier.

27. A pharmaceutical composition comprising a compound of claim 25 or a pharmaceutically acceptable salt thereof and a pharmaceutically acceptable carrier.

\* \* \* \* \*